United States Patent
Fuesslein et al.

(10) Patent No.: US 9,868,719 B2
(45) Date of Patent: Jan. 16, 2018

(54) COMPOUNDS WITH PESTICIDAL ACTIVITY

(71) Applicant: BAYER CROPSCIENCE AKTIENGESELLSCHAFT, Monheim am Rhein (DE)

(72) Inventors: Martin Fuesslein, Duesseldorf (DE); Anne Decor, Langenfeld (DE); Joerg Nico Greul, Leverkusen (DE); Hans-Georg Schwarz, Dorsten (DE); Daniela Portz, Vettweiss (DE); Kerstin Ilg, Cologne (DE); Olga Malsam, Roesrath (DE); Peter Luemmen, Idstein (DE); Ulrich Goergens, Ratingen (DE); Claudia Welz, Duesseldorf (DE); Adeline Koehler, Langenfeld (DE); Kirsten Boerngen, Cologne (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/914,069

(22) PCT Filed: Aug. 25, 2014

(86) PCT No.: PCT/EP2014/067998
§ 371 (c)(1),
(2) Date: Feb. 24, 2016

(87) PCT Pub. No.: WO2015/028427
PCT Pub. Date: Mar. 5, 2015

(65) Prior Publication Data
US 2016/0198708 A1    Jul. 14, 2016

(30) Foreign Application Priority Data

Aug. 26, 2013 (EP) .................................. 13181692

(51) Int. Cl.

| | |
|---|---|
| *C07D 401/04* | (2006.01) |
| *A01N 43/60* | (2006.01) |
| *C07D 405/04* | (2006.01) |
| *C07D 401/14* | (2006.01) |
| *A01N 43/40* | (2006.01) |
| *A01N 43/50* | (2006.01) |
| *A01N 43/56* | (2006.01) |
| *A01N 43/653* | (2006.01) |

(52) U.S. Cl.
CPC .......... *C07D 401/04* (2013.01); *A01N 43/40* (2013.01); *A01N 43/50* (2013.01); *A01N 43/56* (2013.01); *A01N 43/60* (2013.01); *A01N 43/653* (2013.01); *C07D 401/14* (2013.01); *C07D 405/04* (2013.01)

(58) Field of Classification Search
None
See application file for complete search history.

(56) References Cited

U.S. PATENT DOCUMENTS

| | | | |
|---|---|---|---|
| 8,378,114 B2 * | 2/2013 | Oda ....................... | A01N 37/18 544/407 |
| 8,815,772 B2 | 8/2014 | Bereznak et al. | |
| 2014/0249149 A1 | 9/2014 | Greul et al. | |
| 2014/0256728 A1 | 9/2014 | Greul et al. | |

FOREIGN PATENT DOCUMENTS

| | | |
|---|---|---|
| EP | 2132987 A1 | 12/2009 |
| WO | 2007/108483 A1 | 9/2007 |
| WO | 2012118139 A1 | 9/2012 |
| WO | 2013/064460 A1 | 5/2013 |
| WO | 2013/064461 A2 | 5/2013 |
| WO | 2013/064518 A1 | 5/2013 |
| WO | 2013/064519 A1 | 5/2013 |
| WO | 2013/064520 A1 | 5/2013 |
| WO | 2013/064521 A1 | 5/2013 |
| WO | 2014/004064 A1 | 1/2014 |
| WO | 2014034750 A1 | 3/2014 |
| WO | 2014034751 A1 | 3/2014 |

OTHER PUBLICATIONS

International Search Report from corresponding PCT/EP2014/067998, dated Jan. 12, 2015.
Kers et al., "Phenethyl nicotinamides, a novel class of Nav1.7 channel blockers: Structure and activity relationship" Bioorganic and Medical Chemistry Letters. (2012) pp. 6108-6115.

* cited by examiner

*Primary Examiner* — Abigail Vanhorn
(74) *Attorney, Agent, or Firm* — McBee Moore Woodward & Vanik IP, LLC

(57) ABSTRACT

Disclosed are compounds of formula (I) which possess pesticidal, especially nematicidal properties

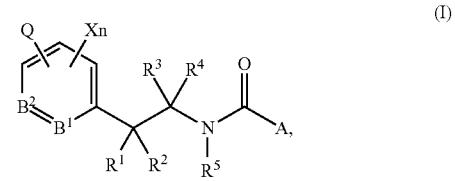

wherein the structural elements have the meaning as indicated in the description.

15 Claims, No Drawings

COMPOUNDS WITH PESTICIDAL ACTIVITY

CROSS REFERENCE TO RELATED APPLICATIONS

This application is a §371 National Stage Application of PCT/EP2014/067998, filed 25 Aug. 2014 which claims priority to EP 13181692.8, filed 26 Aug. 2013.

BACKGROUND

Field of the Invention

The present invention relates to certain pyridyl carboxamide derivatives as to processes for their preparation, to compositions comprising those compounds and their use in agriculture and veterinary fields and fields relying on pest management. The compounds are active for controlling plant damaging pests; they are particularly active for the control of nematodes. Furthermore, the compounds act as anthelmintic agents against endoparasites in animals and humans.

Description of Related Art

Nematodes cause a substantial loss in agricultural product including food and industrial crops and are combated with chemical compounds having nematicidal activity. These compounds should have high activity, broad spectrum activity against different strains of nematodes and should not be toxic to non-target organisms.

The occurrence of resistances against all commercial anthelmintics seems to be a growing problem in the area of veterinary medicine. Therefore, endoparasiticides with new molecular modes of actions are urgently desired. The new active ingredients should perform with excellent efficacy against a broad spectrum of helminths and nematodes without any adverse toxic effects to the treated vertebratic organism. Endoparasiticides are pharmaceuticals for combat or suppression of endoparasites in animals or humans.

The use of certain N-2-(pyridyl)ethyl-carboxamide derivatives for controlling nematodes is described in WO2007/108483 A1 and EP 2 132 987 A1.

The use of certain carboxamides as parasiticides is described in WO2012/118139 A1 and WO2013/0676230 A1.

Furthermore, certain carboxamides are described as pesticides in WO2013/064518 A1, WO2013/064519 A1, WO2013/064520 A1, WO2013/064521 A1 or as nematicides in WO2013/064460 A1 and WO2013/064461 A1.

SUMMARY

It is an object of the present invention to provide compounds which can be used as nematicides with a satisfactory or improved nematicidal activity, particularly at relatively low application rates, with a high selectivity and high compatibility in crop-plant cultures. Another object of the present invention is to provide compounds which can be used as endoparasiticides with a satisfactory or improved anthelmintic activity against a broad spectrum of helminths and nematodes, particularly at relatively low dosages, without any adverse toxic effects to the treated vertebratic organism.

The present invention relates to a compound of formula (I)

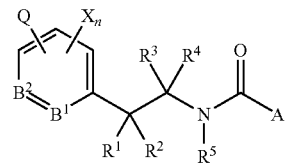

wherein (embodiment 1-1)
$B^1$, $B^2$ represent C—X or N, wherein at least $B^1$ or $B^2$ is N,
n is 0, 1, 2, 3 or 4, limited by the number of available positions in the ring to which a substituent X can be connected,
each X is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino.

Q represents an aromatic or partially saturated or saturated, 5- or 6-membered heterocyclic ring containing one to four heteroatoms chosen from N, S, and O bearing the substituent Ym with m is 0, 1, 2, 3 or 4, limited by the number of available positions in Q to which a substituent Y can be connected, and each Y is independently selected from the group consisting of hydrogen, halogen, nitro, cyano, hydroxy, amino, oxo (=O), —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$- halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino.

$R^1$, $R^2$, $R^3$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^2$ together with the carbon atom to which they are bonded form a 4-, 5- or 6-membered carbocycle and $R^1$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)—phenyl, —S(O)$_2$-phenyl, phenylamino, phenylcarbonylamino, 2,6-dichlorophenyl-carbonylamino, 2-chlorophenyl-carbonylamino and phenyl, or $R^3$ and $R^4$ together with the carbon atom to which they are bonded form a 3-, 4-, 5- or 6-membered carbocycle and $R^1$ and $R^2$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)— phenyl, —S(O)$_2$-phenyl, phenylamino, phenylcarbonylamino, 2,6-dichlorophenyl-carbonylamino, 2-chlorophenyl-carbonylamino and phenyl, or $R^4$ and $R^2$ together with the carbon atom to which they are bonded form a 3-, 4-, 5- or 6-membered non-aromatic carbocycle optionally substituted by substituents selected from the group consisting of one to four $C_1$-$C_8$-alkyl groups and one to four halogen atoms, and $R^1$ and $R^3$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^3$ together with the carbon atom to which they are bonded form a 3-, 4-, 5- or 6-membered non-aromatic carbocycle optionally substituted by substituents selected from the group consisting of one to four $C_1$-$C_8$-alkyl groups and one to four halogen atoms, and $R^2$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, $R^5$ is selected from the group consisting of hydrogen, cyano, —CHO, —OH, $C_1$-$C_6$-alkyl, $C_1$-$C_6$-halogenoalkyl having 1 to 5 halogen atoms, $C_1$-$C_6$-alkoxy, $C_1$-$C_6$-halogenoalkoxy having 1 to 5 halogen atoms, $C_3$-$C_7$-cycloalkyl, $C_3$-$C_7$-halogenocycloalkyl having 1 to 5 halogen atoms, $C_3$-$C_7$-cycloalkyl-$C_1$-$C_6$-alkyl, —CONH($C_1$-$C_6$-alkyl), $C_2$-$C_6$-alkenyl, $C_2$-$C_6$-alkynyl, $C_1$-$C_6$-alkoxy-$C_1$-$C_6$-alkyl, $C_3$-$C_7$-cycloalkyl-$C_1$-$C_6$-alkyl, cyano-$C_1$-$C_6$-alkyl, amino-$C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, $C_1$-$C_6$-alkylcarbonyl, $C_1$-$C_6$-halogenoalkylcarbonyl having 1 to 5 halogen atoms, $C_1$-$C_6$-alkoxycarbonyl, $C_1$-$C_6$-benzyloxycarbonyl, $C_1$-$C_6$-alkoxy-$C_1$-$C_6$-alkylcarbonyl, —S—$C_1$-$C_6$-alkyl, —S—$C_1$-$C_6$-halogenoalkyl having 1 to 5 halogen atoms, —S(O)$_2$—$C_1$-$C_6$-alkyl, and —S(O)$_2$—$C_1$-$C_6$-halogenoalkyl having 1 to 5 halogen atoms, A represents a phenyl group of the formula (A1)

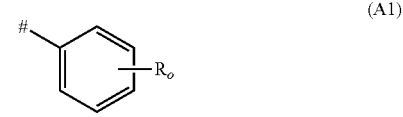

(A1)

wherein o is 0, 1, 2, 3, 4 or 5, and each R is independently selected from the group consisting of halogen, nitro, —OH, NH$_2$, SH, SF$_5$, CHO, OCHO, NHCHO, COOH, cyano, $C_1$-$C_8$-alkyl, $C_1$-$C_8$-halogenoalkyl having 1 to 9 halogen atoms, $C_2$-$C_8$-alkenyl, $C_2$-$C_8$-alkynyl, $C_3$-$C_6$-cycloalkyl, —S—$C_1$-$C_8$-alkyl, —S—$C_1$-$C_8$-halogenoalkyl having 1 to 5 halogen atoms, $C_1$-$C_8$-alkoxy, $C_1$-$C_8$-halogenoalkoxy having 1 to 5 halogen atoms, $C_1$-$C_8$-alkoxy-$C_2$-$C_8$-alkenyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, $C_1$-$C_8$-alkylsulfonamide, —NH($C_1$-$C_8$-alkyl), N($C_1$-$C_8$-alkyl)$_2$, phenyl (optionally substituted by $C_1$-$C_6$-alkoxy) and phenoxy, or two R bonded to adjacent carbon atoms together represent —O(CH$_2$)$_p$O—, wherein p represents 1 or 2, or A represents a heterocycle of the formula (Het-1)

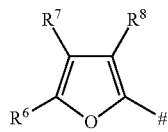
(Het-1)

in which
R⁶ and R⁷ may be the same or different and are selected from the group consisting of hydrogen, halogen, amino, nitro, $C_1$-$C_4$-alkyl and $C_1$-$C_4$-halogenoalkyl having 1 to 5 halogen atoms, and
R⁸ is selected from the group consisting of hydrogen, halogen, nitro, $C_1$-$C_4$-alkyl and $C_1$-$C_4$-halogenoalkyl having 1 to 5 halogen atoms, or
A represents a heterocycle of the formula (Het-2)

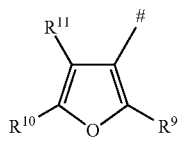
(Het-2)

R⁹ is selected from the group consisting of hydrogen, halogen, $C_1$-$C_4$-alkyl and $C_1$-$C_4$-halogenoalkyl having 1 to 5 halogen atoms, and
R¹⁰ and R¹¹ may be the same or different and are selected from the group consisting of hydrogen, halogen, amino, $C_1$-$C_4$-alkyl, $C_1$-$C_4$-halogenoalkyl having 1 to 5 halogen atoms and phenyl (optionally substituted by halogen or $C_1$-$C_4$-alkyl), or
A represents a heterocycle of the formula (Het-3)

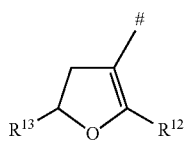
(Het-3)

in which
R¹² is selected from the group consisting of halogen, $C_1$-$C_4$-alkyl and $C_1$-$C_4$-halogenoalkyl having 1 to 5 halogen atoms, and
R¹³ is selected from the group consisting of hydrogen, $C_1$-$C_4$-alkyl and $C_1$-$C_4$-halogenoalkyl having 1 to 5 halogen atoms, or
A represents a heterocycle of the formula (Het-4)

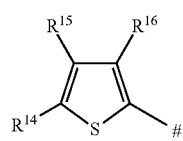
(Het-4)

in which
R¹⁴ and R¹⁵ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)₂—$C_1$-$C_4$-alkyl, phenyl optionally substituted by halogen or $C_1$-$C_4$-alkyl and pyridyl (optionally substituted by halogen or $C_1$-$C_4$-alkyl), and
R¹⁶ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or
A represents a heterocycle of the formula (Het-5)

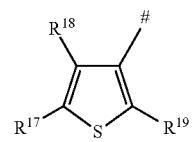
(Het-5)

in which
R¹⁷ and R¹⁸ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
R¹⁹ is selected from the group consisting of hydrogen, halogen, $C_1$-$C_4$-alkyl and $C_1$-$C_4$-halogenoalkyl having 1 to 5 atoms, or
A represents a heterocycle of the formula (Het-6)

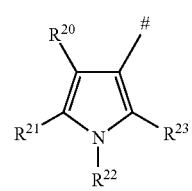
(Het-6)

in which
R²⁰ is selected from the group consisting of hydrogen, halogen, cyano, $C_1$-$C_4$-alkyl and $C_1$-$C_4$-halogenoalkyl having 1 to 5 halogen atoms, and
R²¹ and R²³ may be the same or different and are selected from the group consisting of hydrogen, halogen, $C_1$-$C_4$-alkyl and $C_1$-$C_4$-halogenoalky having 1 to 5 halogen atoms, and
R²² is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxyl-$C_1$-$C_4$-alkyl, —S(O)₂—$C_1$-$C_4$-alkyl, —S(O)₂—N($C_1$-$C_4$-alkyl)₂, $C_1$-$C_6$-alkylcarbonyl, —S(O)₂-phenyl (optionally substituted by halogen or $C_1$-$C_4$-alkyl) and benzoyl (optionally substituted by halogen or $C_1$-$C_4$-alkyl), or
A represents a heterocycle of the formula (Het-7)

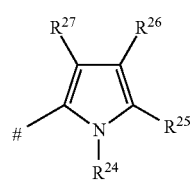
(Het-7)

in which
$R^{24}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxy-$C_1$-$C_4$-alkyl, —S(O)$_2$—$C_1$-$C_4$-alkyl, —S(O)$_2$—N($C_1$-$C_4$-alkyl)$_2$, $C_1$-$C_6$-alkylcarbonyl, —S(O)$_2$-phenyl (optionally substituted by halogen or $C_1$-$C_4$-alkyl) and benzoyl (optionally substituted by halogen or a $C_1$-$C_4$-alkyl), and
$R^{25}$, $R^{26}$ and $R^{27}$ may be the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or A represents a heterocycle of the formula (Het-8)

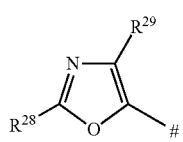

(Het-8)

in which
$R^{28}$ is selected from the group consisting of hydrogen and $C_1$-$C_4$-alkyl, and
$R^{29}$ is selected from the group consisting of halogen, $C_1$-$C_4$-alkyl and $C_1$-$C_4$-halogenoalkyl having 1 to 5 halogen atoms, or A represents a heterocycle of the formula (Het-9)

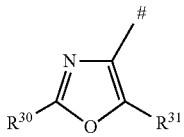

(Het-9)

in which
$R^{30}$ is selected from the group consisting of hydrogen and $C_1$-$C_4$-alkyl, and
$R^{31}$ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or A represents a heterocycle of the formula (Het-10)

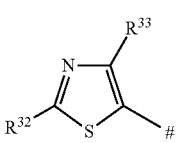

(Het-10)

in which
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and
$R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy having 1 to 9 halogen atoms, amino, substituted or unsubstituted $C_1$-$C_5$-alkylamino or substituted or unsubstituted di-($C_1$-$C_5$-alkyl)amino, or A represents a heterocycle of the formula (Het-11)

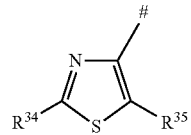

(Het-11)

in which
$R^{34}$ is selected from the group consisting of hydrogen, halogen, amino, cyano, $C_1$-$C_4$-alkylamino, di-($C_1$-$C_4$-alkyl)amino, $C_1$-$C_4$-alkyl and $C_1$-$C_4$-halogenoalkyl having 1 to 5 halogen atoms, and
$R^{35}$ is selected from the group consisting of halogen, $C_1$-$C_4$-alkyl and $C_1$-$C_4$-halogenoalkyl having 1 to 5 halogen atoms, or A represents a heterocycle of the formula (Het-12)

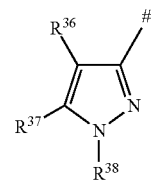

(Het-12)

in which
$R^{36}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl, and
$R^{37}$ is selected from the group consisting of hydrogen, halogen, cyano, nitro, $C_1$-$C_4$-alkyl, $C_1$-$C_4$-alkoxy, —S—$C_1$-$C_4$-alkyl, —S(O)—$C_1$-$C_4$-alkyl, and —S(O)$_2$—$C_1$-$C_4$-alkyl, and
$R^{38}$ is selected from the group consisting of hydrogen, phenyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or A represents a heterocycle of the formula (Het-13)

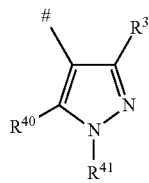

(Het-13)

in which
$R^{39}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, S(O)—$C_1$-$C_4$-alkyl, —S(O)$_2$—$C_1$-$C_4$-alkyl, —S—$C_1$-$C_4$-halogenoalkyl having 1 to 5 atoms, aminocarbonyl and aminocarbonyl-$C_1$-$C_4$-alkyl, and
$R^{40}$ is selected from the group consisting of hydrogen, halogen, cyano, $C_1$-$C_4$-alkyl, $C_1$-$C_4$-alkoxy, $C_1$-$C_1$-halogenoalkoxy having 1 to 5 halogen atoms, —S—$C_1$-$C_4$-alkylS(O)—$C_1$-$C_4$-alkyl, and —S(O)$_2$—$C_1$-$C_4$-alkyl, and
$R^{41}$ is selected from the group consisting of hydrogen, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl, $C_1$-$C_4$-halogenoalkoxy-$C_1$-$C_4$-alkyl having 1 to 5 halogen atoms and phenyl (optionally substituted by halogen, $C_1$-$C_4$-alkyl, $C_1$-$C_4$-alkoxy-$C_1$-$C_4$-alkyl or nitro), or
A represents a heterocycle of the formula (Het-14)

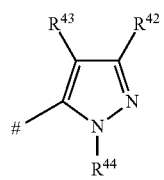

(Het-14)

in which
$R^{42}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, S(O)—$C_1$-$C_4$-alkyl, —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl, and
$R^{43}$ is selected from the group consisting of hydrogen, halogen, cyano, $C_1$-$C_4$-alkyl, $C_1$-$C_4$-alkoxy, —S—$C_1$-$C_4$-alkyl, S(O)—$C_1$-$C_4$-alkyl, —S(O)$_2$—$C_1$-$C_4$-alkyl, and $C_1$-$C_4$-halogenoalkyl having 1 to 5 halogen atoms, and
$R^{44}$ is selected from the group consisting of hydrogen, phenyl, benzyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or
A represents a heterocycle of the formula (Het-15)

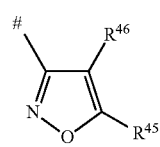

(Het-15)

in which
$R^{45}$ and $R^{46}$ may be the same or different and are selected from the group consisting of hydrogen, halogen, $C_1$-$C_4$-alkyl and $C_1$-$C_4$-halogenoalkyl having 1 to 5 halogen atoms, or
A represents a heterocycle of the formula (Het-16)

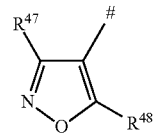

(Het-16)

in which
$R^{47}$ and $R^{48}$ may be the same or different and are selected from the group consisting of hydrogen, halogen, $C_1$-$C_4$-alkyl, $C_1$-$C_4$-halogenoalkyl having 1 to 5 halogen atoms, phenyl (optionally substituted by halogen or a $C_1$-$C_4$-alkyl), and heterocyclyl like pyridyl, pyrimidinyl and thiadiazolyl (each optionally substituted by halogen or $C_1$-$C_4$-alkyl), or
A represents a heterocycle of the formula (Het-17)

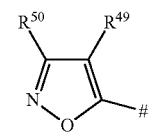

(Het-17)

in which
$R^{49}$ and $R^{50}$ may be the same or different and are selected from the group consisting of hydrogen, halogen, $C_1$-$C_4$-alkyl and $C_1$-$C_4$-halogenoalkyl having 1 to 5 halogen atoms, or
A represents a heterocycle of the formula (Het-18)

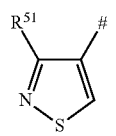

(Het-18)

in which
$R^{51}$ is selected from the group consisting of halogen, $C_1$-$C_4$-alkyl and $C_1$-$C_4$-halogenoalkyl having 1 to 5 halogen atoms, or
A represents a heterocycle of the formula (Het-19)

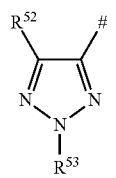

(Het-19)

in which
$R^{52}$ is selected from the group consisting of halogen, $C_1$-$C_4$-alkyl and $C_1$-$C_4$-halogenoalkyl having 1 to 5 halogen atoms, and $R^{53}$ is selected from the group consisting of hydrogen, $C_1$-$C_4$-alkyl, $C_1$-$C_4$-halogenoalkyl having 1 to 5 halogen atoms and phenyl (optionally substituted by halogen or $C_1$-$C_4$-alkyl), or A represents a heterocycle of the formula (Het-20)

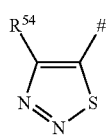

(Het-20)

in which $R^{54}$ is selected from the group consisting of halogen, $C_1$-$C_4$-alkyl and $C_1$-$C_4$-halogenoalkyl having 1 to 5 halogen atoms, or A represents a heterocycle of the formula (Het-21)

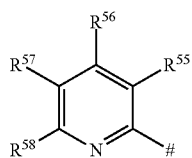

(Het-21)

in which $R^{55}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to S halogen atoms, —S(O)—$C_1$-$C_4$-alkyl and —S(O)$_2$—$C_1$-$C_4$-alkyl, or A represents a heterocycle of the formula (Het-22)

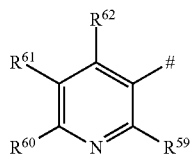

(Het-22)

in which $R^{59}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, S(O)—$C_1$-$C_4$-alkyl, —S(O)$_2$—$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), and $R^{60}$, $R^{61}$ and $R^{62}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine optionally substituted by halogen or $C_1$-$C_4$-alkyl, and thienyl (optionally substituted by halogen or a $C_1$-$C_4$-alkyl), or A represents a heterocycle of the formula (Het-23)

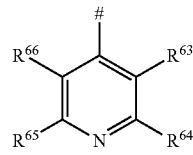

(Het-23)

in which $R^{63}$, $R^{64}$, $R^{65}$ and $R^{66}$, which may be the same or different, are selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-24)

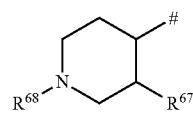

(Het-24)

in which $R^{67}$ is selected from the group consisting of hydrogen, halogen, $C_1$-$C_4$-alkyl and $C_1$-$C_4$-halogenoalkyl having 1 to 5 halogen atoms, and $R^{68}$ is selected from the group consisting of hydrogen, $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms), and heterocyclyl like pyridyl and pyrimidinyl (each optionally substituted by halogen, $C_1$-$C_4$-alkyl, $C_1$-$C_4$-halogenoalkyl having 1 to 5 halogen atoms), or A represents a heterocycle of the formula (Het-25)

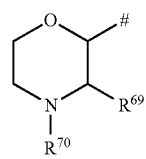

(Het-25)

in which $R^{69}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{70}$ is selected from the group consisting of hydrogen, $C_1$-$C_4$-alkyl, $C_1$-$C_4$-halogenoalkyl having 1 to 5 halogen atoms, and benzyl, or A represents a heterocycle of the formula (Het-26)

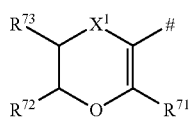
(Het-26)

in which
X$^1$ is selected from the group consisting of sulphur, —SO—, —SO$_2$— and —CH$_2$—, and
R$^{71}$ is selected from the group consisting of C$_1$-C$_4$-alkyl and C$_1$-C$_4$-halogenoalkyl having 1 to 5 halogen atoms, and
R$^{72}$ and R$^{73}$ may be the same or different and are selected from the group consisting of hydrogen and C$_1$-C$_4$-alkyl, or
A represents a heterocycle of the formula (Het-27)

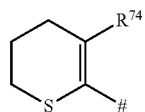
(Het-27)

in which
R$^{74}$ is selected from the group consisting of C$_1$-C$_4$-alkyl and C$_1$-C$_4$-halogenoalkyl having 1 to 5 halogen atoms, or
A represents a heterocycle of the formula (Het-28)

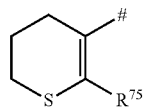
(Het-28)

in which
R$^{75}$ is selected from the group consisting of C$_1$-C$_4$-alkyl and C$_1$-C$_4$-halogenoalkyl having 1 to 5 halogen atoms, or
A represents a heterocycle of the formula (Het-29)

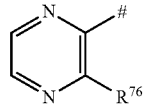
(Het-29)

in which
R$^{76}$ is selected from the group consisting of hydrogen, halogen, C$_1$-C$_4$-alkyl and C$_1$-C$_4$-halogenoalkyl having 1 to 5 halogen atoms.

In formulae (Het-1) to (Het-29) #depicts the bond which connects A to the C(O)NR$^5$-moiety in the compounds of formula (I). In general, in the present application #depicts the connecting bond of the structural element, unless otherwise indicated.

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

The invention also relates to salts. N-oxides, metal complexes and metalloid complexes of compounds of formula (I) and the uses thereof.

Compounds of the present invention can also exist in one or more geometric isomer forms depending on the number of double bonds in the compound, especially all syn/anti (or cis/trans) isomers and to all possible syn/anti (or cis/trans) mixtures. The invention thus relates equally to all geometric isomers and to all possible mixtures, in all proportions. The geometric isomers can be separated according to general methods, which are known per se by the man ordinary skilled in the art.

Compounds of formula (I) may be found in its tautomeric form resulting from the shift of the proton of a hydroxy, sulfanyl or amino group. Such tautomeric forms of such compounds are also part of the present invention. More generally speaking, all tautomeric forms of compounds of formula (I), as well as the tautomeric forms of the compounds which can optionally be used as intermediates in the preparation processes and which will be defined in the description of these processes, are also part of the present invention.

Further, this invention is directed to compositions comprising compounds of the invention and their use for controlling a nematode. This invention also provides a composition comprising a compound of formula (I), or an N-oxide, or a salt thereof, and at least one additional component selected from the group consisting of surfactants, solid diluents and liquid diluents. In one embodiment, this invention provides such a composition which further comprises at least one additional active ingredient, preferably a mixing partner as described below.

Further, this invention is directed to the use of compounds and/or compositions of the invention for controlling animal pests, especially nematodes, in crop protection or in the veterinary sector. This invention provides also a method for controlling a nematode comprising contacting the nematode or its environment with a biologically effective amount of a compound of formula (I), or an N-oxide, or a salt thereof (e.g., as a composition described herein). This invention also relates to such method wherein the nematode or its environment is contacted with a composition comprising a biologically effective amount of a compound of Formula (I), an N-oxide or a salt thereof, and at least one additional component selected from the group consisting of surfactants, solid diluents and liquid diluents, said composition optionally further comprising a biologically effective amount of at least one additional active ingredient, preferably a mixing partner as described below. In one embodiment, the methods according to the invention do not comprise methods for treatment of the human or animal body by surgery or therapy and diagnostic methods practised on the human or animal body.

This invention also provides a method for protecting a seed from a nematode comprising contacting the seed with a biologically effective amount of a compound of formula (I), or an N-oxide, or a salt thereof (e.g., as a composition described herein). This invention is also related to a seed obtained by said method.

DETAILED DESCRIPTION OF A PREFERRED EMBODIMENT

As used herein, the terms "comprises". "comprising", "includes", "including". "has". "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than 10 one double bond such as 1,3- and 1,4-cyclohexadienyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_2CCl_2$. The terms "haloalkoxy", "haloalkenyl", "haloalkynyl", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$.

The chemical abbreviation C(O) as used herein represents a carbonyl moiety. For example, $C(O)CH_3$ represents an acetyl group. The chemical abbreviations $CO_2$ and C(O)O as used herein represent an ester moiety. For example, $CO_2Me$ and C(O)OMe represent a methyl ester. CHO represents an aldehyde moiety.

"OCN" means $-O-C\equiv N$, and "SCN" means $-S-C\equiv N$.

The total number of carbon atoms in a substituent group is indicated by the "Ci-Cj" prefix where i and j are numbers from 1 to 14, $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can exceed 1, said substituents (when they exceed 1) are independently selected from the group of defined substituents, e.g. n=0, 1, 2, 3 or 4. When a group contains a substituent which can be hydrogen, for example $R^2$ or $R^3$, then when this substituent is taken as hydrogen, it is recognized that this is equivalent to said group being unsubstituted.

Unless otherwise indicated, a "ring" or "ring system" as a component of formula (I) is carbocyclic or heterocyclic. The term "ring system" denotes two or more fused rings. The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "heterocyclic ring system" denotes a ring system in which at least one ring of the ring system is a heterocyclic ring. Unless otherwise indicated, heterocyclic rings and ring systems can be attached through any available carbon or nitrogen by replacement of a hydrogen on said carbon or nitrogen.

As used herein, the following definitions shall apply unless otherwise indicated. The term "optionally substituted" is used interchangeably with the phrase "substituted or unsubstituted" or with the term "(un)substituted". The expression "optionally substituted with 1 to 4 substituents" means that no substituent is present (i.e. unsubstituted) or that 1, 2, 3 or 4 substituents are present (limited by the number of available bonding positions). Unless otherwise indicated, an optionally substituted group may have a substituent at each substitutable position of the group, and each substitution is independent of the other.

In an individual embodiment (embodiment 1-2), the structural elements in the compound of formula (I) are defined as follows:

$B^1$, $B^2$ represent C—X or N, wherein at least $B^1$ or $B^2$ is N, n is 0, 1, 2, 3 or 4, limited by the number of available positions in the ring to which a substituent X can be connected, each X is independently selected from the group consisting of hydrogen, halogen, nitro, cyano, hydroxy, amino, —SH, —$SF_5$, —CHO, —OCHO, —NHCHO, —COOH, —$CONH_2$, —CONH(OH), —$OCONH_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino. $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, ($C_1$-$C_6$-alkoxyimino)-$C_1$-$C_6$-alkyl, ($C_2$-$C_6$-alkenyloxy imino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, Q represents an aromatic or partially saturated or saturated, 6-membered heterocyclic ring containing one to four heteroatoms chosen from N, S, and O bearing the substituent Ym with m is 0, 1, 2, 3 or 4, limited by the number of available positions in Q to which a substituent Y can be connected, and each Y is independently selected from the group consisting of hydrogen, halogen, nitro, cyano, hydroxy, amino, oxo (=O), —SH, —$SF_5$, —CHO, —OCHO, —NHCHO, —COOH, —$CONH_2$, —CONH(OH), —$OCONH_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl. $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —$CH_2$—S—$C_1$-$C_8$-alkyl, —$CH_2$—S(O)—$C_1$-$C_8$-alkyl, —$CH_2$—S(O)$_2$—$C_1$-$C_8$-alkyl, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)$C_1$-$C_6$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —SH, —CHO, —OCHO, —NHCHO, —COOH, —$CONH_2$, —CONH(OH), —$OCONH_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$-$C_1$-$C_6$-halogenoalkyl having 1 to 5 halogen atoms, benzyl, benzyloxy, —S-benzyl, —S(O)— benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^2$ together with the carbon atom to which they are bonded form a 4-, 5- or 6-membered carbocycle and $R^1$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-C$_1$-C$_6$-alkyl group, C$_1$-C$_6$-alkyl, C$_2$-C$_6$-alkenyl, C$_2$-C$_6$-alkynyl, C$_1$-C$_6$-alkylamino, di-(C$_1$-C$_6$-alkyl)amino, C$_1$-C$_6$-alkoxy, hydroxy-C$_1$-C$_4$-alkyl, C$_1$-C$_4$-alkoxy-C$_1$-C$_3$-alkyl, C$_1$-C$_6$-halogenoalkyl having 1 to 5 halogen atoms, C$_1$-C$_6$-halogenoalkoxy having 1 to 5 halogen atoms, C$_2$-C$_6$-alkenyloxy, C$_2$-C$_6$-halogenoalkenyloxy having 1 to 5 halogen atoms, C$_3$-C$_6$-alkynyloxy, C$_3$-C$_6$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_6$-alkyl, C$_3$-C$_6$-halogenocycloalkyl-C$_1$-C$_6$-alkyl having 1 to 5 halogen atoms, C$_1$-C$_6$-alkylcarbonyl, C$_1$-C$_6$-halogenoalkylcarbonyl having 1 to 5 halogen atoms, —CONH(C$_1$-C$_6$-alkyl), —CON(C$_1$-C$_6$-alkyl)$_2$, —CONH(OC$_1$-C$_6$-alkyl), —CON(OC$_1$-C$_6$-alkyl)(C$_1$-C$_6$-alkyl), C$_1$-C$_6$-alkoxycarbonyl, a C$_1$-C$_6$-halogenoalkoxycarbonyl having 1 to 5 halogen atoms, —OC(O)—C$_1$-C$_6$-alkyl, —OC(O)—C$_1$-C$_6$-halogenoalkyl having 1 to 5 halogen atoms, —NHC(O)—C$_1$-C$_6$-alkyl, —NHC(O)—C$_1$-C$_6$-halogenoalkyl having 1 to 5 halogen atoms, —OCONH(C$_1$-C$_6$-alkyl), —OCON(C$_1$-C$_6$-alkyl)$_2$, —OCONH(OC$_1$-C$_6$-alkyl), OCO(OC$_1$-C$_6$-alkyl), —S—C$_1$-C$_6$-alkyl, —S—C$_1$-C$_6$-halogenoalkyl having 1 to 5 halogen atoms, —S(O)—C$_1$-C$_6$-alkyl, —S(O)—C$_1$-C$_6$-halogenoalkyl having 1 to 5 halogen atoms, —S(O)$_2$ —C$_1$-C$_6$-alkyl, —S(O)$_2$—C$_1$-C$_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^3$ and R$^4$ together with the carbon atom to which they are bonded form a 3-, 4-, 5- or 6-membered carbocycle and R$^1$ and R$^2$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-C$_1$-C$_6$-alkyl group, C$_1$-C$_6$-alkyl, C$_2$-C$_6$-alkenyl, C$_2$-C$_6$-alkynyl, C$_1$-C$_6$-alkylamino, di-(C$_1$-C$_6$-alkyl)amino, C$_1$-C$_6$-alkoxy, hydroxy-C$_1$-C$_4$-alkyl, C$_1$-C$_4$-alkoxy-C$_1$-C$_3$-alkyl, C$_1$-C$_6$-halogenoalkyl having 1 to 5 halogen atoms, C$_1$-C$_6$-halogenoalkoxy having 1 to 5 halogen atoms, C$_2$-C$_6$-alkenyloxy, C$_2$-C$_6$-halogenoalkenyloxy having 1 to 5 halogen atoms, C$_3$-C$_6$-alkynyloxy, C$_3$-C$_6$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_6$-alkyl, C$_3$-C$_6$-halogenocycloalkyl-C$_1$-C$_6$-alkyl having 1 to 5 halogen atoms, C$_1$-C$_6$-alkylcarbonyl, C$_1$-C$_6$-halogenoalkylcarbonyl having 1 to 5 halogen atoms, —CONH(C$_1$-C$_6$-alkyl), —CON(C$_1$-C$_6$-alkyl)$_2$, —CONH(OC$_1$-C$_6$-alkyl), —CON(OC$_1$-C$_6$-alkyl)(C$_1$-C$_6$-alkyl), C$_1$-C$_6$-alkoxycarbonyl, a C$_1$-C$_6$-halogenoalkoxycarbonyl having 1 to 5 halogen atoms, —OC(O)—C$_1$-C$_6$-alkyl, —OC(O)—C$_1$-C$_6$-halogenoalkyl having 1 to 5 halogen atoms, —NHC(O)—C$_1$-C$_6$-alkyl, —NHC(O)—C$_1$-C$_6$-halogenoalkyl having 1 to 5 halogen atoms, —OCONH(C$_1$-C$_6$-alkyl), —OCON(C$_1$-C$_6$-alkyl)$_2$, —OCONH(OC$_1$-C$_6$-alkyl), OCO(OC$_1$-C$_6$-alkyl), —S—C$_1$-C$_6$-alkyl, —S—C$_1$-C$_6$-halogenoalkyl having 1 to 5 halogen atoms, —S(O)—C$_1$-C$_6$-alkyl, —S(O)—C$_1$-C$_6$-halogenoalkyl having 1 to 5 halogen atoms, —S(O)$_2$ C$_1$-C$_6$-alkyl, —S(O)$_2$—C$_1$-C$_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^4$ and R$^2$ together with the carbon atom to which they are bonded form a 3-, 4-, 5- or 6-membered non-aromatic carbocycle optionally substituted by substituents selected from the group consisting of one to four C$_1$-C$_8$-alkyl groups and one to four halogen atoms, and R$^1$ and R$^3$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-C$_1$-C$_6$-alkyl group, C$_1$-C$_6$-alkyl, C$_2$-C$_6$-alkenyl, C$_2$-C$_6$-alkynyl, C$_1$-C$_6$-alkylamino, di-(C$_1$-C$_6$-alkyl)amino, C$_1$-C$_6$-alkoxy, hydroxy-C$_1$-C$_4$-alkyl, C$_1$-C$_4$-alkoxy-C$_1$-C$_3$-alkyl, C$_1$-C$_6$-halogenoalkyl having 1 to 5 halogen atoms, C$_1$-C$_6$-halogenoalkoxy having 1 to 5 halogen atoms, C$_2$-C$_6$-alkenyloxy, C$_2$-C$_6$-halogenoalkenyloxy having 1 to 5 halogen atoms, C$_3$-C$_6$-alkynyloxy, C$_3$-C$_6$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_6$-alkyl, C$_3$-C$_6$-halogenocycloalkyl-C$_1$-C$_6$-alkyl having 1 to 5 halogen atoms, C$_1$-C$_6$-alkylcarbonyl, C$_1$-C$_6$-halogenoalkylcarbonyl having 1 to 5 halogen atoms, —CONH(C$_1$-C$_6$-alkyl), —CON(C$_1$-C$_6$-alkyl)$_2$, —CONH(OC$_1$-C$_6$-alkyl), —CON(OC$_1$-C$_6$-alkyl)(C$_1$-C$_6$-alkyl), C$_1$-C$_6$-alkoxycarbonyl, a C$_1$-C$_6$-halogenoalkoxycarbonyl having 1 to 5 halogen atoms, —OC(O)—C$_1$-C$_6$-alkyl, —OC(O)—C$_1$-C$_6$-halogenoalkyl having 1 to 5 halogen atoms, —NHC(O)—C$_1$-C$_6$-alkyl, —NHC(O)—C$_1$-C$_6$-halogenoalkyl having 1 to 5 halogen atoms, —OCONH(C$_1$-C$_6$-alkyl), —OCON(C$_1$-C$_6$-alkyl)$_2$, —OCONH(OC$_1$-C$_6$-alkyl), OCO(OC$_1$-C$_6$-alkyl), —S—C$_1$-C$_6$-alkyl, —S—C$_1$-C$_6$-halogenoalkyl having 1 to 5 halogen atoms, —S(O)—C$_1$-C$_6$-alkyl, —S(O)—C$_1$-C$_6$-halogenoalkyl having 1 to 5 halogen atoms, —S(O)$_2$ —C$_1$-C$_6$-alkyl, —S(O)$_2$—C$_1$-C$_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^1$ and R$^3$ together with the carbon atom to which they are bonded form a 3-, 4-, 5- or 6-membered non-aromatic carbocycle optionally substituted by substituents selected from the group consisting of one to four C$_1$-C$_8$-alkyl groups and one to four halogen atoms, and R$^2$ and R$^4$ are the same or different and are selected from the group consisting of hydrogen, halogen, cyano, hydroxy, amino. —SH, —CHO, —OCHO, —NHCHO, —COOH, —CONH$_2$, —CONH(OH), —OCONH$_2$, a (hydroxyimino)-C$_1$-C$_6$-alkyl group, C$_1$-C$_6$-alkyl, C$_2$-C$_6$-alkenyl, C$_2$-C$_6$-alkynyl, C$_1$-C$_6$-alkylamino, di-(C$_1$-C$_6$-alkyl)amino, C$_1$-C$_6$-alkoxy, hydroxy-C$_1$-C$_4$-alkyl, C$_1$-C$_4$-alkoxy-C$_1$-C$_3$-alkyl, C$_1$-C$_6$-halogenoalkyl having 1 to 5 halogen atoms, C$_1$-C$_6$-halogenoalkoxy having 1 to 5 halogen atoms, C$_2$-C$_6$-alkenyloxy, C$_2$-C$_6$-halogenoalkenyloxy having 1 to 5 halogen atoms, C$_3$-C$_6$-alkynyloxy, C$_3$-C$_6$-halogenoalkynyloxy having 1 to 5 halogen atoms, C$_3$-C$_6$-cycloalkyl, C$_3$-C$_6$-halogenocycloalkyl having 1 to 5 halogen atoms, C₃-C₆-cycloalkyl-C₁-C₆-alkyl, C₃-C₆-halogenocycloalkyl-C₁-C₆-alkyl having 1 to 5 halogen atoms, C₁-C₆-alkylcarbonyl, C₁-C₆-halogenoalkylcarbonyl having 1 to 5 halogen atoms, —CONH(C₁-C₆-alkyl), —CON(C₁-C₆-alkyl)₂, —CONH(OC₁-C₆-alkyl), —CON(OC₁-C₆-alkyl)(C₁-C₆-alkyl), C₁-C₆-alkoxycarbonyl, a C₁-C₆-halogenoalkoxycarbonyl having 1 to 5 halogen atoms, —OC(O)—C₁-C₆-alkyl, —OC(O)—C₁-C₆-halogenoalkyl having 1 to 5 halogen atoms, —NHC(O)—C₁-C₆-alkyl, —NHC(O)—C₁-C₆-halogenoalkyl having 1 to 5 halogen atoms, —OCONH(C₁-C₆-alkyl), —OCON(C₁-C₆-alkyl)₂, —OCONH(OC₁-C₆-alkyl), OCO(OC₁-C₆-alkyl), —S—C₁-C₆-alkyl, —S—C₁-C₆-halogenoalkyl having 1 to 5 halogen atoms, —S(O)—C₁-C₆-alkyl, —S(O)C₁-C₆-halogenoalkyl having 1 to 5 halogen atoms, —S(O)₂—C₁-C₆-alkyl, —S(O)₂—C₁-C₆-halogenoalkyl having 1 to 5 halogen atoms, benzyl, benzyloxy, —S-benzyl, —S(O)-benzyl, —S(O)₂-benzyl, benzylamino, phenoxy, —S-phenyl, —S(O)-phenyl, —S(O)₂-phenyl, phenylamino, phenylcarbonylamino, 2,6-dichlorophenyl-carbonylamino, 2-chlorophenyl-carbonylamino and phenyl.

$R^5$ is selected from the group consisting of hydrogen, cyano, —CHO, —OH, C₁-C₆-alkyl, C₁-C₆-halogenoalkyl having 1 to 5 halogen atoms, C₁-C₆-alkoxy, C₁-C₆-halogenoalkoxy having 1 to 5 halogen atoms, C₃-C₇-cycloalkyl, C₃-C₇-halogenocycloalkyl having 1 to 5 halogen atoms, C₃-C₇-cycloalkyl-C₁-C₆-alkyl, —CONH(C₁-C₆-alkyl), C₂-C₆-alkenyl, C₂-C₆-alkynyl, C₁-C₆-alkoxy-C₁-C₆-alkyl, C₃-C₇-cycloalkyl-C₁-C₆-alkyl, cyano-C₁-C₆-alkyl, amino-C₁-C₆-alkyl, C₁-C₆-alkylamino-C₁-C₆-alkyl, di-(C₁-C₆-alkyl)amino-C₁-C₆-alkyl, C₁-C₆-alkylcarbonyl, C₁-C₆-halogenoalkylcarbonyl having 1 to 5 halogen atoms, C₁-C₆-alkoxycarbonyl, C₁-C₆-benzyloxycarbonyl, C₁-C₆-alkoxy-C₁-C₆-alkylcarbonyl, —S—C₁-C₆-alkyl, —S—C₁-C₆-halogenoalkyl having 1 to 5 halogen atoms, —S(O)₂—C₁-C₆-alkyl, and —S(O)—C₁-C₆-halogenoalkyl having 1 to 5 halogen atoms, A represents a phenyl group of the formula (A1)

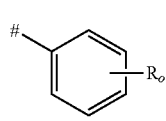

(A1)

wherein
o is 0, 1, 2, 3.4 or 5, and
each R is independently selected from the group consisting of halogen, nitro, —OH, NH₂, SH, SF₅, CHO, OCHO, NHCHO, COOH, cyano, C₁-C₈-alkyl, C₁-C₈-halogenoalkyl having 1 to 9 halogen atoms, C₂-C₈-alkenyl, C₂-C₈-alkynyl, C₃-C₆-cycloalkyl, —S—C₁-C₈-alkyl, —S—C₁-C₈-halogenoalkyl having 1 to 5 halogen atoms, C₁-C₈-alkoxy, C₁-C₈-halogenoalkoxy having 1 to 5 halogen atoms, C₁-C₈-alkoxy-C₁-C₈-alkenyl. C₁-C₈-alkoxycarbonyl, C₁-C₈-halogenoalkoxycarbonyl having 1 to 5 halogen atoms, C₁-C₈-alkylcarbonyloxy, C₁-C₈-halogenoalkylcarbonyloxy having 1 to 5 halogen atoms, —S(O)—C₁-C₈-alkyl, —S(O)—C₁-C₈-halogenoalkyl having 1 to 5 halogen atoms, —S(O)₂—C₁-C₈-alkyl, —S(O)₂—C₁-C₈-halogenoalkyl having 1 to 5 halogen atoms, C₁-C₈-alkylsulfonamide, —NH(C₁-C₈-alkyl), N(C₁-C₈-alkyl)₂, phenyl (optionally substituted by C₁-C₆-alkoxy) and phenoxy, or two R bonded to adjacent carbon atoms together represent —O(CH₂)ₚO—, wherein p represents 1 or 2, or A represents a heterocycle of the formula (Het-1)

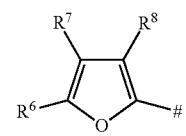

(Het-1)

in which
$R^6$ and $R^7$ may be the same or different and are selected from the group consisting of hydrogen, halogen, amino, nitro, C₁-C₄-alkyl and C₁-C₄-halogenoalkyl having 1 to 5 halogen atoms, and
$R^8$ is selected from the group consisting of hydrogen, halogen, nitro, C₁-C₄-alkyl and C₁-C₄-halogenoalkyl having 1 to 5 halogen atoms, or A represents a heterocycle of the formula (Het-2)

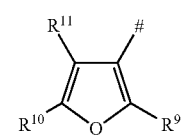

(Het-2)

in which
$R^9$ is selected from the group consisting of hydrogen, halogen, C₁-C₄-alkyl and C₁-C₄-halogenoalkyl having 1 to 5 halogen atoms, and
$R^{10}$ and $R^{11}$ may be the same or different and are selected from the group consisting of hydrogen, halogen, amino, C₁-C₄-alkyl, C₁-C₄-halogenoalkyl having 1 to 5 halogen atoms and phenyl (optionally substituted by halogen or C₁-C₄-alkyl), or A represents a heterocycle of the formula (Het-3)

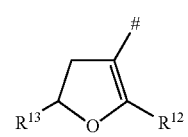

(Het-3)

in which
$R^{12}$ is selected from the group consisting of halogen, C₁-C₄-alkyl and C₁-C₄-halogenoalkyl having 1 to 5 halogen atoms, and
$R^{13}$ is selected from the group consisting of hydrogen, C₁-C₄-alkyl and C₁-C₄-halogenoalkyl having 1 to 5 halogen atoms, or A represents a heterocycle of the formula (Het-4)

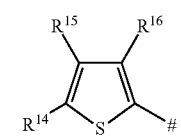

(Het-4)

in which
$R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl optionally substituted by halogen or $C_1$-$C_4$-alkyl and pyridyl (optionally substituted by halogen or $C_1$-$C_4$-alkyl), and
$R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or
A represents a heterocycle of the formula (Het-5)

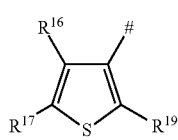
(Het-5)

in which
$R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
$R^{19}$ is selected from the group consisting of hydrogen, halogen, $C_1$-$C_4$-alkyl and $C_1$-$C_4$-halogenoalkyl having 1 to 5 atoms, or
A represents a heterocycle of the formula (Het-6)

(Het-6)

in which
$R^{20}$ is selected from the group consisting of hydrogen, halogen, cyano, $C_1$-$C_4$-alkyl and $C_1$-$C_4$-halogenoalkyl having 1 to 5 halogen atoms, and
$R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and
$R^{22}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxyl-$C_1$-$C_4$-alkyl, —S(O)$_2$—$C_1$-$C_4$-alkyl. —S(O)$_2$—N($C_1$-$C_4$-alkyl)$_2$, $C_1$-$C_6$-alkylcarbonyl, —S(O)$_2$-phenyl (optionally substituted by halogen or $C_1$-$C_4$-alkyl) and benzoyl (optionally substituted by halogen or $C_1$-$C_4$-alkyl), or
A represents a heterocycle of the formula (Het-7)

(Het-7)

in which
$R^{24}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxy-$C_1$-$C_4$-alkyl, —S(O)$_2$$C_1$-$C_4$-alkyl, —S(O)$_2$—N($C_1$-$C_4$-alkyl)$_2$, $C_1$-$C_6$-alkylcarbonyl, —S(O)$_2$-phenyl (optionally substituted by halogen or $C_1$-$C_4$-alkyl) and benzoyl (optionally substituted by halogen or a $C_1$-$C_4$-alkyl), and
$R^{25}$, $R^{26}$ and $R^{27}$ may be the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or
A represents a heterocycle of the formula (Het-8)

(Het-8)

in which
$R^{28}$ is selected from the group consisting of hydrogen and $C_1$-$C_4$-alkyl, and
$R^{29}$ is selected from the group consisting of halogen, $C_1$-$C_4$-alkyl and $C_1$-$C_4$-halogenoalkyl having 1 to 5 halogen atoms, or
A represents a heterocycle of the formula (Het-9)

(Het-9)

in which
$R^{30}$ is selected from the group consisting of hydrogen and $C_1$-$C_4$-alkyl, and
$R^{31}$ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or
A represents a heterocycle of the formula (Het-10)

(Het-10)

in which
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and
$R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy having 1 to 9 halogen atoms, amino, substituted or unsubstituted $C_1$-$C_5$-alkylamino or substituted or unsubstituted di-($C_1$-$C_5$-alkyl)-amino, or A represents a heterocycle of the formula (Het-11)

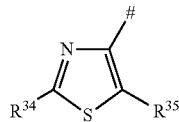

in which
R$^{34}$ is selected from the group consisting of hydrogen, halogen, amino, cyano, C$_1$-C$_4$-alkylamino, di-(C$_1$-C$_4$-alkyl)amino, C$_1$-C$_4$-alkyl and C$_1$-C$_4$-halogenoalkyl having 1 to 5 halogen atoms, and R$^{35}$ is selected from the group consisting of halogen, C$_1$-C$_4$-alkyl and C$_1$-C$_4$-halogenoalkyl having 1 to 5 halogen atoms, or A represents a heterocycle of the formula (Het-12)

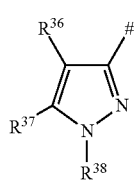

in which
R$^{36}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, —S(O)—C$_1$-C$_4$-alkyl, —S(O)$_2$—C$_1$-C$_4$-alkyl, —S—C$_1$-C$_4$-halogenoalkyl having 1 to 5 halogen atoms, aminocarbonyl and aminocarbonyl-C$_1$-C$_4$-alkyl, and R$^{37}$ is selected from the group consisting of hydrogen, halogen, cyano, nitro, C$_1$-C$_4$-alkyl, C$_1$-C$_4$-alkoxy, —S—C$_1$-C$_4$-alkyl, —S(O)—C$_1$-C$_4$-alkyl, and —S(O)$_2$—C$_1$-C$_4$-alkyl, and R$^{38}$ is selected from the group consisting of hydrogen, phenyl, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl and C$_1$-C$_4$-halogenoalkoxy-C$_1$-C$_4$-alkyl having 1 to 5 halogen atoms, or A represents a heterocycle of the formula (Het-13)

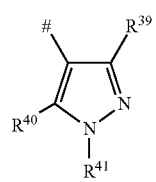

in which
R$^{39}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 atoms, aminocarbonyl and aminocarbonyl-C$_1$-C$_4$-alkyl, and R$^{40}$ is selected from the group consisting of hydrogen, halogen, cyano, C$_1$-C$_4$-alkyl, C$_1$-C$_4$-alkoxy, C$_1$-C$_4$-halogenoalkoxy having 1 to 5 halogen atoms, —S—C$_1$-C$_4$-alkylS(O)—C$_1$-C$_4$-alkyl, and —S(O)$_2$—C$_1$-C$_4$-alkyl, and R$^{41}$ is selected from the group consisting of hydrogen, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl, C$_1$-C$_4$-halogenoalkoxy-C$_1$-C$_4$-alkyl having 1 to 5 halogen atoms and phenyl (optionally substituted by halogen, C$_1$-C$_4$-alkyl, C$_1$-C$_4$-alkoxy-C$_1$-C$_4$-alkyl or nitro), or A represents a heterocycle of the formula (Het-14)

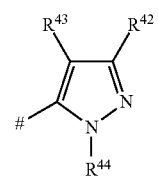

in which
R$^{42}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 halogen atoms, aminocarbonyl and aminocarbonyl-C$_1$-C$_4$-alkyl, and R$^{43}$ is selected from the group consisting of hydrogen, halogen, cyano, C$_1$-C$_4$-alkyl, C$_1$-C$_4$-alkoxy, —S—C$_1$-C$_4$-alkyl, S(O)—C$_1$-C$_4$-alkyl, —S(O)$_2$—C$_1$-C$_4$-alkyl, and C$_1$-C$_4$-halogenoalkyl having 1 to 5 halogen atoms, and R$^{44}$ is selected from the group consisting of hydrogen, phenyl, benzyl, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl and C$_1$-C$_4$-halogenoalkoxy-C$_1$-C$_4$-alkyl having 1 to 5 halogen atoms, or A represents a heterocycle of the formula (Het-15)

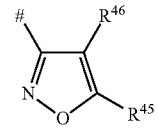

in which
R$^{45}$ and R$^{46}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-16)

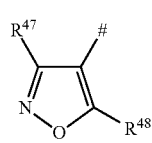
(Het-16)

in which
R$^{47}$ and R$^{48}$ may be the same or different and are selected from the group consisting of hydrogen, halogen, C$_1$-C$_4$-alkyl, C$_1$-C$_4$-halogenoalkyl having 1 to 5 halogen atoms, phenyl (optionally substituted by halogen or a C$_1$-C$_4$-alkyl), and heterocyclyl like pyridyl, pyrimidinyl and thiadiazolyl (each optionally substituted by halogen or C$_1$-C$_4$-alkyl), or A represents a heterocycle of the formula (Het-17)

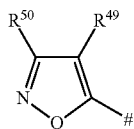
(Het-17)

in which
R$^{49}$ and R$^{50}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-18)

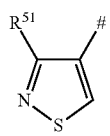
(Het-18)

in which
R$^{51}$ is selected from the group consisting of halogen, C$_1$-C$_4$-alkyl and C$_1$-C$_4$-halogenoalkyl having 1 to 5 halogen atoms, or A represents a heterocycle of the formula (Het-19)

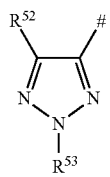
(Het-19)

in which
R$^{52}$ is selected from the group consisting of halogen, C$_1$-C$_4$-alkyl and C$_1$-C$_4$-halogenoalkyl having 1 to 5 halogen atoms, and
R$^{53}$ is selected from the group consisting of hydrogen, C$_1$-C$_4$-alkyl, C$_1$-C$_4$-halogenoalkyl having 1 to 5 halogen atoms and phenyl (optionally substituted by halogen or C$_1$-C$_4$-alkyl), or A represents a heterocycle of the formula (Het-20)

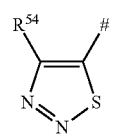
(Het-20)

in which
R$^{54}$ is selected from the group consisting of halogen, C$_1$-C$_4$-alkyl and C$_1$-C$_4$-halogenoalkyl having 1 to 5 halogen atoms, or A represents a heterocycle of the formula (Het-21)

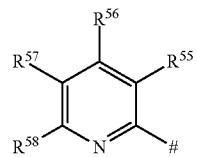
(Het-21)

in which
R$^{55}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and
R$^{56}$, R$^{57}$ and R$^{58}$, which may be the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl and —S(O)$_2$—C$_1$-C$_4$-alkyl, or A represents a heterocycle of the formula (Het-22)

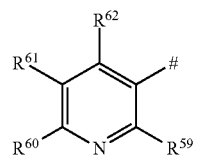
(Het-22)

in which
R$^{59}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$ alkoxy, —S—C$_1$-C$_5$-alkyl, S(O)—C$_1$-C$_4$-alkyl, —S(O)$_2$—C$_1$-C$_4$-alkyl, —S—C$_2$-C$_5$-alkenyl, —S—C$_1$-C$_4$-halogenoalkyl having 1 to 5 halogen atoms, C$_1$-C$_4$-halogenoalkoxy having 1 to 5 halogen atoms, phenyloxy (optionally substituted by halogen or C$_1$-C$_4$-alkyl) and —S-phenyl (optionally substituted by halogen or C$_1$-C$_4$-alkyl), and
R$^{60}$, R$^{61}$ and R$^{62}$, which may the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl, —S(O)$_2$—C$_1$-C$_4$-alkyl, N-morpholine optionally substituted by halogen or $C_1$-$C_4$-alkyl, and thienyl (optionally substituted by halogen or a $C_1$-$C_4$-alkyl), or A represents a heterocycle of the formula (Het-23)

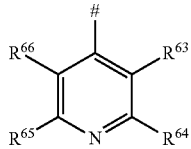

(Het-23)

in which
$R^{63}$, $R^{64}$, $R^{65}$ and $R^{66}$, which may be the same or different, are selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-24)

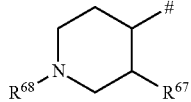

(Het-24)

in which
$R^{67}$ is selected from the group consisting of hydrogen, halogen, $C_1$-$C_4$-alkyl and $C_1$-$C_4$-halogenoalkyl having 1 to 5 halogen atoms, and
$R^{68}$ is selected from the group consisting of hydrogen, $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms), and heterocyclyl like pyridyl and pyrimidinyl (each optionally substituted by halogen, $C_1$-$C_4$-alkyl, $C_1$-$C_4$-halogenoalkyl having 1 to 5 halogen atoms), or A represents a heterocycle of the formula (Het-25)

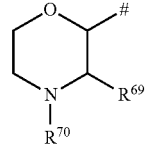

(Het-25)

in which
$R^{69}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and
$R^{70}$ is selected from the group consisting of hydrogen, $C_1$-$C_4$-alkyl, $C_1$-$C_4$-halogenoalkyl having 1 to 5 halogen atoms, and benzyl, or A represents a heterocycle of the formula (Het-26)

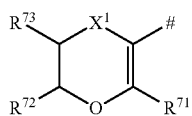

(Het-26)

in which
$X^1$ is selected from the group consisting of sulphur, —SO—, —SO$_2$— and —CH$_2$—, and
$R^{71}$ is selected from the group consisting of $C_1$-$C_4$-alkyl and $C_1$-$C_4$-halogenoalkyl having 1 to 5 halogen atoms, and
$R^{72}$ and $R^{73}$ may be the same or different and are selected from the group consisting of hydrogen and $C_1$-$C_4$-alkyl, or A represents a heterocycle of the formula (Het-27)

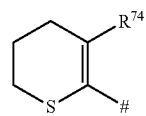

(Het-27)

in which
$R^{74}$ is selected from the group consisting of $C_1$-$C_4$-alkyl and $C_1$-$C_4$-halogenoalkyl having 1 to 5 halogen atoms, or A represents a heterocycle of the formula (Het-28)

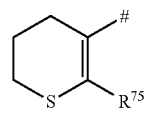

(Het-28)

in which
$R^{75}$ is selected from the group consisting of $C_1$-$C_4$-alkyl and $C_1$-$C_4$-halogenoalkyl having 1 to 5 halogen atoms, or A represents a heterocycle of the formula (Het-29)

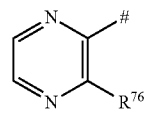

(Het-29)

in which
$R^{76}$ is selected from the group consisting of hydrogen, halogen, $C_1$-$C_4$-alkyl and $C_1$-$C_4$-halogenoalkyl having 1 to 5 halogen atoms.

In another individual aspect of embodiment 1-1, $R^1$ is fluorine. In another individual aspect of embodiment 1-1, $R^2$ is fluorine. In another individual aspect of embodiment 1-1, $R^1$ is fluorine and $R^2$ is fluorine. In another individual aspect of embodiment 1-1, the combination $R^1/R^2$ is fluorine/methyl. In another individual aspect of embodiment 1-2, $R^1$ is fluorine. In another individual aspect of embodiment 1-2, $R^2$ is fluorine. In another individual aspect of embodiment 1-2, $R^1$ is fluorine and $R^2$ is fluorine. In another individual aspect of embodiment 1-2, the combination $R^1/R^2$ is fluorine/methyl.

In embodiments 1-1 and 1-2 as well as in each individual aspect of said embodiments, Q preferably represents an optionally mono- or polysubstituted heteroaromatic ring from the group consisting of Q-1 to Q-64:
Q-1
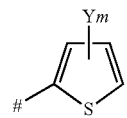
Q-2
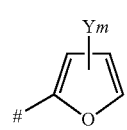
Q-3
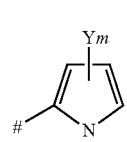
Q-4
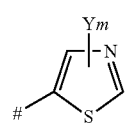
Q-5
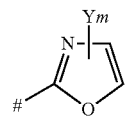
Q-6
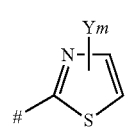
Q-7
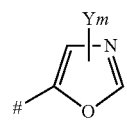
Q-8
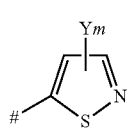
Q-9
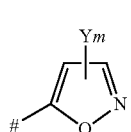
Q-10
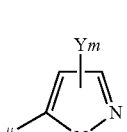
Q-11
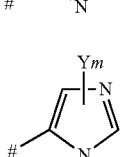
-continued
Q-12
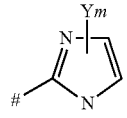
Q-13
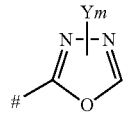
Q-14
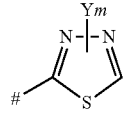
Q-15
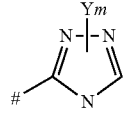
Q-16
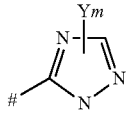
Q-17
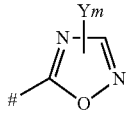
Q-18
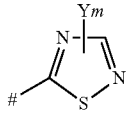
Q-19
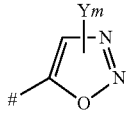
Q-20
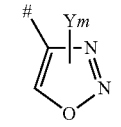
Q-21
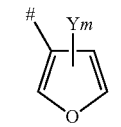
Q-22
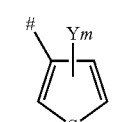
Q-23
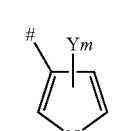

-continued
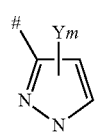 Q-24
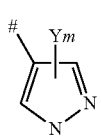 Q-25
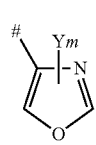 Q-26
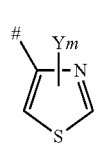 Q-27
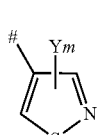 Q-28
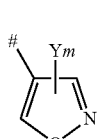 Q-29
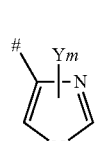 Q-30
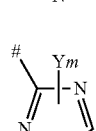 Q-31
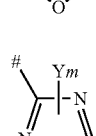 Q-32
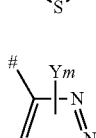 Q-33
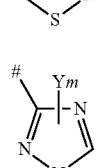 Q-34
-continued
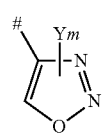 Q-35
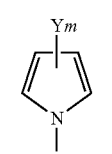 Q-36
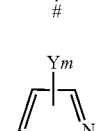 Q-37
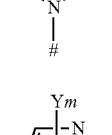 Q-38
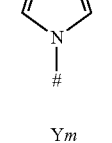 Q-39
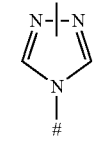 Q-40
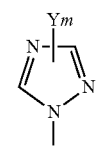 Q-41
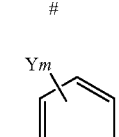 Q-42
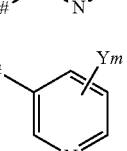 Q-43
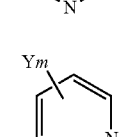 Q-44

-continued
Q-45 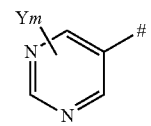
Q-46 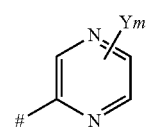
Q-47 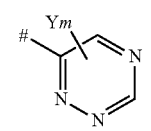
Q-48 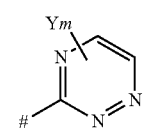
Q-49 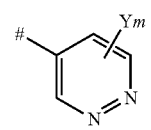
Q-50 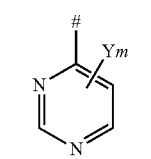
Q-51 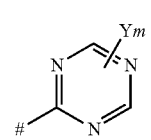
Q-52 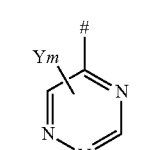
Q-53 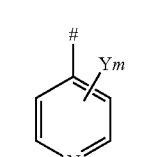
Q-54 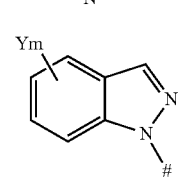
Q-55 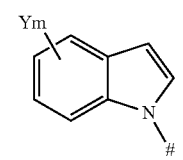
-continued
Q-56 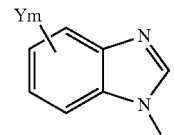
Q-57 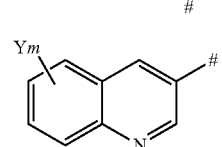
Q-58 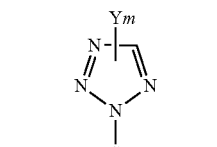
Q-59 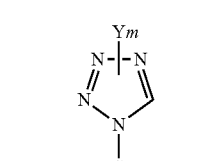
Q-60 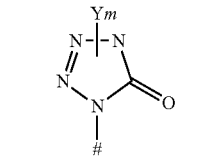
Q-61 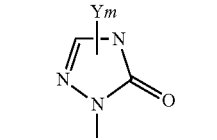
Q-62 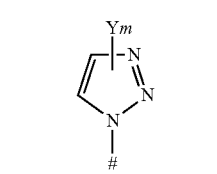
Q-63 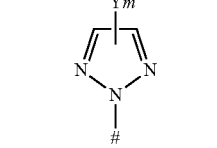
Q-64 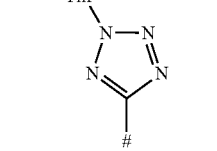
with
m is 0, 1 or 2, limited by the number of available positions in Q to which a substituent Y can be connected, and
each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino.

In embodiments 1-1 and 1-2 as well as in each individual aspect of said embodiments, Q preferably represents an optionally mono- or polysubstituted heteroaromatic ring from the group consisting of Q-41 to Q53 and Q-57 with m is 0, 1 or 2, limited by the number of available positions in Q to which a substituent Y can be connected, and each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino.

Preferred substituents or ranges of the structural elements mentioned in the compounds of formula (I) are explained below (embodiment 2-1).

$B^1$, $B^2$ represent C—X or N, wherein at least $B^1$ or $B^2$ is N, n is 1 or 2, limited by the number of available positions in the ring to which a substituent X can be connected, each X is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, Q represents an optionally mono- or polysubstituted heteroaromatic ring from the group consisting of Q-1, Q-2, Q-3, Q-4, Q-5, Q-6, Q-7, Q-8, Q-9, Q-10, Q-11, Q-12, Q-13, Q-14, Q-15, Q-16, Q-17. Q-18, Q-19, Q-20, Q-21, Q-22, Q-23, Q-24, Q-25, Q-26, Q-27, Q-28, Q-29, Q-30, Q-31, Q-32, Q-33, Q-34, Q-35, Q-36, Q-37, Q-38, Q-39, Q-40, Q-41, Q-42, Q-43, Q-44, Q-45, Q-46, Q-47, Q-48, Q-49, Q-50, Q-51, Q-52, Q-53, Q-54, Q-55, Q-56, Q-57, Q-58, Q-59, Q-60, Q-61, Q-62, Q-63 and Q-64 with m is 0, 1 or 2, limited by the number of available positions in Q to which a substituent Y can be connected, and each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—C$_1$-C$_4$-halogenoalkyl having 1 to 5 halogen atoms, —CH$_2$—S—C$_1$-C$_4$-alkyl, —CH$_2$—S(O)—C$_1$-C$_4$-alkyl, —CH$_2$—S(O)$_2$—C$_1$-C$_4$-alkyl, (C$_1$-C$_4$-alkoxyimino)-C$_1$-C$_4$-alkyl, (C$_2$-C$_6$-alkenyloxyimino)-C$_1$-C$_4$-alkyl, (C$_3$-C$_6$-alkynyloxyimino)-C$_1$-C$_4$-alkyl, (benzyloxyimino)-C$_1$-C$_6$-alkyl, benzyloxy, —S-benzyl, benzylamino, phenoxy, —S-phenyl and phenylamino, R$^1$, R$^2$, R$^3$ and R$^4$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^1$ and R$^2$ together with the carbon atom to which they are bonded form a 4- or 5-membered carbocycle and R$^3$ and R$^4$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^3$ and R$^4$ together with the carbon atom to which they are bonded form a 3-, 4- or 5-membered carbocycle and R$^1$ and R$^2$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_1$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^4$ and R$^2$ together with the carbon atom to which they are bonded form a 3-, 4- or 5-membered non-aromatic carbocycle optionally substituted by substituents selected from the group consisting of one to four C$_1$-C$_4$-alkyl groups and one to four halogen atoms, and R$^1$ and R$^3$ are the same or different and are selected from the group consisting of hydrogen, halogen, cyano, hydroxy, amino. —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_3$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl. —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^1$ and R$^3$ together with the carbon atom to which they are bonded form a 3-, 4- or 5-membered non-aromatic carbocycle optionally substituted by substituents selected from the group consisting of one to four C$_3$-C$_4$-alkyl groups and one to four halogen atoms, and R$^2$ and R$^4$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, R$^5$ is selected from the group consisting of hydrogen, —CHO, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, C$_3$-C$_6$-halogenocycloalkyl having 1 to 5 halogen atoms, C$_2$-C$_4$-alkenyl, C$_2$-C$_4$-alkynyl, C$_1$-C$_4$-alkoxy-C$_1$-C$_4$-alkyl, C$_3$-C$_6$-cycloalkyl-C$_1$-C$_3$-alkyl, cyano-C$_1$-C$_4$-alkyl, amino-C$_1$-C$_4$-alkyl, C$_1$-C$_4$-alkylamino-C$_1$-C$_4$-alkyl, di-(C$_1$-C$_4$-alkyl)amino-C$_1$-C$_4$-alkyl, C$_1$-C$_4$-alkylcarbonyl, C$_1$-C$_4$-halogenoalkylcarbonyl having 1 to 5 halogen atoms, C$_1$-C$_4$-alkoxycarbonyl, benzyloxycarbonyl, C$_1$-C$_4$-alkoxy-C$_1$-C$_4$-alkylcarbonyl, —S(O)$_2$—C$_1$-C$_4$-alkyl, and —S(O)$_2$—C$_1$-C$_4$-halogenoalkyl having 1 to 5 halogen atoms, A represents a phenyl group of formula (A1)

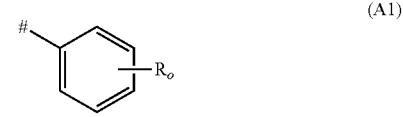

wherein
o is 0, 1 or 2, and
each R is independently selected from the group consisting of halogen, nitro, —OH, CHO, OCHO, NHCHO, cyano, C$_1$-C$_4$-alkyl, C$_1$-C$_4$-halogenoalkyl having 1 to 5 halogen atoms, C$_2$-C$_4$-alkenyl, C$_2$-C$_4$-alkynyl, C$_3$-C$_6$-cycloalkyl, —S—C$_1$-C$_4$-alkyl, —S—C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_1$-C$_4$-alkoxy-C$_2$-C$_4$-alkenyl, C$_1$-C$_4$-alkoxycarbonyl, C$_1$-C$_4$-halogenoalkoxycarbonyl having 1 to 5 halogen atoms, C$_1$-C$_4$-alkylcarbonyloxy, C$_1$-C$_4$-halogenoalkyl carbonyloxy having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$C$_1$-C$_4$-halogenoalkyl having 1 to 5 halogen atoms, C$_1$-C$_4$-alkylsulfonamide, —NH(C$_1$-C$_4$-alkyl), N(C$_1$-C$_4$-alkyl)$_2$, phenyl (optionally substituted by C$_1$-C$_4$-alkoxy) and phenoxy, or two R bonded to adjacent carbon atoms together represent —O(CH$_2$)$_p$O—, wherein p represents 1 or 2, or A represents a heterocycle of the formula (Het-1)

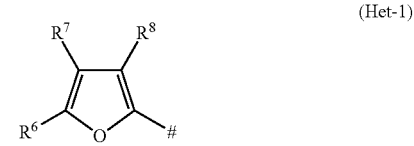

in which
R$^6$ and R$^7$ may be the same or different and are selected from the group consisting of hydrogen, halogen, nitro, C$_1$-C$_4$-alkyl and C$_1$-C$_4$-halogenoalkyl having 1 to 5 halogen atoms, and
R$^8$ is selected from the group consisting of hydrogen, halogen, C$_1$-C$_4$-alkyl and C$_1$-C$_4$-halogenoalkyl having 1 to 5 halogen atoms, or A represents a heterocycle of the formula (Het-2)

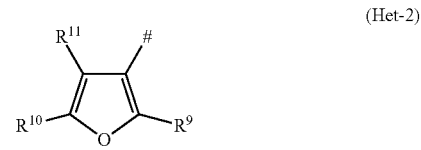

in which
R$^9$ is selected from the group consisting of hydrogen, halogen, C$_1$-C$_4$-alkyl and C$_1$-C$_4$-halogenoalkyl having 1 to 5 halogen atoms, and
R$^{10}$ and R$^{11}$ may be the same or different and are selected from the group consisting of hydrogen, halogen, C$_1$-C$_4$-alkyl and C$_1$-C$_4$-halogenoalkyl having 1 to 5 halogen atoms, phenyl optionally substituted by halogen or C$_1$-C$_4$-alkyl), or A represents a heterocycle of the formula (Het-4)

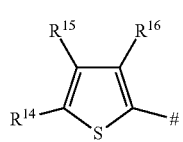
(Het-4)

in which
- $R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and
- $R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A represents a heterocycle of the formula (Het-5)

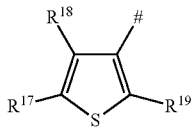
(Het-5)

in which
- $R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
- $R^{19}$ is selected from the group consisting of hydrogen, halogen, $C_1$-$C_4$-alkyl and $C_1$-$C_4$-halogenoalkyl having 1 to 5 atoms, or A represents a heterocycle of the formula (Het-6)

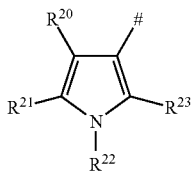
(Het-6)

in which
- $R^{20}$ is selected from the group consisting of hydrogen, halogen, cyano, $C_1$-$C_4$-alkyl and $C_1$-$C_4$-halogenoalkyl having 1 to 5 halogen atoms, and
- $R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and
- $R^{22}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, or A represents a heterocycle of the formula (Het-7)

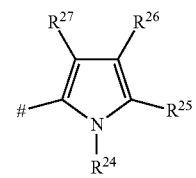
(Het-7)

in which
- $R^{24}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, $C_1$-$C_6$-alkylcarbonyl, or benzoyl (optionally substituted by halogen or a $C_1$-$C_4$-alkyl), and
- $R^{25}$, $R^{26}$ and $R^{27}$ may be the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or A represents a heterocycle of the formula (Het-9)

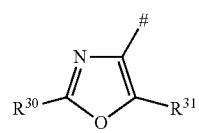
(Het-9)

in which
- $R^{30}$ is selected from the group consisting of hydrogen and $C_1$-$C_4$-alkyl, and
- $R^{31}$ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or A represents a heterocycle of the formula (Het-10)

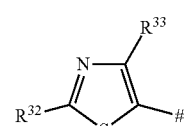
(Het-10)

in which
- $R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and
- $R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy comprising 1 to 9 halogen atoms, amino, substituted or unsubstituted $C_1$-$C_5$-alkylamino or substituted or unsubstituted di-($C_1$-$C_5$-alkyl)-amino, or A represents a heterocycle of the formula (Het-11)

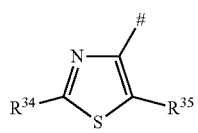

in which
R$^{34}$ is selected from the group consisting of hydrogen, halogen, C$_1$-C$_4$-alkylamino, di-(C$_1$-C$_4$-alkyl)amino, C$_1$-C$_4$-alkyl and C$_1$-C$_4$-halogenoalkyl having 1 to 5 halogen atoms, and
R$^{35}$ is selected from the group consisting of halogen, C$_1$-C$_4$-alkyl and C$_1$-C$_4$-halogenoalkyl having 1 to 5 halogen atoms, or
A represents a heterocycle of the formula (Het-12)

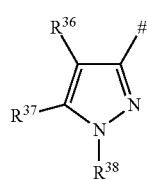

in which
R$^{36}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, —S(O)—C$_1$-C$_4$-alkyl, —S(O)$_2$—C$_1$-C$_4$-alkyl and —S—C$_1$-C$_4$-halogenoalkyl having 1 to 5 halogen atoms, and
R$^{37}$ is selected from the group consisting of hydrogen, halogen, cyano, nitro, C$_1$-C$_4$-alkyl, C$_1$-C$_4$-alkoxy and —S—C$_1$-C$_4$-alkyl, —S(O)—C$_1$-C$_4$-alkyl, —S(O)$_2$—C$_1$-C$_4$-alkyl, and
R$^{38}$ is selected from the group consisting of phenyl, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl and C$_1$-C$_4$-halogenoalkoxy-C$_1$-C$_4$-alkyl having 1 to 5 halogen atoms, or
A represents a heterocycle of the formula (Het-13)

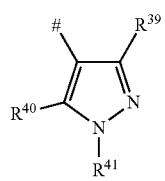

in which
R$^{39}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, —S(O)—C$_1$-C$_4$-alkyl, —S(O)$_2$—C$_1$-C$_4$-alkyl, —S—C$_1$-C$_4$-halogenoalkyl having 1 to 5 atoms, aminocarbonyl and aminocarbonyl-C$_1$-C$_4$-alkyl, and
R$^{40}$ is selected from the group consisting of hydrogen, halogen, cyano, C$_1$-C$_4$-alkyl, C$_1$-C$_4$-alkoxy, C$_1$-C$_4$-halogenoalkoxy having 1 to 5 halogen atoms, —S—C$_1$-C$_4$-alkyl, —S(O)—C$_1$-C$_4$-alkyl, and —S(O)$_2$—C$_1$-C$_4$-alkyl, and
R$^{41}$ is selected from the group consisting of hydrogen, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl, C$_1$-C$_4$-halogenoalkoxy-C$_1$-C$_4$-alkyl having 1 to 5 halogen atoms and phenyl optionally substituted by halogen, C$_1$-C$_4$-alkyl, C$_1$-C$_4$-alkoxy-C$_1$-C$_4$-alkyl or nitro, or
A represents a heterocycle of the formula (Het-14)

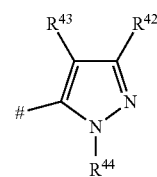

in which
R$^{42}$ is selected from the group consisting of hydrogen, halogen, cyano, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, —S(O)—C$_1$-C$_4$-alkyl, and —S(O)$_2$—C$_1$-C$_4$-alkyl, —S—C$_1$-C$_4$-halogenoalkyl having 1 to 5 halogen atoms, aminocarbonyl and aminocarbonyl-C$_1$-C$_4$-alkyl, and
R$^{43}$ is selected from the group consisting of hydrogen, halogen, cyano, C$_1$-C$_4$-alkyl, C$_1$-C$_4$-alkoxy, —S—C$_1$-C$_4$-alkyl, —S(O)—C$_1$-C$_4$-alkyl, and —S(O)$_2$—C$_1$-C$_4$-alkyl, and C$_1$-C$_4$-halogenoalkyl having 1 to 5 halogen atoms, and
R$^{44}$ is selected from the group consisting of phenyl, benzyl, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl and C$_1$-C$_4$-halogenoalkoxy-C$_1$-C$_4$-alkyl having 1 to 5 halogen atoms, or
A represents a heterocycle of the formula (Het-15)

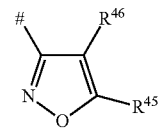

in which
R$^{45}$ and R$^{46}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-16)

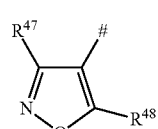
(Het-16)

in which
R$^{47}$ and R$^{48}$ may be the same or different and are selected from the group consisting of hydrogen, halogen, C$_1$-C$_4$-alkyl, C$_1$-C$_4$-halogenoalkyl having 1 to 5 halogen atoms, phenyl (optionally substituted by halogen or a C$_1$-C$_4$-alkyl), or heterocyclyl like pyridyl, pyrimidinyl and thiadiazolyl (optionally substituted by halogen or C$_1$-C$_4$-alkyl), or A represents a heterocycle of the formula (Het-17)

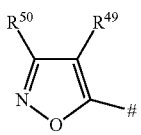
(Het-17)

in which
R$^{49}$ and R$^{50}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-19)

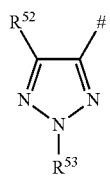
(Het-19)

in which
R$^{52}$ is selected from the group consisting of halogen, C$_1$-C$_4$-alkyl and C$_1$-C$_4$-halogenoalkyl having 1 to 5 halogen atoms, and
R$^{53}$ is selected from the group consisting of C$_1$-C$_4$-alkyl, C$_1$-C$_4$-halogenoalkyl having 1 to 5 halogen atoms and phenyl (optionally substituted by halogen or C$_1$-C$_4$-alkyl 1), or A represents a heterocycle of the formula (Het-20)

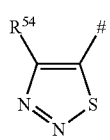
(Het-20)

in which
R$^{54}$ is selected from the group consisting of halogen, C$_1$-C$_4$-alkyl and C$_1$-C$_4$-halogenoalkyl having 1 to 5 halogen atoms, or A represents a heterocycle of the formula (Het-21)

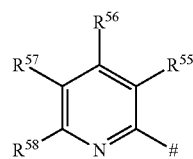
(Het-21)

in which
R$^{55}$ is selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S(O)—C$_1$-C$_4$-alkyl, —S(O)$_2$—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and
R$^{56}$, R$^{57}$ and R$^{58}$, which may be the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S(O)—C$_1$-C$_4$-alkyl, —S(O)$_2$—C$_1$-C$_4$-alkyl, C$_1$-C$_4$-halogenoalkoxy having 1 to 5 halogen atoms, —S(O)—C$_1$-C$_4$-alkyl and —S(O)$_2$—C$_1$-C$_4$-alkyl, or A represents a heterocycle of the formula (Het-22)

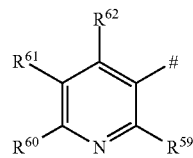
(Het-22)

in which
R$^{99}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$ alkoxy, —S—C$_1$-C$_5$-alkyl, —S(O)—C$_1$-C$_4$-alkyl, —S(O)$_2$—C$_1$-C$_4$-alkyl, —S—C$_2$-C$_5$-alkenyl, —S—C$_1$-C$_4$-halogenoalkyl having 1 to 5 halogen atoms, C$_1$-C$_4$-halogenoalkoxy having 1 to 5 halogen atoms, phenyloxy (optionally substituted by halogen or C$_1$-C$_4$-alkyl) and —S-phenyl (optionally substituted by halogen or C$_1$-C$_4$-alkyl), and
R$^{60}$, R$^{61}$ and R$^{62}$, which may the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl, —S(O)$_2$—C$_1$-C$_4$-alkyl, N-morpholine (optionally substituted by halogen or C$_1$-C$_4$-alkyl) and thienyl (optionally substituted by halogen or a C$_1$-C$_4$-alkyl), or A represents a heterocycle of the formula (Het-23)

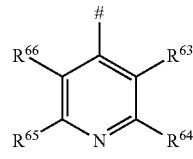
(Het-23)

in which $R^{63}$, $R^{64}$, $R^{65}$ and $R^{66}$, which may be the same or different, are selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-24)

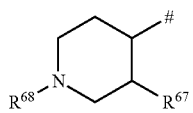

(Het-24)

in which $R^{67}$ is selected from the group consisting of hydrogen, halogen, $C_1$-$C_4$-alkyl and $C_1$-$C_4$-halogenoalkyl having 1 to 5 halogen atoms, and $R^{68}$ is selected from the group consisting of $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms) and heterocyclyl like pyrimidinyl, (optionally substituted by halogen, $C_1$-$C_4$-alkyl, $C_1$-$C_4$-halogenoalkyl having 1 to 5 halogen atoms), or A represents a heterocycle of the formula (Het-25)

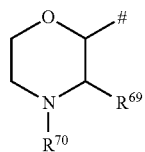

(Het-25)

in which $R^{69}$ is selected from the group consisting of hydrogen, $C_1$-$C_4$-alkyl and $C_1$-$C_4$-halogenoalkyl having 1 to 5 halogen atoms, and $R^{70}$ is selected from the group consisting of hydrogen, $C_1$-$C_4$-alkyl, $C_1$-$C_4$-halogenoalkyl having 1 to 5 halogen atoms and benzyl, or A represents a heterocycle of the formula (Het-26)

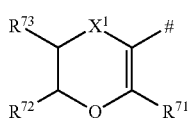

(Het-26)

in which $X^1$ is selected from the group consisting of sulphur, —SO—, or —SO$_2$—, and $R^{71}$ is selected from the group consisting of $C_1$-$C_4$-alkyl and $C_1$-$C_4$-halogenoalkyl having 1 to 5 halogen atoms, and $R^{72}$ and $R^{73}$ may be the same or different and are selected from the group consisting of hydrogen and $C_1$-$C_4$-alkyl, or A represents a heterocycle of the formula (Het-29)

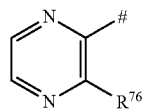

(Het-29)

in which $R^{76}$ is selected from the group consisting of hydrogen, halogen, $C_1$-$C_4$-alkyl and $C_1$-$C_4$-halogenoalkyl having 1 to 5 halogen atoms.

In an individual embodiment (embodiment 2-2), the structural elements in the compound of formula (I) are preferably defined as follows:

$B^1$, $B^2$ represent C—X or N, wherein at least $B^1$ or $B^2$ is N.

n is 1 or 2, limited by the number of available positions in the ring to which a substituent X can be connected, each X is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, Q represents an optionally mono- or polysubstituted heteroaromatic ring from the group consisting of Q-41, Q-42, Q-43, Q-44, Q-45, Q-46, Q-47, Q-48, Q-49, Q-50, Q-51, Q-52, Q-53 and Q-57 with m is 0, 1 or 2, limited by the number of available positions in Q to which a substituent Y can be connected, and each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_4$-cycloalkyl, $C_1$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-

$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^2$ together with the carbon atom to which they are bonded form a 4- or 5-membered carbocycle and $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^3$ and $R^4$ together with the carbon atom to which they are bonded form a 3-, 4- or 5-membered carbocycle and $R^1$ and $R^2$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^4$ and $R^2$ together with the carbon atom to which they are bonded form a 3-, 4- or 5-membered non-aromatic carbocycle optionally substituted by substituents selected from the group consisting of one to four $C_1$-$C_4$-alkyl groups and one to four halogen atoms, and $R^1$ and $R^3$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$- halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl, having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^3$ together with the carbon atom to which they are bonded form a 3-, 4- or 5-membered non-aromatic carbocycle optionally substituted by substituents selected from the group consisting of one to four $C_1$-$C_4$-alkyl groups and one to four halogen atoms, and $R^2$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_1$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, $R^1$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_2$-$C_4$-alkenyl, $C_2$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di-($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —S(O)$_2$—$C_1$-$C_4$-alkyl, and —S(O)$_2$—$C_1$-$C_4$-halogenoalkyl having 1 to 5 halogen atoms, A represents a phenyl group of formula (A1)

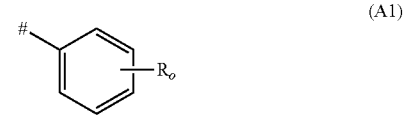

(A1)

wherein o is 0, 1 or 2, and each R is independently selected from the group consisting of halogen, nitro, —OH, CHO, OCHO, NHCHO, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_3$-$C_6$-cycloalkyl, —S—$C_1$-$C_4$-alkyl, —S—$C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkoxy-$C_2$-$C_4$-alkenyl, $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$$C_1$-$C_4$-halogenoalkyl having 1 to 5 halogen atoms, $C_1$-$C_4$-alkylsulfonamide, —NH($C_1$-$C_4$-alkyl), N($C_1$-$C_4$-alkyl)$_2$, phenyl (optionally substituted by $C_1$-$C_4$-alkoxy) and phenoxy, or two R bonded to adjacent carbon atoms together represent —O(CH$_2$)$_p$O—, wherein p represents 1 or 2, or A represents a heterocycle of the formula (Het-1)

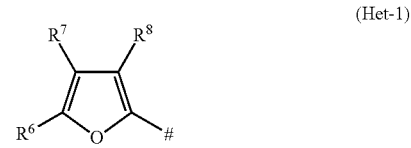

(Het-1)

in which $R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and $R^8$ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

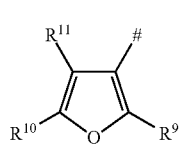
(Het-2)

in which

R$^9$ is selected from the group consisting of hydrogen, halogen, C$_1$-C$_4$-alkyl and C$_1$-C$_4$-halogenoalkyl having 1 to 5 halogen atoms, and R$^{10}$ and R$^{11}$ may be the same or different and are selected from the group consisting of hydrogen, halogen, C$_1$-C$_4$-alkyl and C$_1$-C$_4$-halogenoalkyl having 1 to 5 halogen atoms, phenyl optionally substituted by halogen or C$_1$-C$_4$-alkyl), or A represents a heterocycle of the formula (Het-4)

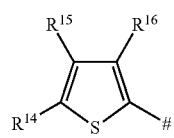
(Het-4)

in which

R$^4$ and R$^{15}$ may be the same or different and are selected from the group consisting of hydrogen, halogen, C$_1$-C$_4$-alkyl, C$_1$-C$_4$-halogenoalkyl having 1 to 5 halogen atoms, —S—C$_1$-C$_4$-alkyl, —S(O)$_2$—C$_1$-C$_4$-alkyl, phenyl (optionally substituted by halogen or C$_1$-C$_4$-alkyl) and pyridyl (optionally substituted by halogen or C$_1$-C$_4$-alkyl), and R$^{16}$ is selected from the group consisting of hydrogen, halogen, cyano, C$_1$-C$_4$-alkyl, C$_1$-C$_4$-halogenoalkyl having 1 to 5 halogen atoms and C$_1$-C$_4$-halogenoalkoxy having 1 to 5 halogen atoms, or A represents a heterocycle of the formula (Het-5)

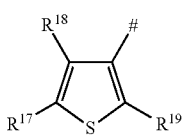
(Het-5)

in which

R$^{17}$ and R$^{18}$ may be the same or different and are selected from the group consisting of hydrogen, halogen, C$_1$-C$_4$-alkyl, C$_1$-C$_4$-alkyloxy and C$_1$-C$_4$-halogenoalkyl having 1 to 5 halogen atoms, and R$^{19}$ is selected from the group consisting of hydrogen, halogen, C$_1$-C$_4$-alkyl and C$_1$-C$_4$-halogenoalkyl having 1 to 5 atoms, or A represents a heterocycle of the formula (Het-6)

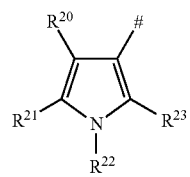
(Het-6)

in which

R$^{20}$ is selected from the group consisting of hydrogen, halogen, cyano, C$_1$-C$_4$-alkyl and C$_1$-C$_4$-halogenoalkyl having 1 to 5 halogen atoms, and R$^{21}$ and R$^{23}$ may be the same or different and are selected from the group consisting of hydrogen, halogen, C$_1$-C$_4$-alkyl and C$_1$-C$_4$-halogenoalky having 1 to 5 halogen atoms, and R$^{22}$ is selected from the group consisting of hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, or A represents a heterocycle of the formula (Het-7)

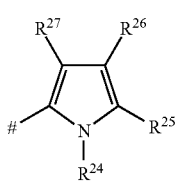
(Het-7)

in which

R$^{24}$ is selected from the group consisting of hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, C$_1$-C$_6$-alkylcarbonyl, or benzoyl (optionally substituted by halogen or a C$_1$-C$_4$-alkyl), and R$^{25}$, R$^{26}$ and R$^{27}$ may be the same or different and are selected from the group consisting of hydrogen, halogen, cyano, C$_1$-C$_4$-alkyl, C$_1$-C$_4$-halogenalkyl having 1 to 5 halogen atoms and C$_1$-C$_4$-alkylcarbonyl, or A represents a heterocycle of the formula (Het-9)

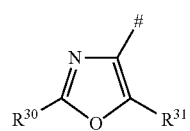
(Het-9)

in which

R$^{30}$ is selected from the group consisting of hydrogen and C$_1$-C$_4$-alkyl, and R$^{31}$ is selected from the group consisting of halogen, C$_1$-C$_4$-alkyl, C$_1$-C$_4$-halogenoalkyl having 1 to 5 halogen atoms and phenyl (optionally substituted by halogen or C$_1$-C$_4$-alkyl), or A represents a heterocycle of the formula (Het-10)

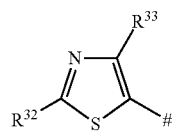

in which
R³² is selected from the group consisting of hydrogen, halogen, amino, cyano, C₁-C₄-alkylamino, di-(C₁-C₄-alkyl)amino, C₁-C₄-alkyl, C₁-C₄-halogenoalkyl having 1 to 5 halogen atoms and phenyl (optionally substituted by halogen or C₁-C₄-alkyl), and
R³³ is selected from the group consisting of halogen, C₁-C₄-alkyl and C₁-C₄-halogenoalkyl having 1 to 5 halogen atoms, C₁-C₅-halogenoalkoxy comprising 1 to 9 halogen atoms, amino, substituted or unsubstituted C₁-C₅-alkylamino or substituted or unsubstituted di-(C₁-C₅-alkyl)-amino, or
A represents a heterocycle of the formula (Het-11)

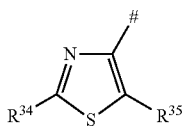

in which
R³⁴ is selected from the group consisting of hydrogen, halogen, C₁-C₄-alkylamino, di-(C₁-C₄-alkyl)amino, C₁-C₄-alkyl and C₁-C₄-halogenoalkyl having 1 to 5 halogen atoms, and
R³⁵ is selected from the group consisting of halogen, C₁-C₄-alkyl and C₁-C₄-halogenoalkyl having 1 to 5 halogen atoms, or
A represents a heterocycle of the formula (Het-12)

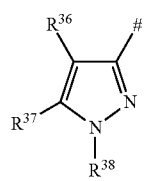

in which
R³⁶ is selected from the group consisting of hydrogen, halogen, cyano, nitro, C₁-C₄-alkyl, C₁-C₄-halogenoalkyl having 1 to 5 halogen atoms, C₁-C₆-cycloalkyl, C₁-C₄-alkoxy, C₁-C₄-halogenoalkoxy having 1 to 5 halogen atoms, —S—C₁-C₄-alkyl, —S(O)—C₁-C₄-alkyl, —S(O)₂—C₁-C₄-alkyl and —S—C₁-C₄-halogenoalkyl having 1 to 5 halogen atoms, and
R³⁷ is selected from the group consisting of hydrogen, halogen, cyano, nitro, C₁-C₄-alkyl, C₁-C₄-alkoxy and —S—C₁-C₄-alkyl, —S(O)—C₁-C₄-alkyl, —S(O)₂C₁-C₄-alkyl, and
R³⁸ is selected from the group consisting of phenyl, C₁-C₄-alkyl, C₁-C₄-halogenoalkyl having 1 to 5 halogen atoms, hydroxy-C₁-C₄-alkyl, C₂-C₆-alkenyl, C₁-C₆-cycloalkyl, C₁-C₄-alkylthio-C₁-C₄-alkyl, C₁-C₄-alkyl-S(O)—C₁-C₄-alkyl, C₁-C₄-alkyl-S(O)₂—C₁-C₄-alkyl, C₁-C₄-halogenoalkylthio-C₁-C₄-alkyl having 1 to 5 halogen atoms, C₁-C₄-alkoxy-C₁-C₄-alkyl and C₁-C₄-halogenoalkoxy-C₁-C₄-alkyl having 1 to 5 halogen atoms, or
A represents a heterocycle of the formula (Het-13)

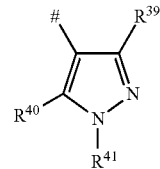

in which
R³⁹ is selected from the group consisting of hydrogen, halogen, cyano, nitro, C₁-C₄-alkyl, C₁-C₄-halogenoalkyl having 1 to 5 halogen atoms, C₃-C₆-cycloalkyl, C₁-C₄-alkoxy, C₁-C₄-halogenoalkoxy having 1 to 5 halogen atoms, —S—C₁-C₄-alkyl, —S(O)—C₁-C₄-alkyl, —S(O)₂—C₁-C₄-alkyl, —S—C₁-C₄-halogenoalkyl having 1 to 5 atoms, aminocarbonyl and aminocarbonyl-C₁-C₄-alkyl, and
R⁴⁰ is selected from the group consisting of hydrogen, halogen, cyano, C₁-C₄-alkyl, C₁-C₄-alkoxy, C₁-C₄-halogenoalkoxy having 1 to 5 halogen atoms, —S—C₁-C₄-alkyl, —S(O)—C₁-C₄-alkyl, and —S(O)₂—C₁-C₄-alkyl, and
R⁴¹ is selected from the group consisting of hydrogen, C₁-C₄-alkyl, C₁-C₄-halogenoalkyl having 1 to 5 halogen atoms, hydroxy-C₁-C₄-alkyl, C₂-C₆-alkenyl, C₃-C₆-cycloalkyl, C₁-C₄-alkylthio-C₁-C₄-alkyl, C₁-C₄-alkyl-S(O)—C₁-C₄-alkyl, C₁-C₄-alkyl-S(O)₂—C₁-C₄-alkyl, C₁-C₄-halogenoalkylthio-C₁-C₄-alkyl having 1 to 5 halogen atoms, C₁-C₄-alkoxy-C₁-C₄-alkyl, C₁-C₄-halogenoalkoxy-C₁-C₄-alkyl having 1 to 5 halogen atoms and phenyl optionally substituted by halogen, C₁-C₄-alkyl, C₁-C₄-alkoxy-C₁-C₄-alkyl or nitro, or
A represents a heterocycle of the formula (Het-14)

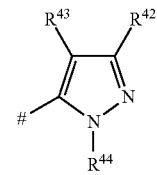

in which
R⁴² is selected from the group consisting of hydrogen, halogen, cyano, C₁-C₄-alkyl, C₁-C₄-halogenoalkyl having 1 to 5 halogen atoms, C₃-C₆-cycloalkyl, C₁-C₄-alkoxy, C₁-C₄-halogenoalkoxy having 1 to 5 halogen atoms, —S—C₁-C₄-alkyl, —S(O)—C₁-C₄-alkyl, and —S(O)₂—C₁-C₄-alkyl, —S—C₁-C₄-halogenoalkyl having 1 to 5 halogen atoms, aminocarbonyl and aminocarbonyl-C₁-C₄-alkyl, and
R⁴³ is selected from the group consisting of hydrogen, halogen, cyano, C₁-C₄-alkyl, C₁-C₄-alkoxy, —S—C₁-C₄-alkyl, —S(O)—C₁-C₄-alkyl, and —S(O)₂—C₁-C₄-alkyl, and C₁-C₄-halogenoalkyl having 1 to 5 halogen atoms, and $R^{44}$ is selected from the group consisting of phenyl, benzyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or A represents a heterocycle of the formula (Het-15)

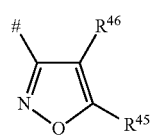

in which $R^{45}$ and $R^{46}$ may be the same or different and are selected from the group consisting of hydrogen, halogen, $C_1$-$C_4$-alkyl and $C_1$-$C_4$-halogenoalkyl having 1 to 5 halogen atoms, or A represents a heterocycle of the formula (Het-16)

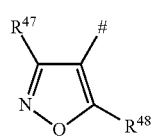

in which $R^{47}$ and $R^{48}$ may be the same or different and are selected from the group consisting of hydrogen, halogen, $C_1$-$C_4$-alkyl, $C_1$-$C_4$-halogenoalkyl having 1 to 5 halogen atoms, phenyl (optionally substituted by halogen or a $C_1$-$C_4$-alkyl), or heterocyclyl like pyridyl, pyrimidinyl and thiadiazolyl (optionally substituted by halogen or $C_1$-$C_4$-alkyl), or A represents a heterocycle of the formula (Het-17)

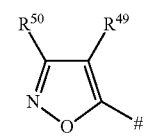

in which $R^{49}$ and $R^{50}$ may be the same or different and are selected from the group consisting of hydrogen, halogen, $C_1$-$C_4$-alkyl and $C_1$-$C_4$-halogenoalkyl having 1 to 5 halogen atoms, or A represents a heterocycle of the formula (Het-19)

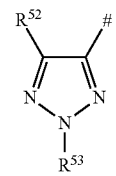

in which $R^{52}$ is selected from the group consisting of halogen, $C_1$-$C_4$-alkyl and $C_1$-$C_4$-halogenoalkyl having 1 to 5 halogen atoms, and $R^{53}$ is selected from the group consisting of $C_1$-$C_4$-alkyl, $C_1$-$C_4$-halogenoalkyl having 1 to 5 halogen atoms and phenyl (optionally substituted by halogen or $C_1$-$C_4$-alkyl), or A represents a heterocycle of the formula (Het-20)

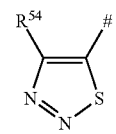

in which $R^{54}$ is selected from the group consisting of halogen, $C_1$-$C_4$-alkyl and $C_1$-$C_4$-halogenoalkyl having 1 to 5 halogen atoms, or A represents a heterocycle of the formula (Het-21)

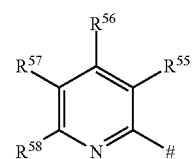

in which $R^{55}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-22)

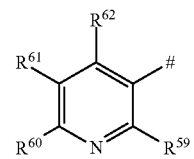

in which $R^{59}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, —S(O)—$C_1$-$C_4$-alkyl, —S(O)$_2$—$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or C$_1$-C$_4$-alkyl) and —S-phenyl (optionally substituted by halogen or C$_1$-C$_4$-alkyl), and R$^{60}$, R$^{61}$ and R$^{62}$, which may the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl, —S(O)$_2$—C$_1$-C$_4$-alkyl, N-morpholine (optionally substituted by halogen or C$_1$-C$_4$-alkyl) and thienyl (optionally substituted by halogen or a C$_1$-C$_4$-alkyl), or A represents a heterocycle of the formula (Het-23)

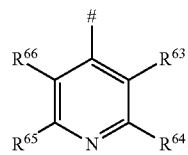

(Het-23)

in which
R$^{63}$, R$^{64}$, R$^{65}$ and R$^{66}$, which may be the same or different, are selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S—C$_1$-C$_4$-halogenoalkyl having 1 to 5 halogen atoms, C$_1$-C$_4$-halogenoalkoxy having 1 to 5 halogen atoms, —S(O)—C$_1$-C$_4$-alkyl and —S(O)$_2$—C$_1$-C$_4$-alkyl, or A represents a heterocycle of the formula (Het-24)

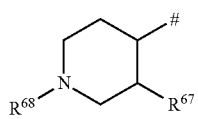

(Het-24)

in which
R$^{67}$ is selected from the group consisting of hydrogen, halogen, C$_1$-C$_4$-alkyl and C$_1$-C$_4$-halogenoalkyl having 1 to 5 halogen atoms, and R$^{68}$ is selected from the group consisting of C$_1$-C$_4$-alkyl, C$_1$-C$_4$-halogenoalkyl having 1 to 5 halogen atoms, C$_1$-C$_6$-alkoxycarbonyl, benzyl (optionally substituted by 1 to 3 halogen atoms), benzyloxycarbonyl (optionally substituted by 1 to 3 halogen atoms) and heterocyclyl like pyrimidinyl, (optionally substituted by halogen, C$_1$-C$_4$-alkyl, C$_1$-C$_4$-halogenoalkyl having 1 to 5 halogen atoms), or A represents a heterocycle of the formula (Het-25)

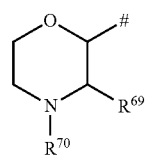

(Het-25)

in which
R$^{69}$ is selected from the group consisting of hydrogen, C$_1$-C$_4$-alkyl and C$_1$-C$_4$-halogenoalkyl having 1 to 5 halogen atoms, and R$^{70}$ is selected from the group consisting of hydrogen, C$_1$-C$_4$-alkyl, C$_1$-C$_4$-halogenoalkyl having 1 to 5 halogen atoms and benzyl, or A represents a heterocycle of the formula (Het-26)

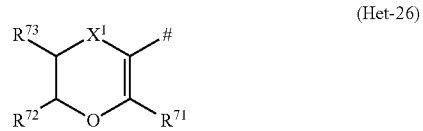

(Het-26)

in which
X$^1$ is selected from the group consisting of sulphur, —SO—, or —SO$_2$—, and R$^{71}$ is selected from the group consisting of C$_1$-C$_4$-alkyl and C$_1$-C$_4$-halogenoalkyl having 1 to 5 halogen atoms, and R$^{72}$ and R$^{73}$ may be the same or different and are selected from the group consisting of hydrogen and C$_1$-C$_4$-alkyl, or A represents a heterocycle of the formula (Het-29)

(Het-29)

in which
R$^{76}$ is selected from the group consisting of hydrogen, halogen, C$_1$-C$_4$-alkyl and C$_1$-C$_4$-halogenoalkyl having 1 to 5 halogen atoms.

In another individual aspect of embodiment 2-1, R$^1$ is fluorine. In another individual aspect of embodiment 2-1, R$^2$ is fluorine. In another individual aspect of embodiment 2-1, R$^1$ is fluorine and R$^2$ is fluorine. In another individual aspect of embodiment 2-1, the combination R$^1$/R$^2$ is fluorine/methyl.

In another individual aspect of embodiment 2-2, R$^1$ is fluorine. In another individual aspect of embodiment 2-2, R$^1$ is fluorine. In another individual aspect of embodiment 2-2, R$^1$ is fluorine and R$^2$ is fluorine. In another individual aspect of embodiment 2-2, the combination R$^1$/R$^2$ is fluorine/methyl.

More preferred substituents or ranges of the structural elements mentioned in the compounds of formula (I) are explained below (embodiment 3-1).

B$^1$, B$^2$ represent C—X or N, wherein at least B$^1$ or B$^2$ is N, n is 1.

X is selected from the group consisting of hydrogen, halogen, nitro, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, Q represents an optionally mono- or polysubstituted heteroaromatic ring from the group consisting of Q-4, Q-11, Q-21, Q-22, Q-25, Q-36, Q-37, Q-38, Q-40, Q-41, Q-42, Q-53, Q-58, Q-62, Q63 and Q-64, with m is 0, 1 or 2, limited by the number of available positions in Q to which a substituent Y can be connected, and each Y is independently selected from the group consisting of hydrogen, —CF$_3$, —CH$_2$CF$_3$, methyl, ethyl, fluorine, chlorine, bromine, iodine, cyano, —OCH$_3$, —OCH$_2$CH$_3$, —OCH(CH$_3$)$_2$, —OCH$_2$CF$_3$, —CH$_2$—S(O)$_2$—CH$_3$, R¹ and R² are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, R³ and R⁴ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, or R¹ and R² together with the carbon atom to which they are bonded form a 4- or 5-membered carbocycle, and R³ and R⁴ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)$C_1$-$C_4$-alkyl, and phenyl, preferably R¹ and R² together with the carbon atom to which they are bonded form a cyclopentyl, or R³ and R⁴ together with the carbon atom to which they are bonded form a 3-, 4- or 5-membered carbocycle, and R¹ and R² are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, preferably R³ and R⁴ together with the carbon atom to which they are bonded form a cyclopropyl or a cyclobutyl, or R² and R⁴ together with the carbon atom to which they are bonded form a 3-, 4- or 5-membered non-aromatic carbocycle optionally substituted by substituents selected from the group consisting of one to four $C_1$-$C_3$-alkyl groups and one to two halogen atoms, and R¹ is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and R³ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably R² and R⁴ together with the carbon atom to which they are bonded form a cyclopropyl, cyclobutyl or cyclopentyl, or R¹ and R³ together with the carbon atom to which they are bonded form a 3-, 4- or 5-membered non-aromatic carbocycle optionally substituted by substituents selected from the group consisting of one to four $C_1$-$C_3$-alkyl groups and one to two halogen atoms, preferably cyclopropyl, cyclobutyl or cyclopentyl, and R² is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and R⁴ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably R¹ and R³ together with the carbon atom to which they are bonded form a cyclopropyl, cyclobutyl or cyclopentyl, R⁵ is selected from the group consisting of hydrogen, $C_3$-$C_6$-cycloalkyl, $C_1$-$C_4$-alkylcarbonyl, $C_1$-$C_4$-alkoxycarbonyl, A represents a phenyl group of formula (A1)

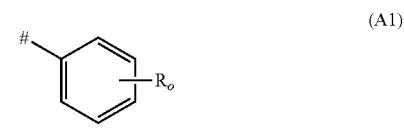

(A1)

wherein o is 0, 1 or 2, and each R is independently selected from the group consisting of halogen, nitro, —OH, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-alkoxycarbonyl, —NH($C_1$-$C_4$-alkyl), phenyl (optionally substituted by $C_1$-$C_4$-alkoxy) and phenoxy, or A represents a heterocycle of the formula (Het-1)

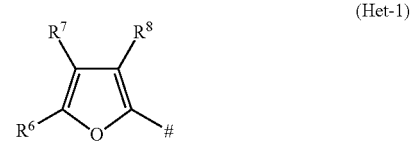

(Het-1)

in which

R⁶ and R⁷ may be the same or different and are selected from the group consisting of hydrogen, halogen, nitro, $C_1$-$C_4$-alkyl and $C_1$-$C_4$-halogenoalkyl having 1 to 5 halogen atoms, and R¹ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

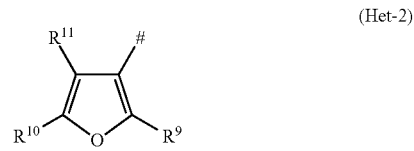

(Het-2)

in which

R⁹ is selected from the group consisting of hydrogen, halogen, $C_1$-$C_4$-alkyl and $C_1$-$C_4$-halogenoalkyl having 1 to 5 halogen atoms, and R¹⁰ and R¹¹ may be the same or different and are selected from the group consisting of hydrogen, halogen, $C_1$-$C_4$-alkyl and $C_1$-$C_4$-halogenoalkyl having 1 to 5 halogen atoms, phenyl optionally substituted by halogen or $C_1$-$C_4$-alkyl), or A represents a heterocycle of the formula (Het-4)

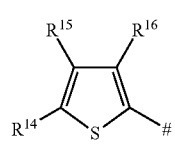
(Het-4)

in which

R$^{14}$ and R$^{15}$ may be the same or different and are selected from the group consisting of hydrogen, halogen, C$_1$-C$_4$-alkyl, C$_1$-C$_4$-halogenoalkyl having 1 to 5 halogen atoms, —S—C$_1$-C$_4$-alkyl, —S(O)$_2$—C$_1$-C$_4$-alkyl, phenyl (optionally substituted by halogen or C$_1$-C$_4$-alkyl) and pyridyl (optionally substituted by halogen or C$_1$-C$_4$-alkyl), and R$^{16}$ is selected from the group consisting of hydrogen, halogen, cyano, C$_1$-C$_4$-alkyl, C$_1$-C$_4$-halogenoalkyl having 1 to 5 halogen atoms and C$_1$-C$_4$-halogenoalkoxy having 1 to 5 halogen atoms, or A represents a heterocycle of the formula (Het-5)

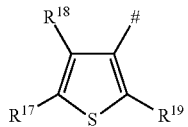
(Het-5)

in which

R$^{17}$ and R$^{18}$ may be the same or different and are selected from the group consisting of hydrogen, halogen, C$_1$-C$_4$-alkyl, C$_1$-C$_4$-alkyloxy and C$_1$-C$_4$-halogenoalkyl having 1 to 5 halogen atoms, and R$^{19}$ is selected from the group consisting of hydrogen, halogen, C$_1$-C$_4$-alkyl and C$_1$-C$_4$-halogenoalkyl having 1 to 5 atoms, or A represents a heterocycle of the formula (Het-6)

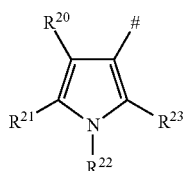
(Het-6)

in which

R$^{20}$ is selected from the group consisting of hydrogen, halogen, cyano, C$_1$-C$_4$-alkyl and C$_1$-C$_4$-halogenoalkyl having 1 to 5 halogen atoms, and R$^{21}$ and R$^{23}$ may be the same or different and are selected from the group consisting of hydrogen, halogen, C$_1$-C$_4$-alkyl and C$_1$-C$_4$-halogenoalky having 1 to 5 halogen atoms, and R$^{22}$ is selected from the group consisting of hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, or A represents a heterocycle of the formula (Het-10)

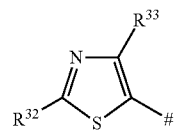
(Het-10)

in which

R$^{32}$ is selected from the group consisting of hydrogen, halogen, amino, cyano, C$_1$-C$_4$-alkylamino, di-(C$_1$-C$_4$-alkyl)amino, C$_1$-C$_4$-alkyl, C$_1$-C$_4$-halogenoalkyl having 1 to 5 halogen atoms and phenyl (optionally substituted by halogen or C$_1$-C$_4$-alkyl), and R$^{33}$ is selected from the group consisting of halogen, C$_1$-C$_4$-alkyl and C$_1$-C$_4$-halogenoalkyl having 1 to 5 halogen atoms, C$_1$-C$_5$-halogenoalkoxy comprising 1 to 9 halogen atoms, amino, substituted or unsubstituted C$_1$-C$_5$-alkylamino or substituted or unsubstituted di-(C$_1$-C$_5$-alkyl)-amino, or A represents a heterocycle of the formula (Het-21)

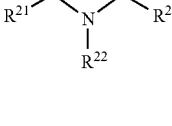
(Het-21)

in which

R$^{55}$ is selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S(O)—C$_1$-C$_4$-alkyl, —S(O)$_2$—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and R$^{56}$, R$^{57}$ and R$^{58}$, which may be the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl and —S(O)$_2$—C$_1$-C$_4$-alkyl, or A represents a heterocycle of the formula (Het-22)

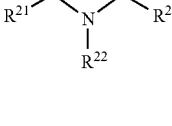
(Het-22)

in which

R$^{59}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$ alkoxy, —S—C$_1$-C$_5$-alkyl, —S(O)—C$_1$-C$_4$-alkyl, —S(O)$_2$—C$_1$-C$_4$-alkyl, —S—C$_2$-C$_5$-alkenyl, —S—C$_1$-C$_4$-halogenoalkyl having 1 to 5 halogen atoms, C$_1$-C$_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), and $R^{60}$, $R^{61}$ and $R^{62}$, which may the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl. N-morpholine (optionally substituted by halogen or $C_1$-$C_4$-alkyl) and thienyl (optionally substituted by halogen or a $C_1$-$C_4$-alkyl), or A represents a heterocycle of the formula (Het-29)

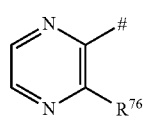

(Het-29)

in which $R^{76}$ is selected from the group consisting of hydrogen, halogen, $C_1$-$C_4$-alkyl and $C_1$-$C_4$-halogenoalkyl having 1 to 5 halogen atoms.

In an individual embodiment (embodiment 3-2), the structural elements in the compound of formula (I) are more preferably defined as follows:

$B^1$, $B^2$ represent C—X or N, wherein at least $B^1$ or $B^2$ is N.

n is 1,

X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, Q represents an optionally mono- or polysubstituted heteroaromatic ring from the group consisting of Q-41, Q-42 and Q-53.

with m is 0, 1 or 2, limited by the number of available positions in Q to which a substituent Y can be connected, and each Y is independently selected from the group consisting of hydrogen, —$CF_3$, —$CH_2CF_3$, methyl, ethyl, fluorine, chlorine, bromine, iodine, cyano, —$OCH_3$, —$OCH_2CH_3$, —$OCH(CH_3)_2$, —$OCH_2CF_3$, —$CH_2$—$S(O)_2$—$CH_3$, dimethylamino, $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl.

$R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, or $R^1$ and $R^2$ together with the carbon atom to which they are bonded form a 4- or 5-membered carbocycle, and $R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably $R^1$ and $R^2$ together with the carbon atom to which they are bonded form a cyclopentyl, or $R^3$ and $R^4$ together with the carbon atom to which they are bonded form a 3-, 4- or 5-membered carbocycle, and $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, preferably $R^3$ and $R^4$ together with the carbon atom to which they are bonded form a cyclopropyl or a cyclobutyl, or $R^2$ and $R^4$ together with the carbon atom to which they are bonded form a 3-, 4- or 5-membered non-aromatic carbocycle optionally substituted by substituents selected from the group consisting of one to four $C_1$-$C_3$-alkyl groups and one to two halogen atoms, and $R^1$ is selected from the group consisting of hydrogen halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and $R^3$ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably $R^2$ and $R^4$ together with the carbon atom to which they are bonded form a cyclopropyl, cyclobutyl or cyclopentyl, or $R^1$ and $R^3$ together with the carbon atom to which they are bonded form a 3-, 4- or 5-membered non-aromatic carbocycle optionally substituted by substituents selected from the group consisting of one to four $C_1$-$C_3$-alkyl groups and one to two halogen atoms, preferably cyclopropyl, cyclobutyl or cyclopentyl, and $R^2$ is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)$C_1$-$C_4$-alkyl, —NHC(O)—$C_1$-$C_4$-alkyl, 2,6-dichlorophenyl-carbonylamino, 2-chlorophenyl-carbonylamino and phenyl, and $R^4$ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably $R^1$ and $R^3$ together with the carbon atom to which they are bonded form a cyclopropyl, cyclobutyl or cyclopentyl, $R^5$ is selected from the group consisting of hydrogen, $C_3$-$C_6$-cycloalkyl, $C_1$-$C_4$-alkylcarbonyl, $C_1$-$C_4$-alkoxycarbonyl, A represents a phenyl group of formula (A1)

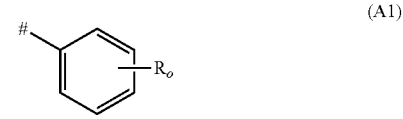

(A1)

wherein
o is 0, 1 or 2, and
each R is independently selected from the group consisting of halogen, nitro, —OH, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1C_1$-$C_4$-alkoxycarbonyl, —NH($C_1$-$C_4$-alkyl), phenyl (optionally substituted by $C_1$-$C_4$-alkoxy) and phenoxy, or A represents a heterocycle of the formula (Het-1)

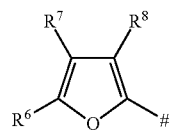
(Het-1)

in which
$R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and $R^8$ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

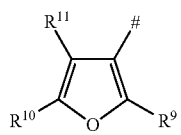
(Het-2)

in which
$R^9$ is selected from the group consisting of hydrogen, halogen, $C_1$-$C_4$-alkyl and $C_1$-$C_4$-halogenoalkyl having 1 to 5 halogen atoms, and $R^{10}$ and $R^{11}$ may be the same or different and are selected from the group consisting of hydrogen, halogen, $C_1$-$C_4$-alkyl and $C_1$-$C_4$-halogenoalkyl having 1 to 5 halogen atoms, phenyl optionally substituted by halogen or $C_1$-$C_4$-alkyl), or A represents a heterocycle of the formula (Het-4)

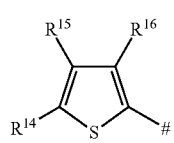
(Het-4)

in which
$R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and $R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A represents a heterocycle of the formula (Het-5)

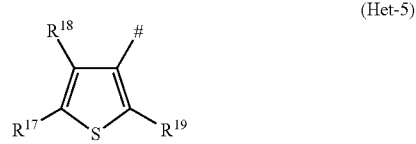
(Het-5)

in which
$R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and $R^{19}$ is selected from the group consisting of hydrogen, halogen, $C_1$-$C_4$-alkyl and $C_1$-$C_4$-halogenoalkyl having 1 to 5 atoms, or A represents a heterocycle of the formula (Het-6)

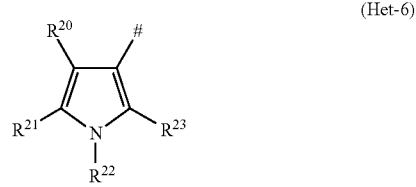
(Het-6)

in which
$R^{20}$ is selected from the group consisting of hydrogen, halogen, cyano, $C_1$-$C_4$-alkyl and $C_1$-$C_4$-halogenoalkyl having 1 to 5 halogen atoms, and $R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and $R^{22}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, or A represents a heterocycle of the formula (Het-10)

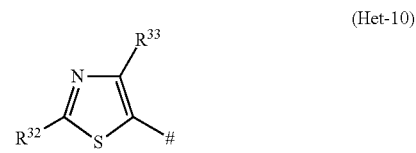
(Het-10)

in which
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and $R^{33}$ is selected from the group consisting of halogen, $C_1$-$C_4$-alkyl and $C_1$-$C_4$-halogenoalkyl having 1 to 5 halogen atoms, $C_1$-$C_3$-halogenoalkoxy comprising 1 to 9 halogen atoms, amino, substituted or unsubstituted $C_1$-$C_5$-alkylamino or substituted or unsubstituted di-($C_1$-$C_5$-alkyl)-amino, or A represents a heterocycle of the formula (Het-21)

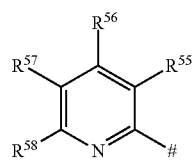

in which

R⁵⁵ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and R⁵⁶, R⁵⁷ and R⁵⁸, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-22)

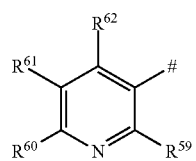

in which

R⁵⁹ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, —S(O)—$C_1$-$C_4$-alkyl, —S(O)$_2$—$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), and R⁶⁰, R⁶¹ and R⁶², which may the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or a $C_1$-$C_4$-alkyl), or A represents a heterocycle of the formula (Het-29)

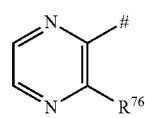

in which

R⁷⁶ is selected from the group consisting of hydrogen, halogen, $C_1$-$C_4$-alkyl and $C_1$-$C_4$-halogenoalkyl having 1 to 5 halogen atoms.

In another individual aspect of embodiment 3-1, R¹ is fluorine. In another individual aspect of embodiment 3-1, R² is fluorine. In another individual aspect of embodiment 3-1, R¹ is fluorine and R² is fluorine. In another individual aspect of embodiment 3-1, the combination R¹/R² is fluorine/methyl.

In another individual aspect of embodiment 3-2, R¹ is fluorine. In another individual aspect of embodiment 3-2, R² is fluorine. In another individual aspect of embodiment 3-2, R¹ is fluorine and R² is fluorine. In another individual aspect of embodiment 3-2, the combination R¹/R² is fluorine/methyl.

Especially preferred substituents or ranges of the structural elements mentioned in the compounds of formula (I) are explained below (embodiment 4-1).

B¹ represents N,
B² represents CH,
n is 1,
X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms,
Q is selected from:

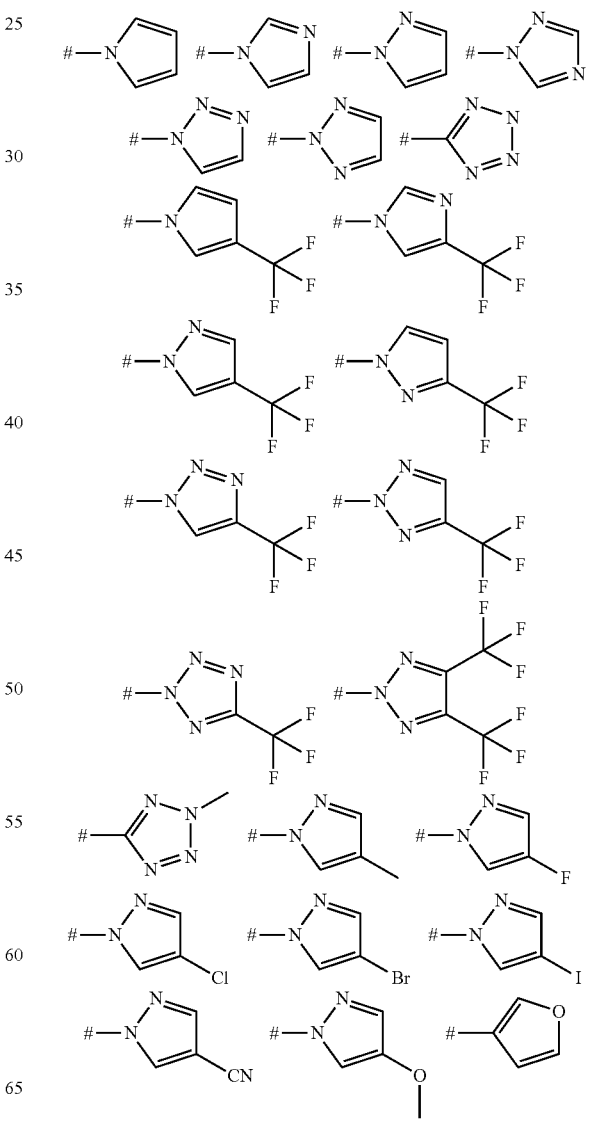

-continued
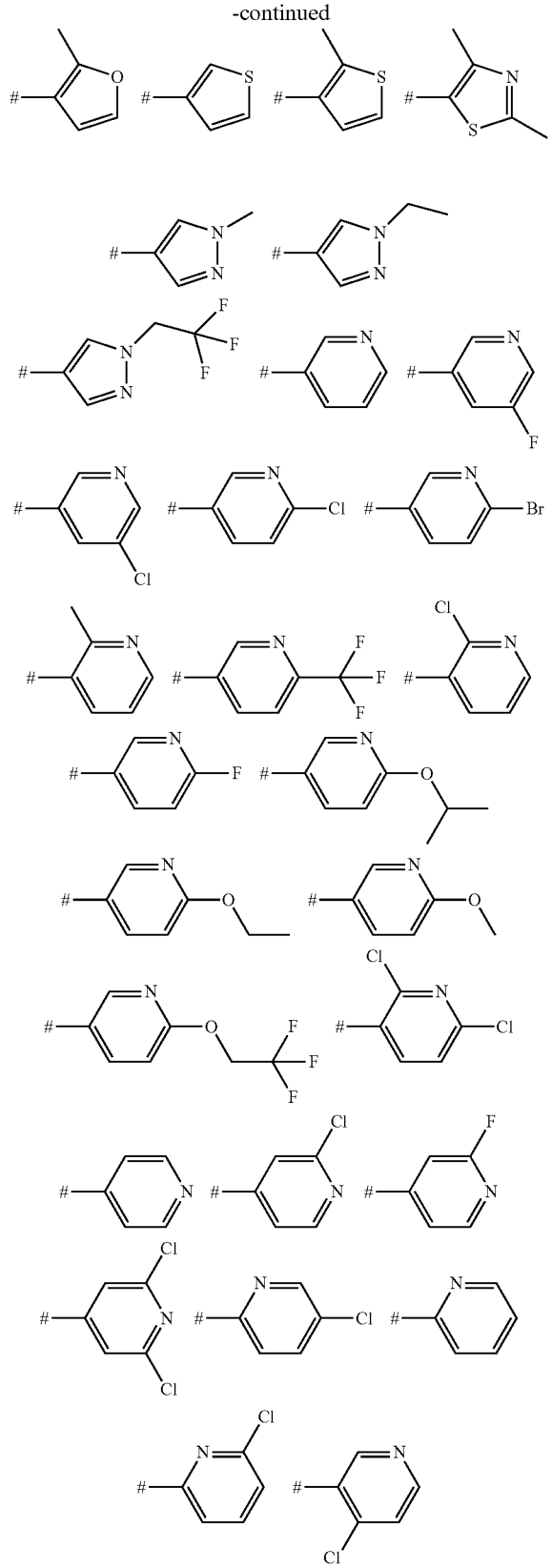
R¹ and R² are the same or different and are selected from the group consisting of hydrogen, methyl, ethyl, methoxy, ethoxy or fluorine,
R³ and R⁴ are the same or different and are selected from the group consisting of hydrogen, methyl or ethyl,
R⁵ is hydrogen,
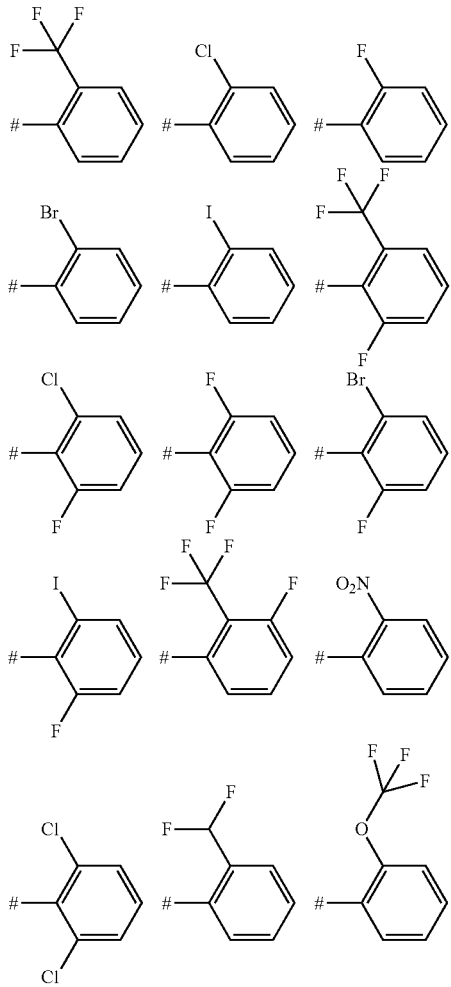
or
A is selected from:
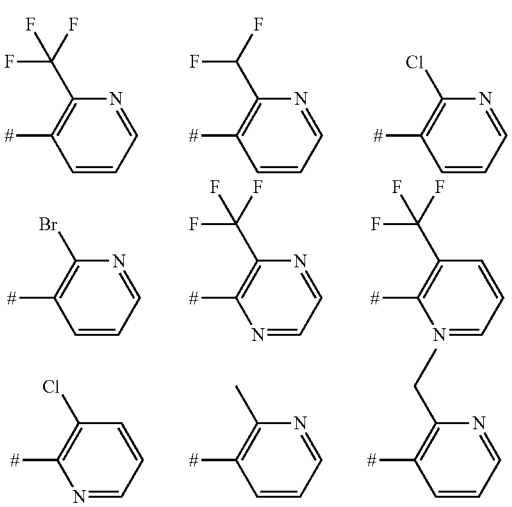

-continued

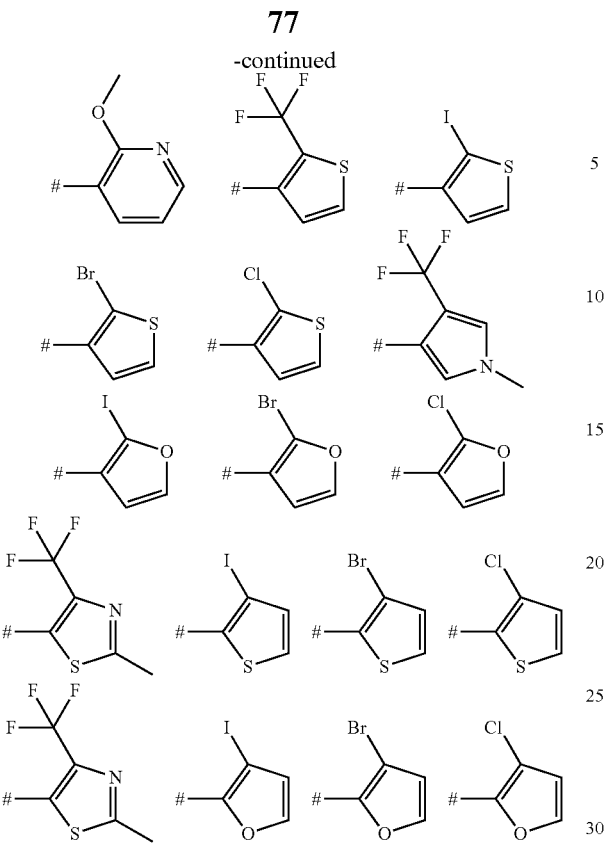

In an individual embodiment (embodiment 4-2), the structural elements in the compound of formula (I) are especially preferably defined as follows:

$B^1$ represents N,
$B^2$ represents CH,
n is 1.
X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms,
Q is selected from:

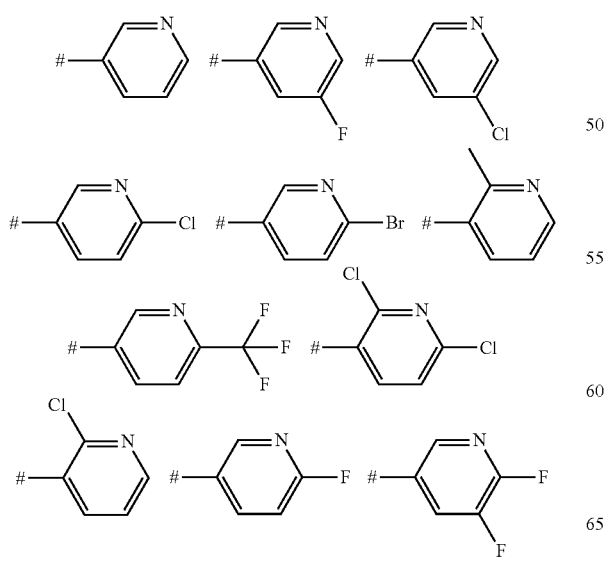

-continued

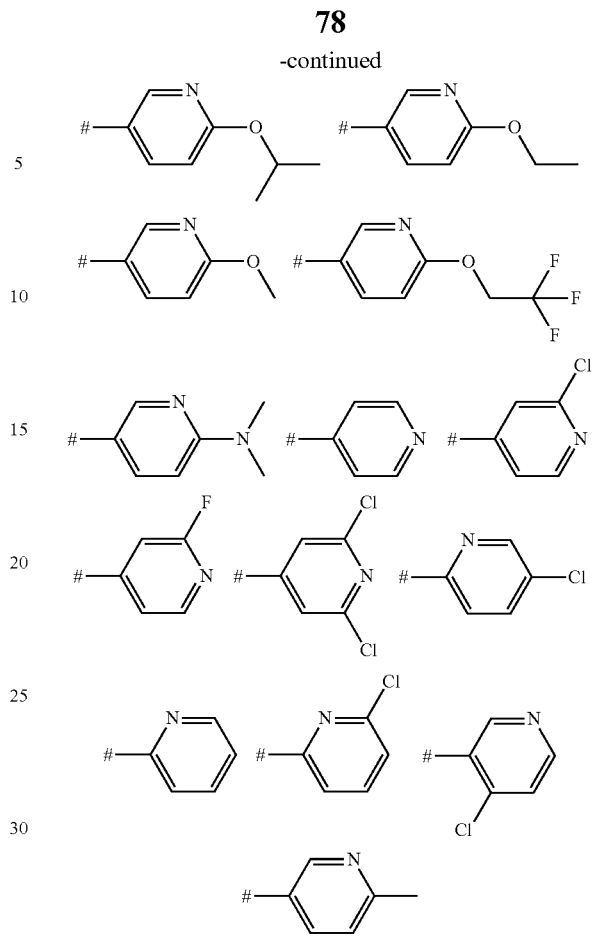

$R^1$ and $R^2$ are the same or different and are selected from the group consisting of hydrogen, methyl, ethyl, methoxy, ethoxy or fluorine,
$R^3$ and $R^4$ are the same or different and are selected from the group consisting of hydrogen, methyl or ethyl,
$R^5$ is hydrogen,
A is selected from:

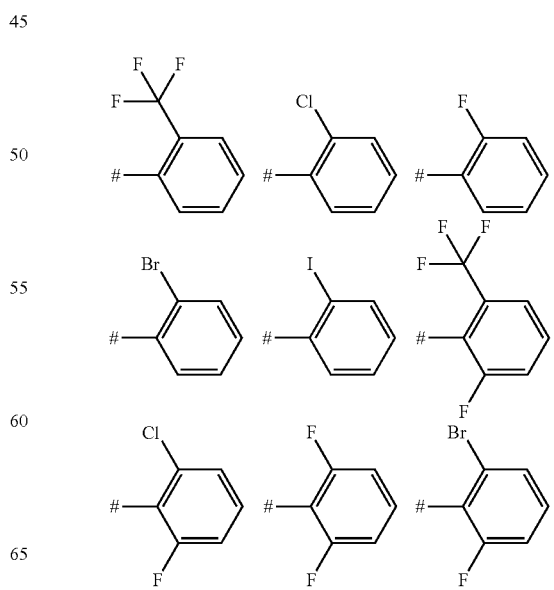

-continued

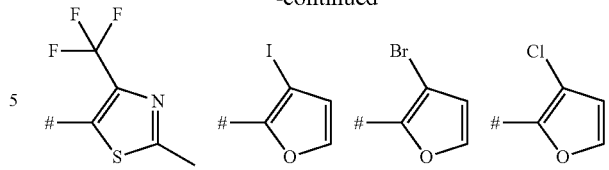

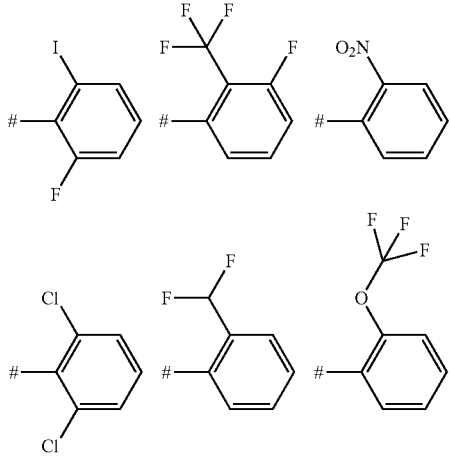

or
A is selected from:

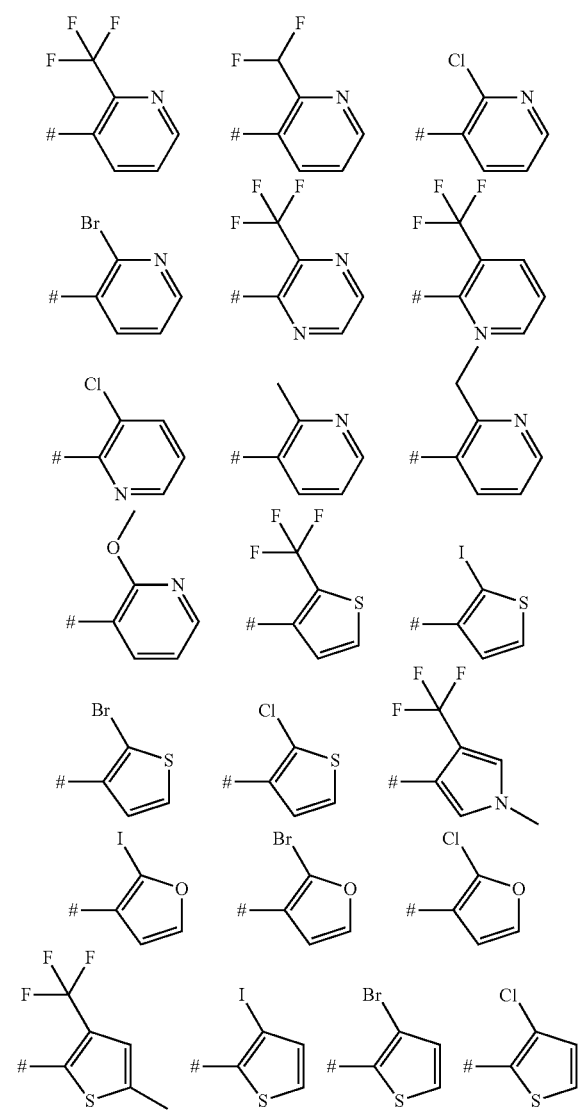

In another individual aspect of embodiment 4-1, $R^1$ is fluorine. In another individual aspect of embodiment 4-1, $R^2$ is fluorine. In another individual aspect of embodiment 4-1, $R^1$ is fluorine and $R^2$ is fluorine. In another individual aspect of embodiment 4-1, the combination $R^1/R^2$ is fluorine/methyl.

In another individual aspect of embodiment 4-2, $R^1$ is fluorine. In another individual aspect of embodiment 4-2, $R^2$ is fluorine. In another individual aspect of embodiment 4-2, $R^1$ is fluorine and $R^2$ is fluorine. In another individual aspect of embodiment 4-2, the combination $R^1/R^2$ is fluorine/methyl.

Alternatively, especially preferred substituents or ranges of the structural elements mentioned in the compounds of formula (I) are explained below (embodiment 4-3).

$B^1$ represents N,
$B^2$ represents CH.
n is 1,
X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms,
Q is selected from:

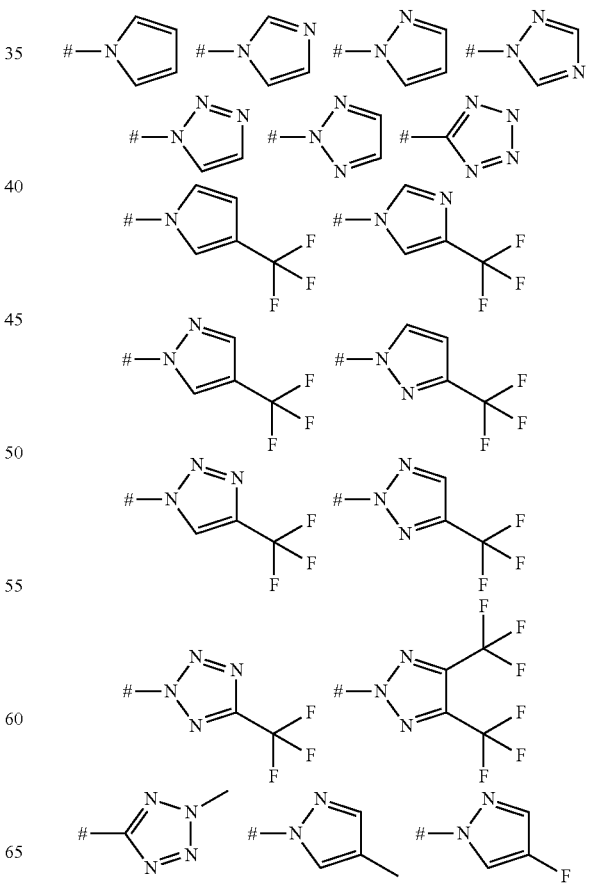

-continued
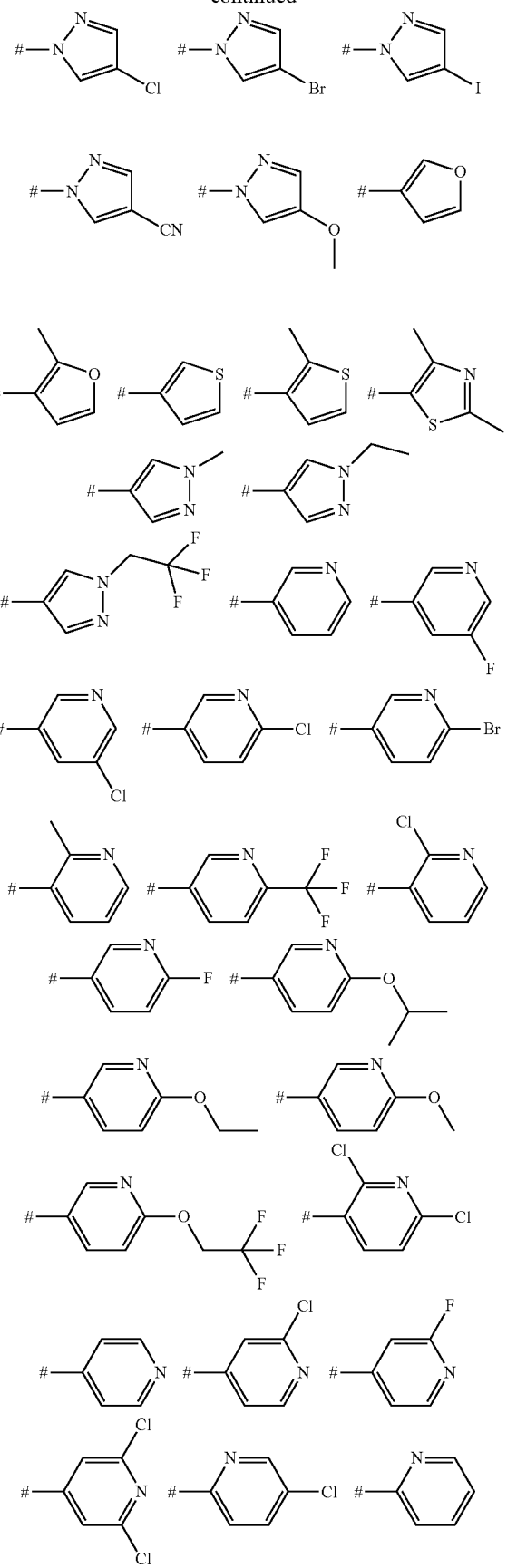
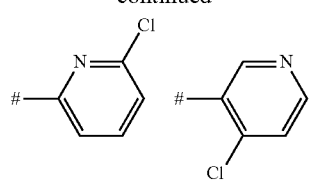
R[1] is selected from the group consisting of hydrogen, methyl, ethyl, methoxy, ethoxy or fluorine,
R[3] is selected from the group consisting of hydrogen, methyl or ethyl,
R[2] and R[4] together with the carbon atom to which they are bonded form a cyclobutane,
R[5] is hydrogen,
A is selected from:
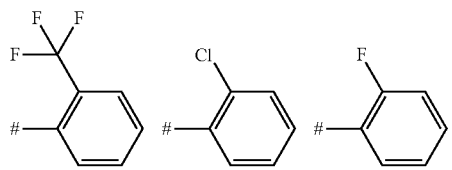
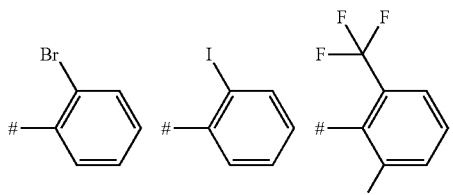
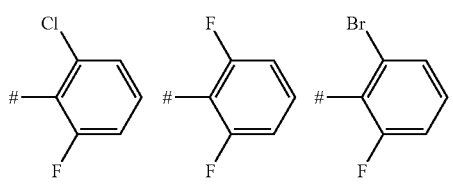
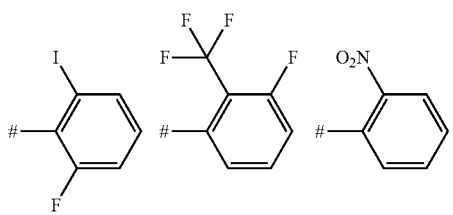

-continued

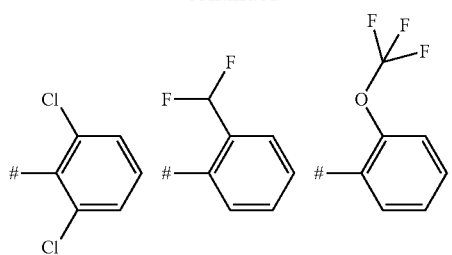

or

A is selected from:

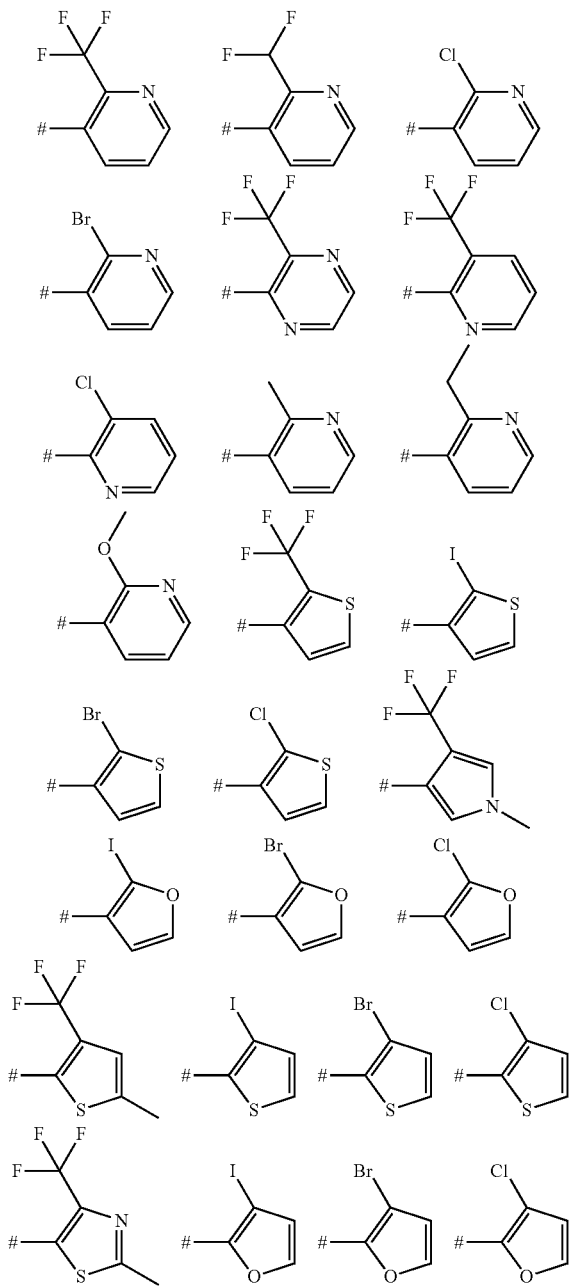

In an individual embodiment (embodiment 4-4), the structural elements in the compound of formula (I) are especially preferably defined as follows:

$B^1$ represents N,
$B^2$ represents CH,
n is 1.
X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms,
Q is selected from:

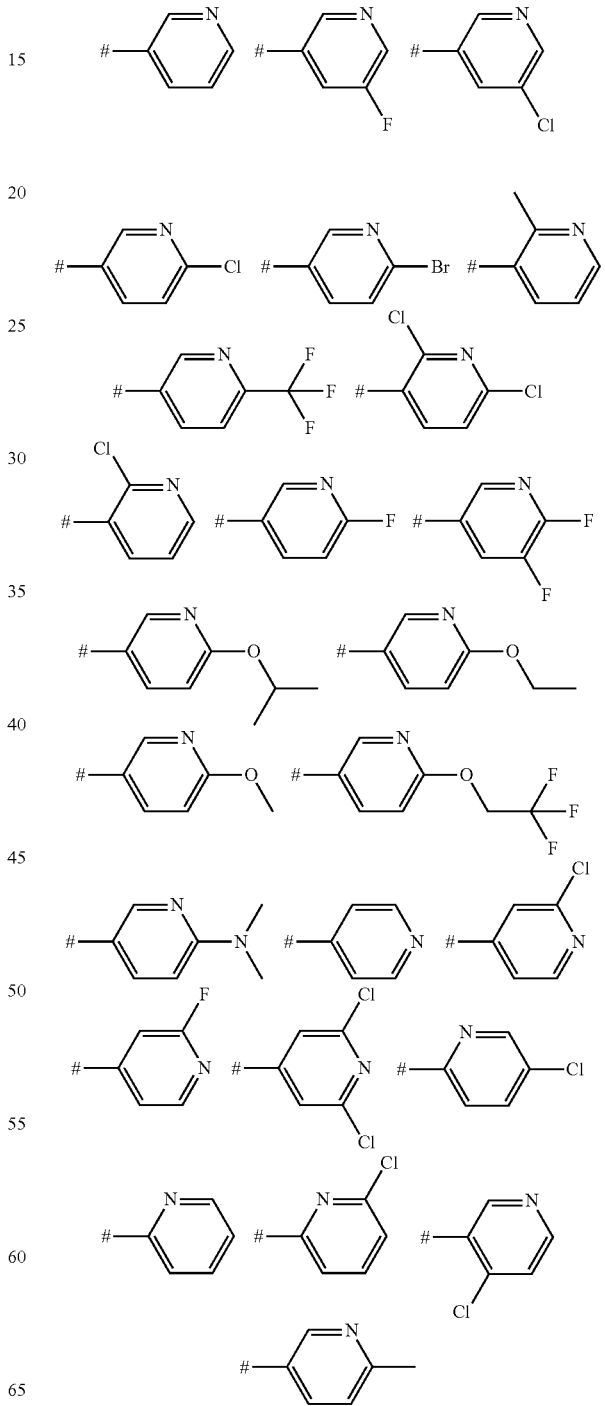

R¹ is selected from the group consisting of hydrogen, methyl, ethyl, methoxy, ethoxy or fluorine,
R³ is selected from the group consisting of hydrogen, methyl or ethyl.
R² and R⁴ together with the carbon atom to which they are bonded form a cyclobutane.
R⁵ is hydrogen,
A is selected from:

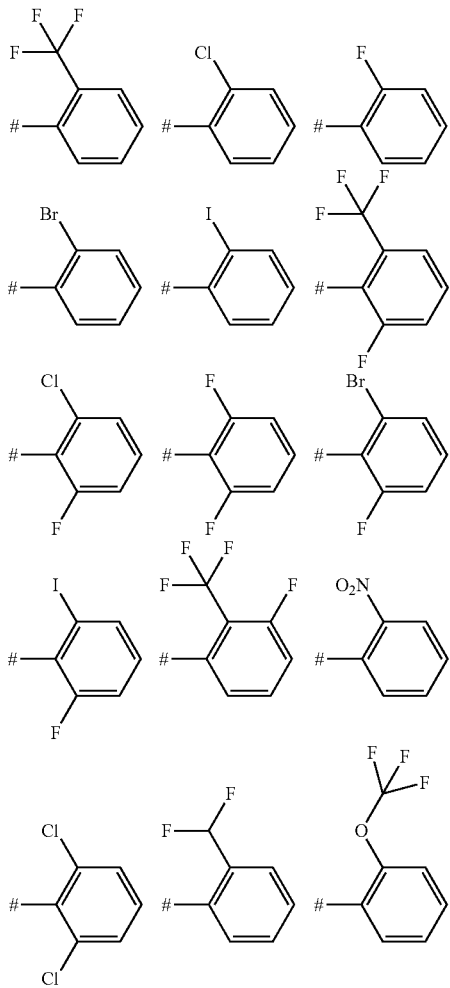

or
A is selected from:

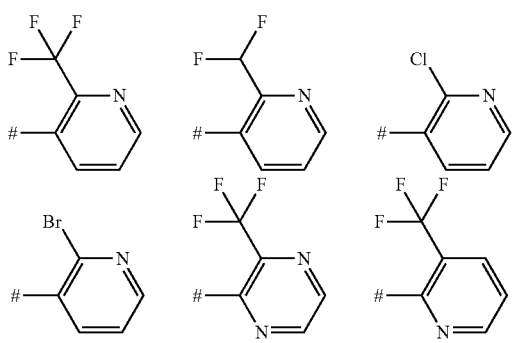

-continued

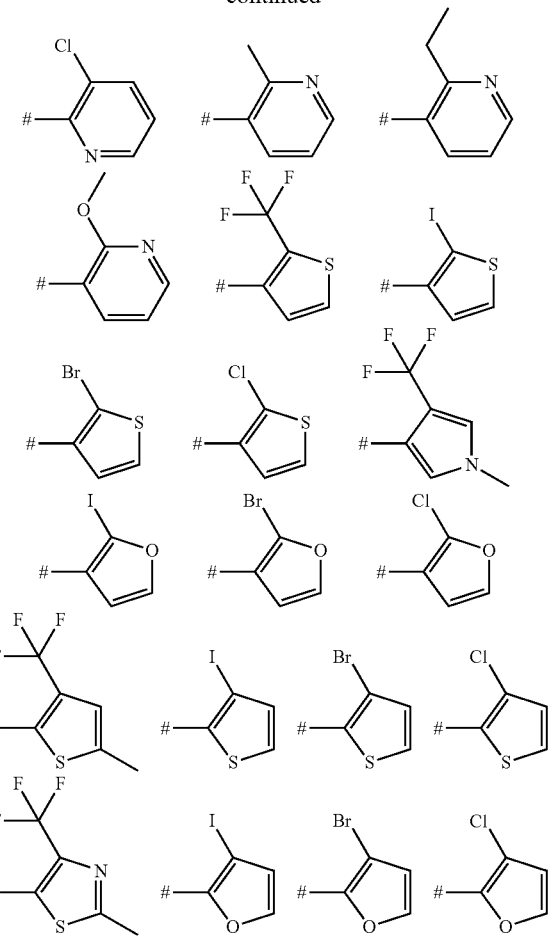

In another individual aspect of embodiment 4-3, R¹ is fluorine.
In another individual aspect of embodiment 4-4, R¹ is fluorine.
In a very specific aspect (embodiment 5-1) of the especially preferred substituents or ranges of the structural elements mentioned in the compounds of formula (I),
B¹ represents N.
B² represents CH.
n is 1,
X is selected from the group consisting of hydrogen or chlorine.
Q is selected from:

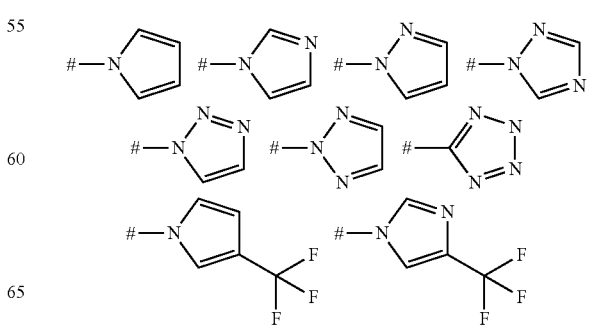

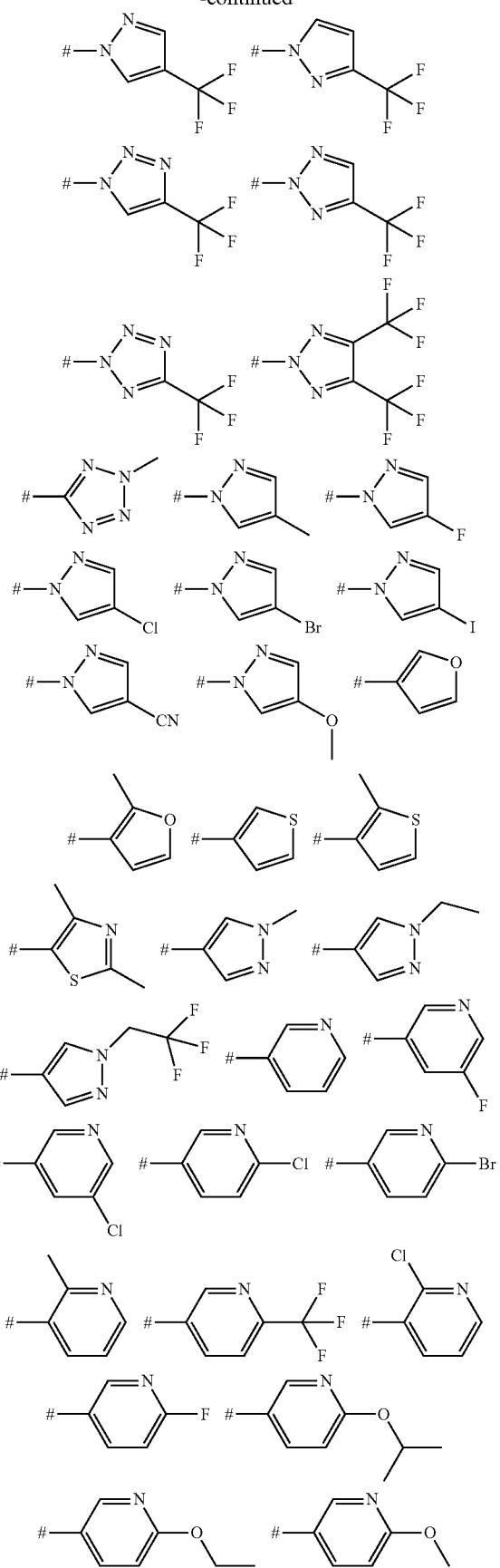

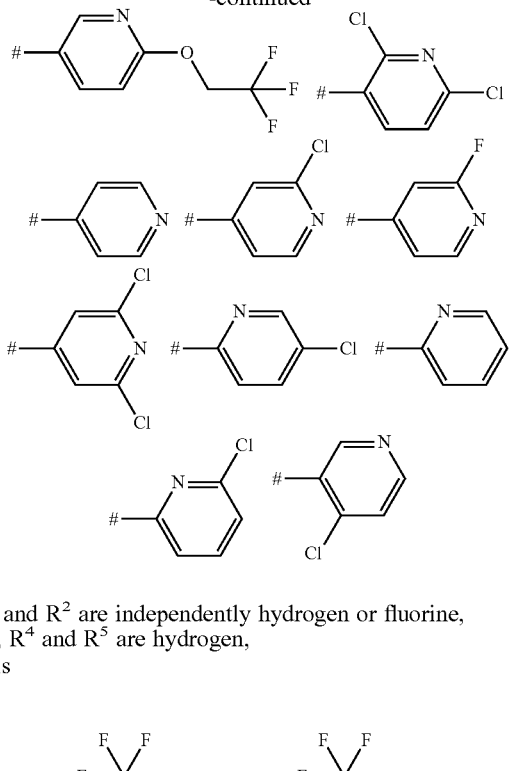

R$^1$ and R$^2$ are independently hydrogen or fluorine,
R$^3$, R$^4$ and R$^5$ are hydrogen,
A is

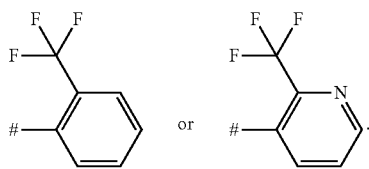

In another very specific aspect (embodiment 5-2) of the especially preferred substituents or ranges of the structural elements mentioned in the compounds of formula (I).
B$^1$ represents N,
B$^2$ represents CH.
n is 1,
X is selected from the group consisting of hydrogen or chlorine,
Q is selected from:

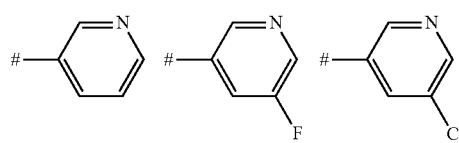

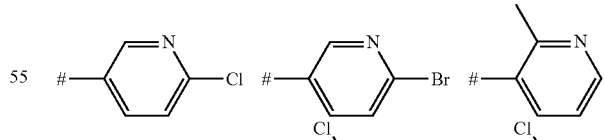

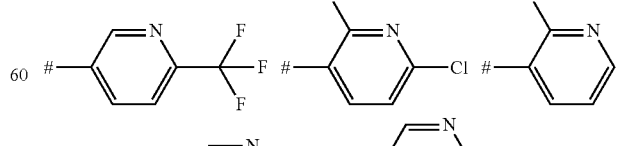

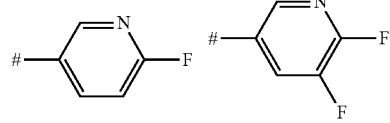

-continued

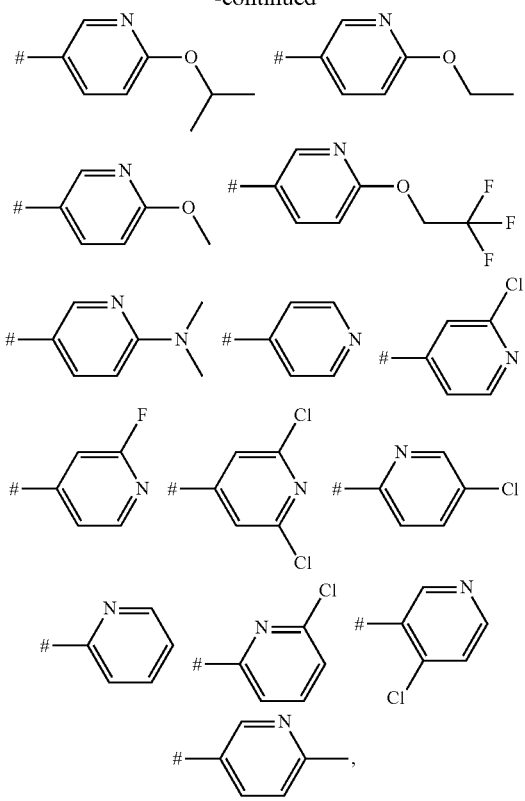

R¹ and R² are independently hydrogen, methyl or fluorine,
R³, R⁴ and R¹ are hydrogen,
A is

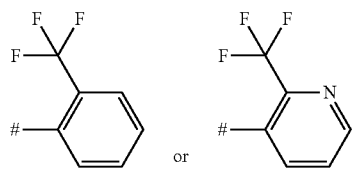

In another very specific aspect (embodiment 5-3) of the especially preferred substituents or ranges of the structural elements mentioned in the compounds of formula (I),
B¹ represents N,
B² represents CH,
n is 1,
X is selected from the group consisting of hydrogen or chlorine;
Q is selected from:

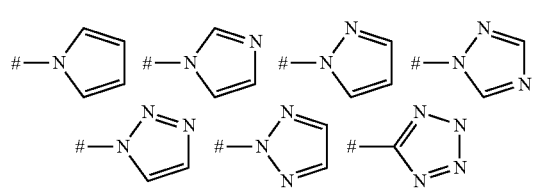

-continued

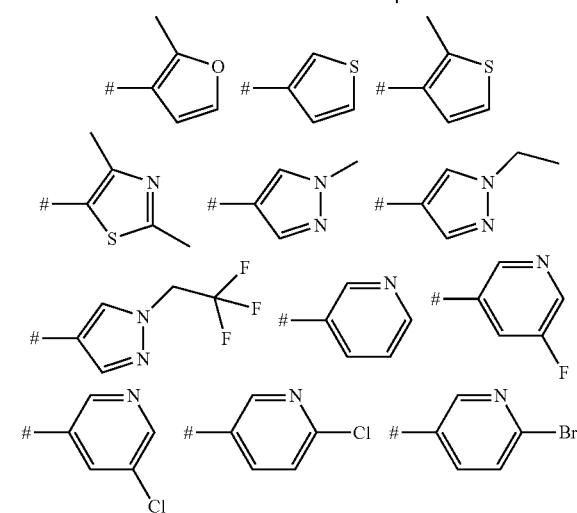

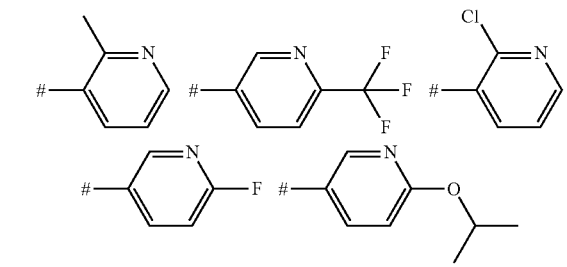

-continued

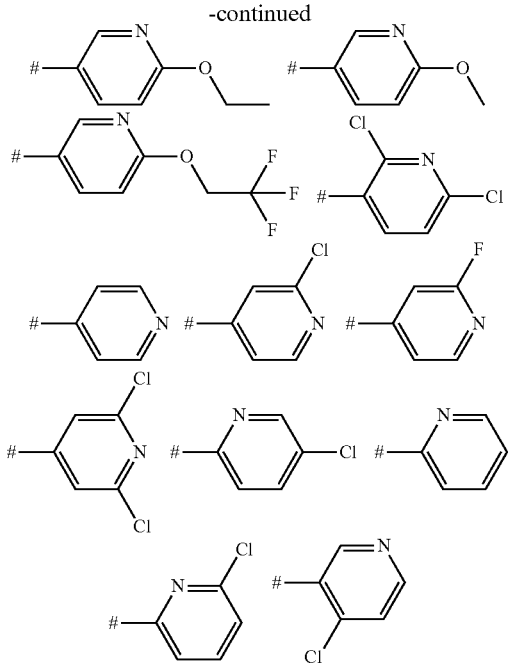

R$^1$ is hydrogen or fluorine.
R$^3$ and R$^5$ are hydrogen,
R$^2$ and R$^4$ together with the carbon atom to which they are bonded form a cyclobutane.
A is

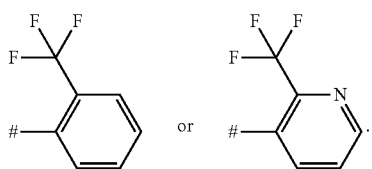

In another very specific aspect (embodiment 5-4) of the especially preferred substituents or ranges of the structural elements mentioned in the compounds of formula (I),
B$^1$ represents N,
B$^2$ represents CH,
n is 1.
X is selected from the group consisting of hydrogen or chlorine:
Q is selected from:

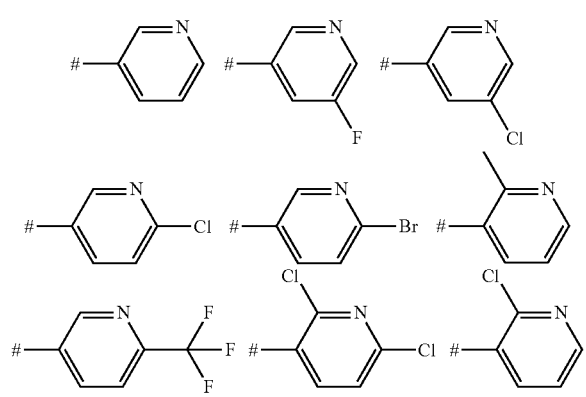

-continued

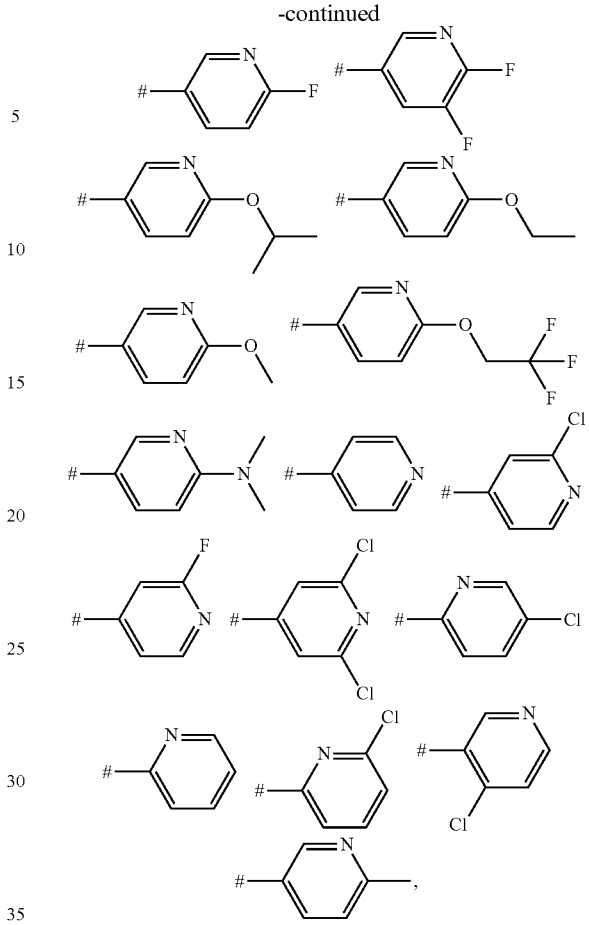

R$^1$ is hydrogen, methyl or fluorine,
R$^3$ and R$^5$ are hydrogen,
R$^2$ and R$^4$ together with the carbon atom to which they are bonded form a cyclobutane,
A is

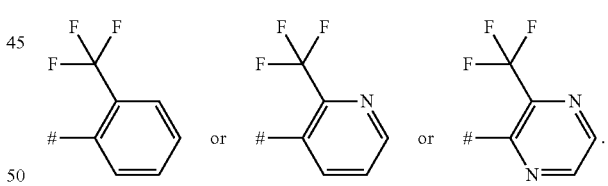

In another individual aspect of embodiment 5-1, R$^1$ is fluorine. In another individual aspect of embodiment 5-1, R$^2$ is fluorine. In another individual aspect of embodiment 5-1, R$^1$ is fluorine and R$^2$ is fluorine.

In another individual aspect of embodiment 5-2, R$^1$ is fluorine. In another individual aspect of embodiment 5-2, R$^2$ is fluorine. In another individual aspect of embodiment 5-2, R$^1$ is fluorine and R$^2$ is fluorine. In another individual aspect of embodiment 5-2, the combination R$^1$/R$^2$ is fluorine/methyl.

In another individual aspect of embodiment 5-3, R$^1$ is fluorine.

In another individual aspect of embodiment 5-4, R$^1$ is fluorine. In another individual aspect of embodiment 5-4, R$^1$ is methyl.

The definitions of radicals, and explanations, that are given above in general or in ranges of preference may be combined arbitrarily with one another, thus including combinations between the respective ranges and ranges of preference. The definitions and explanations apply to the end products and also to the precursors and intermediates accordingly.

Preferred in accordance with the invention are the compounds of the formula (I) in which there is a combination of the definitions given above as being preferred (preferably), wherein each embodiment described above as being preferred constitutes an individual combination.

More preferred in accordance with the invention are the compounds of the formula (I) in which there is a combination of the definitions given above as being more preferred (more preferably), wherein each embodiment described above as being more preferred constitutes an individual combination.

Especially preferred in accordance with the invention are the compounds of the formula (I) in which there is a combination of the definitions given above as being especially preferred (especially preferably), wherein each embodiment described above as being especially preferred constitutes an individual combination.

A very specific aspect in accordance with the invention are the compounds of the formula (I) in which there is a combination of the definitions given above as being a first very specific aspect (embodiment 5-1) of the especially preferred substituents or ranges of the structural elements.

Another very specific aspect in accordance with the invention are the compounds of the formula (I) in which there is a combination of the definitions given above as being a second very specific aspect (embodiment 5-2) of the especially preferred substituents or ranges of the structural elements.

Another very specific aspect in accordance with the invention are the compounds of the formula (I) in which there is a combination of the definitions given above as being a third very specific aspect (embodiment 5-3) of the especially preferred substituents or ranges of the structural elements.

Another very specific aspect in accordance with the invention are the compounds of the formula (I) in which there is a combination of the definitions given above as being a fourth very specific aspect (embodiment 5-4) of the especially preferred substituents or ranges of the structural elements.

Saturated or unsaturated hydrocarbon radicals such as alkyl, alkanediyl or alkenyl may in each case, both alone and in conjunction with heteroatoms, as in alkoxy, for example, be—where possible—either straight-chain or branched.

Any substituted radicals may, unless indicated otherwise, be substituted one or more times, and the substituents in the case of multiple substitutions may be alike or different.

In the definitions of radicals that are stated as being preferred, halogen (halo) is fluoro, chloro, bromo and iodo, very preferably fluoro, chloro and bromo, and especially preferably fluoro and chloro.

Further specific embodiments of the invention are described hereafter.

A specific embodiment (embodiment 6-1) of the invention is a compound of the formula (I-1)

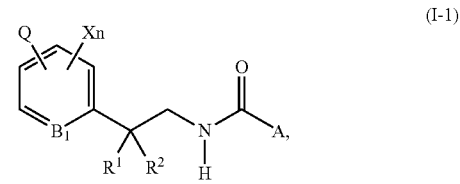

(I-1)

in which $B_1$ is N and $R^1$, $R^2$, Q, X, n and A are as defined above in embodiment 1-1.

Another specific embodiment (embodiment 6-2) of the invention is a compound of the formula (I-1)

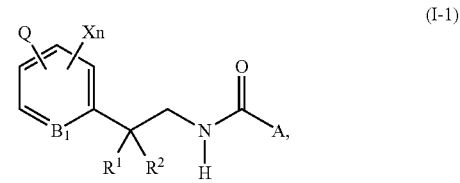

(I-1)

in which $B_1$ is N and $R^1$, $R^2$, Q, X, n and A are as defined above in embodiment 1-2.

Another specific embodiment (embodiment 7-1) of the invention is a compound of the formula (I-1)

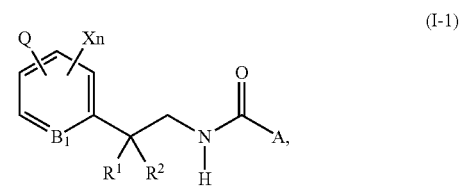

(I-1)

in which $B_1$ is N and $R^1$, $R^2$, Q, X, n and A are as defined above in embodiment 2-1.

Another specific embodiment (embodiment 7-2) of the invention is a compound of the formula (I-1)

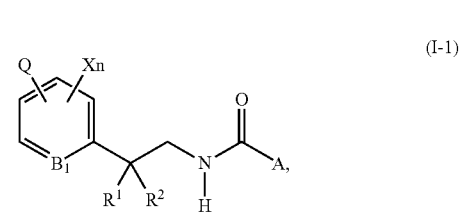

(I-1)

in which $B_1$ is N and $R^1$, $R^2$, Q, X, n and A are as defined above in embodiment 2-2.

Another specific embodiment (embodiment 8-1) of the invention is a compound of the formula (I-1)

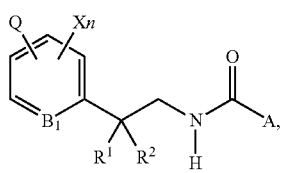

in which $B_1$ is N and $R^1$, $R^2$, Q, X, n and A are as defined above in embodiment 3-1.

Another specific embodiment (embodiment 8-2) of the invention is a compound of the formula (I-1)

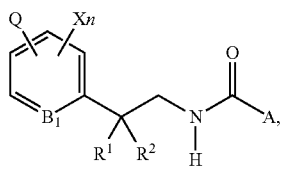

in which $B_1$ is N and $R^1$, $R^2$, Q, X, n and A are as defined above in embodiment 3-2.

Another specific embodiment (embodiment 9-1) of the invention is a compound of the formula (I-1)

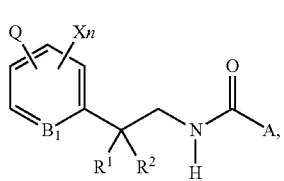

in which $B_1$ is N and $R^1$, $R^2$, Q, X, n and A are as defined above in embodiment 4-1.

Another specific embodiment (embodiment 9-2) of the invention is a compound of the formula (I-1)

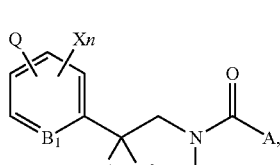

in which $B_1$ is N and $R^1$, $R^2$, Q, X, n and A are as defined above in embodiment 4-2.

Another specific embodiment (embodiment 9-3) of the invention is a compound of the formula (I-1)

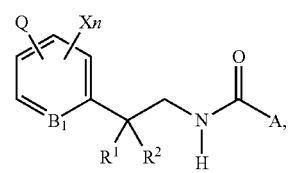

in which $B_1$ is N and $R^1$, $R^2$, Q, X, n and A are as defined above in embodiment 4-3.

Another specific embodiment (embodiment 9-4) of the invention is a compound of the formula (I-1)

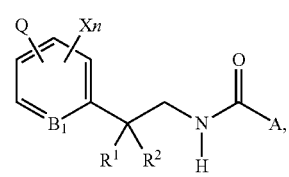

in which $B_1$ is N and $R^1$, $R^2$, Q, X, n and A are as defined above in embodiment 4-4.

Another specific embodiment (embodiment 10-1) of the invention is a compound of the formula (I-1)

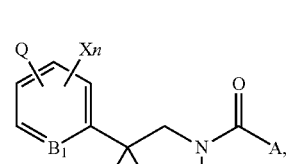

in which $B_1$ is N and $R^1$, $R^2$, Q, X, n and A are as defined above in embodiment 5-1.

Another specific embodiment (embodiment 10-2) of the invention is a compound of the formula (I-1)

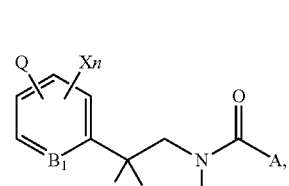

in which $B_1$ is N and $R^1$, $R^2$, Q, X, n and A are as defined above in embodiment 5-2.

Another specific embodiment (embodiment 10-3) of the invention is a compound of the formula (I-1)

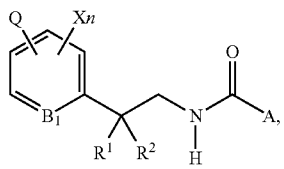

(I-1)

in which $B_1$ is N and $R^1$, $R^2$, Q, X, n and A are as defined above in embodiment 5-3.

Another specific embodiment (embodiment 10-4) of the invention is a compound of the formula (I-1)

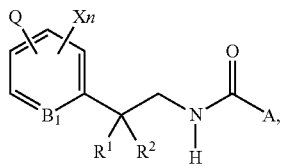

(I-1)

in which $B_1$ is N and $R^1$, $R^2$, Q, X, n and A are as defined above in embodiment 5-4.

In embodiment 1-1 as well as in each individual aspect of said embodiment, Q preferably is in para-position.

In embodiment 1-2 as well as in each individual aspect of said embodiment, Q preferably is in para-position.

In embodiment 2-1 as well as in each individual aspect of said embodiment, Q preferably is in para-position.

In embodiment 2-2 as well as in each individual aspect of said embodiment, Q preferably is in para-position.

In embodiment 3-1 as well as in each individual aspect of said embodiment, Q preferably is in para-position.

In embodiment 3-2 as well as in each individual aspect of said embodiment, Q preferably is in para-position.

In embodiment 4-1 as well as in each individual aspect of said embodiment, Q preferably is in para-position.

In embodiment 4-2 as well as in each individual aspect of said embodiment, Q preferably is in para-position.

In embodiment 4-3 as well as in each individual aspect of said embodiment, Q preferably is in para-position.

In embodiment 4-4 as well as in each individual aspect of said embodiment, Q preferably is in para-position.

In embodiment 5-1 as well as in each individual aspect of said embodiment, Q preferably is in para-position.

In embodiment 5-2 as well as in each individual aspect of said embodiment, Q preferably is in para-position.

In embodiment 5-3 as well as in each individual aspect of said embodiment, Q preferably is in para-position.

In embodiment 5-4 as well as in each individual aspect of said embodiment, Q preferably is in para-position.

In embodiment 6-1 as well as in each individual aspect of said embodiment, Q preferably is in para-position.

In embodiment 6-2 as well as in each individual aspect of said embodiment, Q preferably is in para-position.

In embodiment 7-1 as well as in each individual aspect of said embodiment, Q preferably is in para-position.

In embodiment 7-2 as well as in each individual aspect of said embodiment, Q preferably is in para-position.

In embodiment 8-1 as well as in each individual aspect of said embodiment, Q preferably is in para-position.

In embodiment 8-2 as well as in each individual aspect of said embodiment, Q preferably is in para-position.

In embodiment 9-1 as well as in each individual aspect of said embodiment, Q preferably is in para-position.

In embodiment 9-2 as well as in each individual aspect of said embodiment, Q preferably is in para-position.

In embodiment 9-3 as well as in each individual aspect of said embodiment, Q preferably is in para-position.

In embodiment 9-4 as well as in each individual aspect of said embodiment, Q preferably is in para-position.

In embodiment 10-1 as well as in each individual aspect of said embodiment, Q preferably is in para-position.

In embodiment 10-2 as well as in each individual aspect of said embodiment, Q preferably is in para-position.

In embodiment 10-3 as well as in each individual aspect of said embodiment, Q preferably is in para-position.

In embodiment 10-4 as well as in each individual aspect of said embodiment, Q preferably is in para-Position.

Procedures and Methods

The synthesis of the compounds of the formula (I) can be performed according to or in analogy to scheme 1 or scheme 2. The required starting materials are known or accessible via generally known procedures which are described in more detail in WO 2001/011965 A1 (P1). WO 2005/058828 A1 (P2), WO2005/014545 A2 (P3). WO 2005/103004 A1 (P4), WO 2006/122952 A1 (P5), EP 2 289 880 A1 (P6), WO 2006/008191 A1 (P7). WO 2006/008192 A1 (P8). WO 2004/074280 A1 (P9), WO 2005/058833 A2 (P10). WO 2005/085238 A1 (P11). WO 2005/103006 A1 (P12), WO 2006/122955 A1 (P13). WO 2006/008194 A1 (P14). WO 2006/008193 A1 (P15). WO 2006/067103 A2 (P16) and in case of $R^1=R^2=$fluorine WO 2013/064460.

Dichlorobromopyridine (VI) is synthesized from 2-hydroxy-5-nitroaniline (II) using the procedure described in US2004/242644 A and Synthesis 1990, 499. The synthesis of the nitrile (VIII) is performed as described in EP1674455 A1 or EP1548007 A1, followed by reduction to the boc-protected amine (IX) with sodium borohydride in the presence of nickel chloride and Boc Anhydride. (IX) is then cleaved with hydrogen chloride in methanol to the amine-hydrochloride (X). The synthesis of the amine (XVII) is performed in analogy to the procedure described in WO 2013/064460 A1 (referred as intermediates IIa-14 and IIa-15).

The amine-hydrochloride (X) or the amine (XVII) is then coupled with the appropriate acid and a coupling reagent such as HOBT-EDC to yield for example the amide (XI) or (XVIII), wherein $B^3$ represents N or CH and $R_o$ is defined as described before.

The compounds of the formula (I-a) or (I-b) are then synthesized by a coupling reaction. In the case of Q=N-bonded azoles, a copper-mediated process with copper(I)-oxide, salicyladoxime as ligand in a solvent as acetonitrile in the presence of a base as cesium carbonate may be used. In the case of Q=carbon-bonded heterocycles, a Suzuki-type coupling with the appropriate boronic acid or ester in the presence of a palladium catalyst and a base may be used.

Further compounds with Q=triazole of the formula (I) are accessible via conversion of the amine (V) to the corresponding hydrazine via diazotation—reduction and subsequent triazole formation as described in US2011/77410 A1. Compounds with Q=tetrazole are accessible via conversion of the amine (V) into the corresponding nitrile via diazotation—cyanation and subsequent cycloaddition with azide.

Scheme 1:
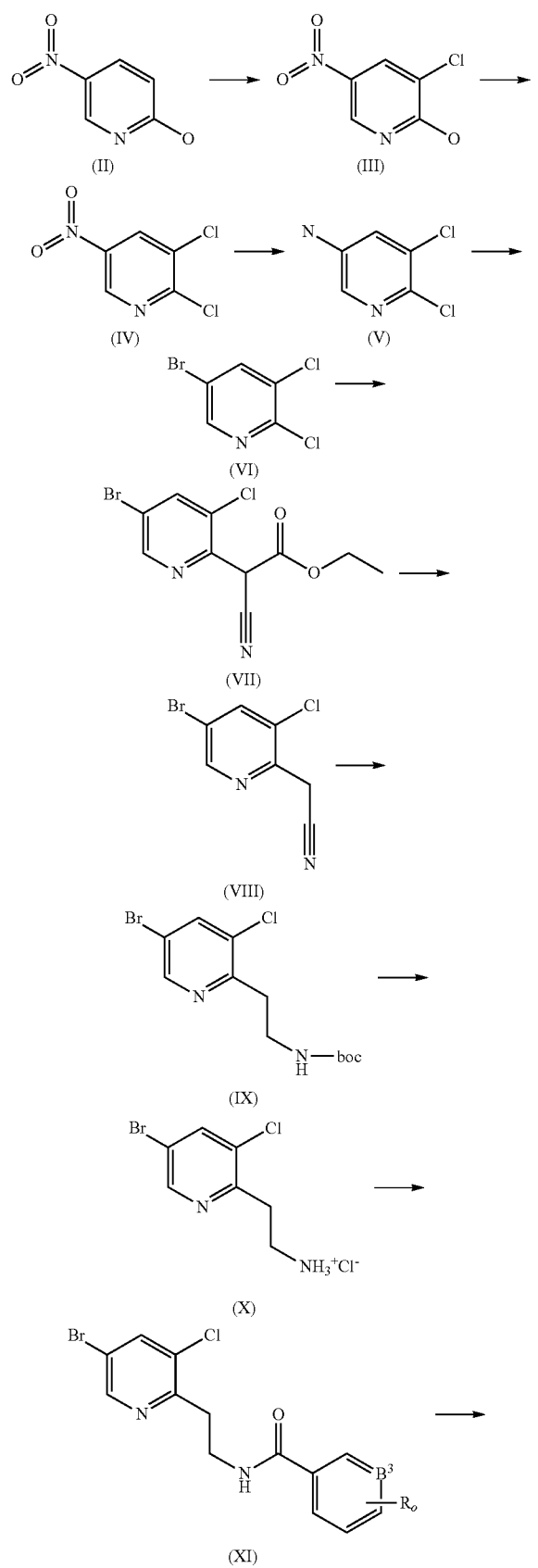
-continued
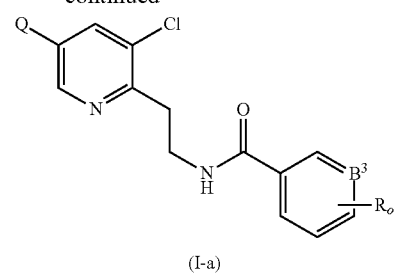
Scheme 2:
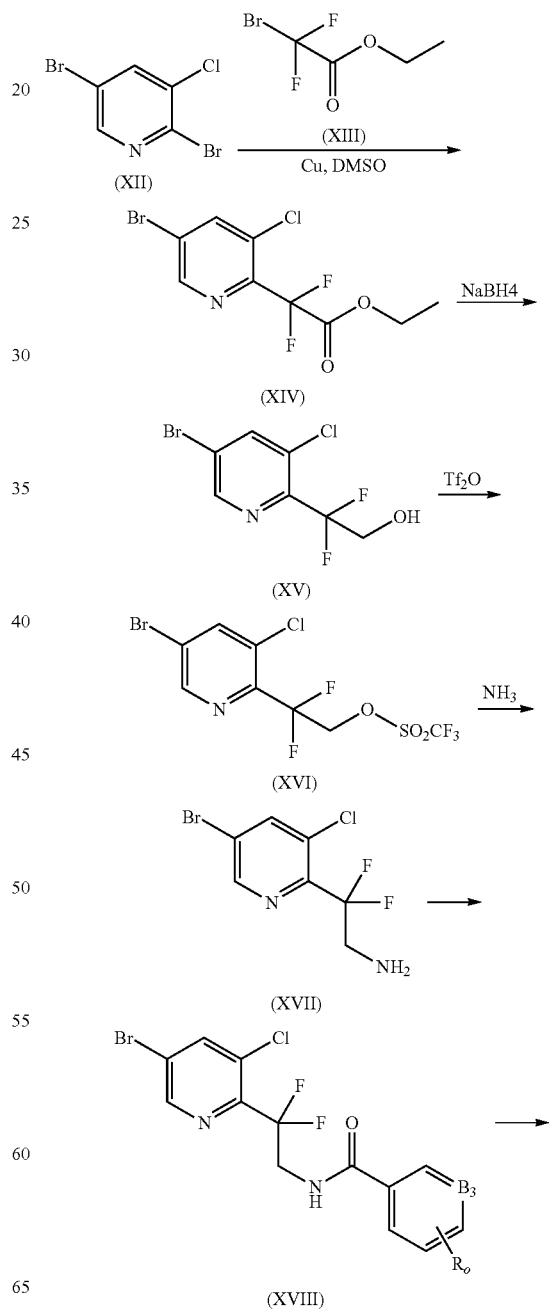

-continued

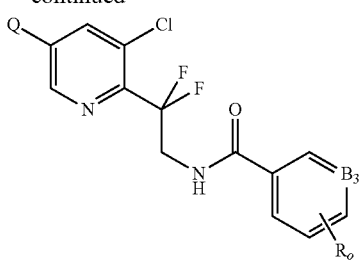

(I-b)

Of particular interest are intermediates of the procedures and methods described herein, especially compounds of formula (XIX) as described below. Such compounds of formula (XIX) comprise or are in analogy to compounds of formula (XVIII) in scheme 2. These intermediates are further individual embodiments of the invention.

Therefore, another embodiment of the invention is a compound of formula (XIX)

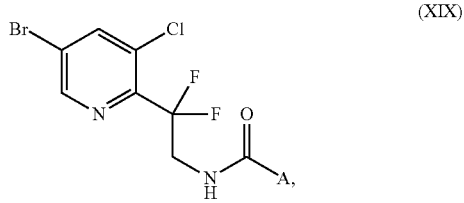

(XIX)

wherein
A is selected from:

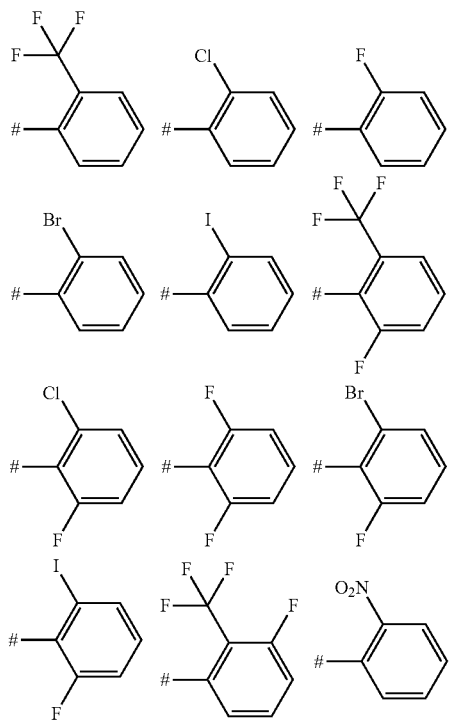

-continued

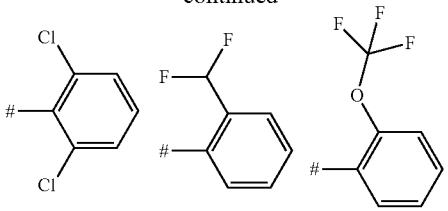

or
A is selected from:

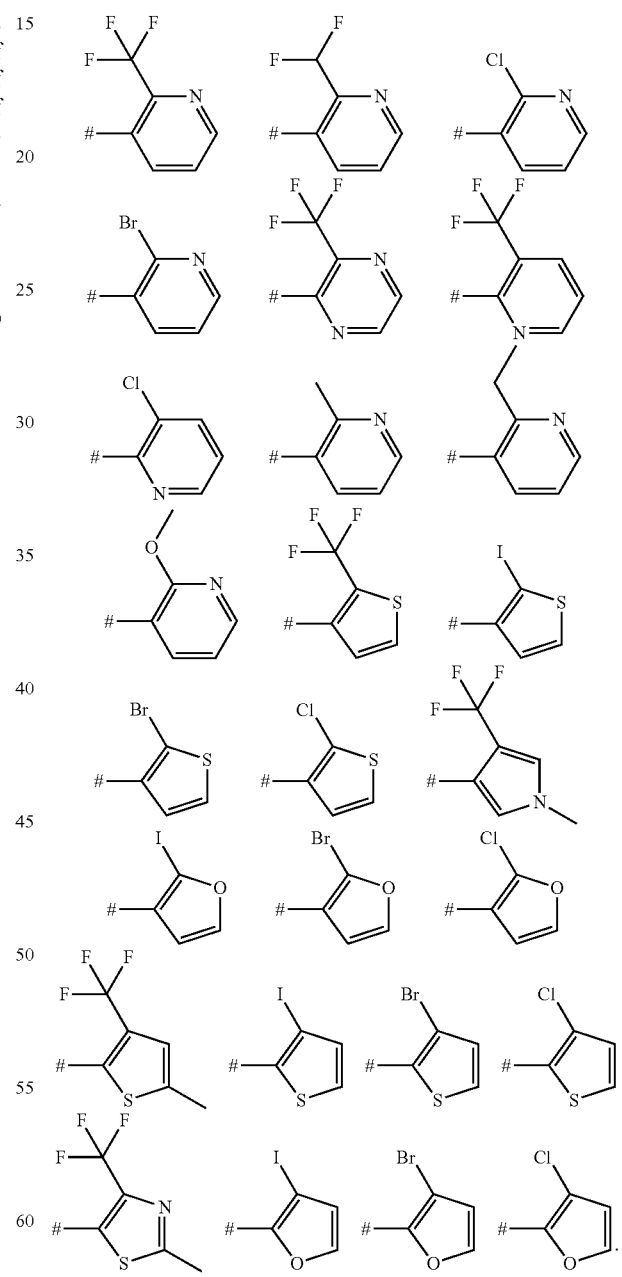

The compound according to the present invention can be prepared according to the processes described above. It will nevertheless be understood that, on the basis of his general knowledge and of available publications, the skilled worker will be able to adapt this method according to the specifics of each of the compounds, which it is desired to synthesize.

The compounds of the invention can be used as nematicides and/or as endoparasiticides.

A "nematicide" as used herein means that the compound is capable of controlling nematodes.

"Controlling nematodes" according to the invention shall mean to kill nematodes or to prevent their development or growth. The efficacy of the compositions or combinations according to the invention is assessed by comparing the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil treated with a composition or combination according to the invention and the untreated plant, plant part or soil (100%). Preferred is a reduction by 25-50% in comparison with the untreated plant, plant part or soil, very preferred a reduction by 51-79%, and particularly preferred the complete killing and the complete prevention of the development or growth by a reduction from 80% to 100% in comparison with the untreated plant, plant part or soil.

"Controlling nematodes" according to the invention shall also mean the control of the reproduction of the nematodes (e.g. development of cysts or eggs). The compounds and compositions according to the invention can be used for keeping the plants healthy and can be used curatively, preventively or systemically for controlling nematodes.

The expression "biologically effective amount" in the context of applying a chemical compound to control a nematode refers to an amount of the compound that is sufficient to control the nematode.

The skilled person knows methods for determining the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil. The treatment according to the invention reduces the damages caused by nematodes to the plant and leads to an increase in yield.

"Nematodes" as used herein encompass all species of the phylum Nematoda and in particular species that are parasitic or cause health problems to plant or to fungi (for example species of the orders *Aphelenchida*, *Meloidogyne*, *Tylenchida* and others) or to humans and animals (for example species of the orders *Trichinellida*, *Tylenchida*, *Rhabditina*, and *Spirurida*) as well as other parasitic helminths.

"Nematodes" as used herein, refer to plant nematodes meaning all nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonerna* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. Especially harmful root parasitic soil nematodes are such as cyst forming nematodes of the genera *Heterodera* or *Globodera*, and/or root knot nematodes of the genus *Meloidogyne*. Harmful species of these genera are for example *Meloidogyne incognita*, *Heterodera glycines* (soybean cyst nematode), *Globodera pallida* and *Globodera rostochiensis* (potato cyst nematode), which species are effectively controlled with the compounds described herein. However, the use of the compounds described herein is in no way restricted to these genera or species, but also extends in the same manner to other nematodes.

Plant nematodes include but are not limited to e.g. *Aglenchus agricola*, *Anguina tritici*, *Aphelenchoides arachidis*, *Aphelenchoides fragaria* and the stem and leaf endoparasites *Aphelenchoides* spp. in general, *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp. in general, *Cacopaurus pestis*, *Criconemella curvata*, *Criconemella onoensis*, *Criconemella ornata*, *Criconemella rusiwn*, *Criconemella xenoplax* (=*Mesocriconema xenoplax*) and *Criconemella* spp. in general, *Criconemoides ferniae*, *Criconemoides onoense*, *Criconemoides ornatum* and *Criconemoides* spp. in general, *Ditylenchus destructor*, *Ditylenchus dipsaci*, *Ditylenchus myceliophagus* and the stem and leaf endoparasites *Ditylenchus* spp. in general, *Dolichodorus heterocephalus*, *Globodera pallida* (=*Heterodera pallida*), *Globodera rostochiensis* (potato cyst nematode), *Globodera solanacearum*, *Globodera tabacum*, *Globodera virginia* and the sedentary, cyst forming parasites *Globodera* spp. in general, *Helicotylenchus digonicus*, *Helicotylenchus dihystera*, *Helicotylenchus erythrine*, *Helicotylenchus multicinctus*, *Helicotylenchus nannus*, *Helicolylenchus pseudorobuslus* and *Helicotylenchus* spp. in general, *Hemicriconemoides*, *Hemicycliophora arenaria*, *Hemicycliophora nudata*, *Hemicycliophora parvana*, *Heterodera avenae*, *Heterodera cruciferae*, *Heterodera glycines* (soybean cyst nematode), *Heterodera oryzae*, *Heterodera schachtii*, *Heterodera zeae* and the sedentary, cyst forming parasites *Heterodera* spp. in general, *Hirschmaniella gracilis*, *Hirschmaniella oryzae* *Hirschmaniella spinicaudata* and the stem and leaf endoparasites *Hirschmaniella* spp. in general, *Hoplolaimus aegyptii*, *Hoplolaimus californicus*, *Hoplolaimus columbus*, *Hoplolaimus galeatus*, *Hoplolaimus indicus*, *Hoplolaimus magnisvtylus*, *Hoplolaimus parabustus*, *Longidorus africanus*, *Longidorus breviannulatus*, *Longidorus elongatus*, *Longidorus laevicapitatus*, *Longidorus vineacola* and the ectoparasites *Longidorus* spp. in general, *Meloidogyne acronea*, *Meloidogyne africana*, *Meloidogre arenaria*, *Meloidogyne arenaria thamesi*, *Meloidogre artiella*, *Meloidogyne chitwoodi*, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuvensis*, *Meloidogyne minor*, *Meloidogyne naasi*, *Meloidogyne paranaensis*, *Meloidogyne thamesi* and the sedentary parasites *Meloidogyne* spp. in general, *Meloinema* spp., *Nacobbus aberrans*, *Neotylenchus vigissi*, *Paraphelenchus pseudoparietinums*, *Paratrichodorus allius*, *Paratrichodorus lobatus*, *Paratrichodorus minor*, *Paratrichodorus nanus*, *Paratrichodorus porosus*, *Paratrichodorus teres* and *Paratrichodorus* spp. in general, *Paratylenchus hamatus*, *Paratvylenchus minutus*, *Paratylenchus projectus* and *Paratylenchus* spp. in general, *Pratylenchus agilis*, *Pratylenchus alleni*, *Pratylenchus andinus*, *Pratylenchus brachyurus*, *Pratylenchus cerealis*, *Pratylenchus cofeae*, *Pratylenchus crenatus*, *Pratylenchus delattrei*, *Pratylenchus giibbicaudatus*, *Pratylenchus goodeyi*, *Pratylenchus hamatus*, *Pratylenchus hexincisus*, *Pratylenchus loosi*, *Pratylenchus negleclus*, *Pratlenchus penetrans*, *Pratylenchus pralensis*, *Pratylenchus scribneri*, *Pratylenchus teres*, *Pratylenchus thornei*, *Pratylenchus vulnus*, *Pratylen-* chus zeae and the migratory endoparasites *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and the migratory endoparasites *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhnchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema dimorphicaudatum, Xiphinema index* and the ectoparasites *Xiphinema* spp. in general.

Examples of nematodes to which a nematicide of the present invention is applicable include, but are not limited to, nematodes of the genus *Meloidogyne* such as the southern root-knot nematode (*Meloidogyne incognita*). Javanese root-knot nematode (*Meloidogyne javanica*), northern root-knot nematode (*Meloidogyne hapla*), and peanut root-knot nematode (*Meloidogyne arenaria*); nematodes of the genus *Ditylenchus* such as the potato rot nematode (*Ditylenchus destructor*) and bulb and stem nematode (*Ditylenchus dipsaci*); nematodes of the genus *Pratylenchus* such as the cob root-lesion nematode (*Pratylenchus penetrans*), chrysanthemum root-lesion nematode (*Pratylenchus fallax*), coffee root-lesion nematode (*Pratylenchus coffeae*), tea root-lesion nematode (*Pratylenchus loosi*), and walnut root-lesion nematode (*Pratylenchus vulnus*); nematodes of the genus *Globodera* such as the golden nematode (*Globodera rostochiensis*) and potato cyst nematode (*Globodera pallida*); nematodes of the genus *Heterodera* such as the soybean cyst nematode (*Heterodera glycines*) and sugar beet cyst nematode (*Heterodera schachtii*); nematodes of the genus *Aphelenchoides* such as the rice white-tip nematode (*Aphelenchoides besseyi*), chrysanthemum foliar nematode (*Aphelenchoides ritzemabosi*), and strawberry nematode (*Aphelenchoides fragariae*); nematodes of the genus *Aphelenchus* such as the mycophagous nematode (*Aphelenchus avenae*); nematodes of the genus *Radopholus* such as the burrowing nematode (*Radopholus similis*); nematodes of the genus *Tylenchulus* such as the citrus nematode (*Tylenchulus semipenetrans*); nematodes of the genus *Rotylenchulus* such as the reniform nematode (*Rotylenchulus reniformis*); nematodes that occur in trees, such as the pine wood nematode (*Bursaphelenchus xylophilus*), and the like.

Plants for which a nematicide of the present invention can be used are not particularly limited; for example, plants such as cereals (for example, rice, barley, wheat, rye, oat, corn, and the like), beans (soybeans, azuki beans, broad beans, peas, peanuts and the like), fruit trees/fruits (apples, citrus species, pears, grapes, peaches, Japanese apricots, cherries, walnuts, almonds, bananas, strawberries and the like), vegetables (cabbage, tomato, spinach, broccoli, lettuce, onion, Welsh onion, pepper and the like), root crops (carrot, potato, sweet potato, radish, lotus root, turnip and the like), industrial crops (cotton, hemp, paper mulberry, mitsumata, rape, beet, hop, sugarcane, sugar beet, olive, rubber, palms, coffee, tobacco, tea and the like), pepos (pumpkin, cucumber, watermelon, melon and the like), pasture plants (orchard grass, sorghum, thimosy, clover, alfalfa and the like), lawn grasses (mascarene grass, bent grass and the like), crops for flavorings etc. (lavender, rosemary, thyme, parsley, pepper, ginger and the like), and flower plants (*chrysanthemum*, rose, orchids and the like) can be mentioned.

The compound(s) and compositions comprising the compound(s) of the present invention is/are particularly useful in controlling nematodes in coffee belonging to at least one species selected from the group of the phytoparasitic nematodes consisting of *Pratylenchus brachyurus, Pratylenchus coffeae, Meloidogyne exigua, Meloidogyne incognita, Meloidogyne coffeicola, Helicotylenchus* spp. and also consisting of *Meloidogyne paranaensis, Rotylenchus* spp., *Xiphinema* spp., *Tylenchorhynchus* spp., *Scutellonema* spp.

Compound(s) and compositions comprising compound(s) of the present invention is/are particularly useful in controlling nematodes in potato belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylndricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

Compound(s) and compositions comprising the compound(s) of the present invention is/are particularly useful in controlling nematodes in tomato belonging to at least one species selected from the group of the phytoparasitic nematodes consisting of *Meloidogyne arenaria, Meloidogyne hapla, Meloidogyne javanica, Meloidogyne incognita, Pratylenchus penetrans* and also consisting of *Pratylenchus brachyurus, Pratylenchus coffeae, Pratylenchus scribneri, Pratylenchus vulnus, Paratrichodorus minor, Meloidogyne exigua, Nacobbus aberrans. Globodera solanacearum, Dolichodorus heterocephalus, Rotylenchulus reniformis.*

The compound(s) and compositions comprising the compound(s) of the present invention is/are particularly useful in controlling nematodes in cucurbits belonging to at least one species selected from the group of the phytoparasitic nematodes consisting of *Meloidogyne arenaria, Meloidogyne hapla, Meloidogyne javanica, Meloidogyne incognita, Rotylenchulus reniformis* and also consisting of *Pratylenchus thornei*.

The compound(s) and compositions comprising the compound(s) of the present invention is/are particularly useful in controlling nematodes in cotton belonging to at least one species selected from the group of the phytoparasitic nematodes consisting of *Belonolaimus longicaudatus. Meloidogyne incognita, Hoplolaimus columbus, Hoplolaimus galeatus, Rotylenchulus reniformis.*

The compound(s) and compositions comprising the compound(s) of the present invention is/are particularly useful in controlling nematodes in corn belonging to at least one species selected from the group of the phytoparasitic nematodes, especially consisting of *Belonolaimus longicaudatus*, *Paratrichodorus* minor and also consisting of *Pratylenchus brachyurus, Pratylenchus delattrei, Pratylenchus hexincisus, Pratylenchus penetrans, Pratylenchus zeae*, (*Belonolaimus gracilis*), *Belonolaimus nortoni, Longidorus breviannulatus, Meloidogyne arenaria, Meloidognte arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galealus, Hoplolaimus indicus, Helicolylenchus digonicus, Helicolylenchus dihystera, Helicoylenchus pseudorobusrtus, Xtphinema americanum, Dolichodorus heterocephalus, Criconemella ornata, Criconemella onoensis, Radopholus similis, Rolylenchulus borealis, Rotylenchulus parvus, Tylenchorhynchus agri, Tylenchorhynchus clarus, Tylenchorhynchus claytoni, Tylenchorhynchus maximus. Tylenchorhynchus nudus, Tylenchorhynchus vulgaris, Quinisulcius acutus. Paratylenchus minutus, Hemicycliophora parvana, Aglenchus agricola, Anguina tritici, Aphelenchoides arachidis, Scutellonema brachyurn, Subanguina radiciola*.

The compound(s) and compositions comprising the compound(s) of the present invention is/are particularly useful in controlling nematodes in soybean belonging to at least one species selected from the group of the phytoparasitic nematodes, especially consisting of *Pratylenchus brachyurus, Pratylenchus pratensis, Pratylenchus penetrans, Pratylenchus scribneri, Belonolaimus longicaudatus, Heterodera glines, Hoplolaimus columbus* and also consisting of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus*, (*Belonolaimus gracilis*), *Meloidogyne arenaria, Meloidogyne incognita, Meloidogyne javanica, Meloidogyne hapla, Hoplolaimus columbus, Hoplolaimus galeatus, Rotylenchulus reniformis*.

The compound(s) and compositions comprising the compound(s) of the present invention is/are particularly useful in controlling nematodes in tobacco belonging to at least one species selected from the group of the phytoparasitic nematodes, especially consisting of *Meloidogyne incognita, Meloidogyne javanica* and also consisting of *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla. Globodera tabacum, Globodera solanacearum, Globodera virginiae, Dilylenchus dipsaci, Rotylenchus* spp., *Helicotylenchus* spp., *Xiphinema americanum, Criconemella* spp., *Rotylenchulus rentformis, Tylenchorhynchus claytoni, Paratylenchus* spp., *Tetylenchus nicotianae*.

The compound(s) and compositions comprising the compound(s) of the present invention is/are particularly useful in controlling nematodes in citrus belonging to at least one species selected from the group of the phytoparasitic nematodes, especially consisting of *Pratylenchus coffeae* and also consisting of *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americamim, Xiphinema brevicolle, Xiphinema index, Criconemella* spp., *Hemicriconemoides, Radopholus similis* respectively *Radopholus citrophilus, Hemicycliophora arenaria, Hemicycliophora nudata, Tylenchulus semipenetrans*.

The compound(s) and compositions comprising the compound(s) of the present invention is/are particularly useful in controlling nematodes in banana belonging to at least one species selected from the group of the phytoparasitic nematodes, especially consisting of *Pratylenchus coffeae, Radopholus similis* and also consisting of *Pratylenchus giibbicaudatus, Pratylenchus loosi, Meloidogyne* spp., *Helicotylenchus multicinctus, Helicotylenchus dihystera, Rotylenchulus* spp.

The compound(s) and compositions comprising the compound(s) of the present invention is/are particularly useful in controlling nematodes in pine apple belonging to at least one species selected from the group of the phytoparasitic nematodes, especially consisting of *Pratylenchus zeae, Pratylenchus pratensis, Pratylenchus brachyurus, Pratylenchus goodeyi., Meloidogyne* spp., *Rotylenchulus reniformis* and also consisting of *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Heliconlenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorlhnchus ebriensis, Paralylenchus minutus, Scutellonema clathricaudatum, Scutellonema bradys, Psilenchus tumidus, Psilenchus magnidens, Pseudohalenchus minutus, Criconemoides ferniae, Criconemoides onoense, Criconemoides ornatum*.

The compound(s) and compositions comprising the compound(s) of the present invention is/are particularly useful in controlling nematodes in grapes belonging to at least one species selected from the group of the phytoparasitic nematodes, especially consisting of *Pratylenchus vulnus, Meloidogyne arenaria, Meloidogyne incognita, Meloidogyne javanica, Xiphinema americanum, Xiphinema index* and also consisting of *Pratylenchus pratensis, Pratylenchus scribneri, Pratylenchus neglectus, Pratylenchus brachyurus, Pratylenchus thornei, Tylenchulus semipenetrans*.

The compound(s) and compositions comprising the compound(s) of the present invention is/are particularly useful in controlling nematodes in tree crops—pome fruits, belonging to at least one species selected from the group of the phytoparasitic nematodes, especially consisting of *Pratylenchus penetrans* and also consisting of *Pratylenchus vulnus, Longidorus elongatus, Meloidogyne incognita, Meloidogyne hapla*.

The compound(s) and compositions comprising the compound(s) of the present invention is/are particularly useful in controlling nematodes in tree crops—stone fruits, belonging to at least one species selected from the group of the phytoparasitic nematodes, especially consisting of *Pratylenchus penetrans, Pratylenchus vulnus, Meloidogyne arenaria, Meloidogyne hapla, Meloidogyne javanica, Meloidogyne incognita, Criconemella xenoplax* and also consisting of *Pratylenchus brachyurus, Pratylenchus coffeae, Pratylenchus scribneri, Pratylenchus zeae, Belonolaimus longicarudatus, Helicotylenchus dihystera, Xiphinema americanum, Criconemella curvata, Tylenchorhynchus claytoni, Paratylenchus hamatus, Paratylenchus projectus, Scutellonema brachyurum, Hoplolaimus galeatus*.

The compound(s) and compositions comprising the compound(s) of the present invention is/are particularly useful in controlling nematodes in tree crops—nuts, belonging to at least one species selected from the group of the phytoparasitic nematodes, especially consisting of *Trichodorus* spp., *Criconemella rusium* and also consisting of *Pratylenchus vulnus*, *Paratrichodorus* spp., *Meloidogyne incognita*, *Helicotylenchus* spp., *Tylenchorhynchus* spp., *Cacopaurus pestis*.

In a like manner, "nematodes" as used herein, refer to nematodes which cause damage to humans or animals.

Specific nematode species harmful to humans or animals are:

Trichinellida for example: *Trichuris* spp., *Capillaria* spp., *Trichomosoides* spp., *Trichinella* spp.

From the order of the Tylenchida for example: *Micronema* spp., *Strongyloides* spp.

From the order of the Rhabditina for example: *Strongylus* spp., *Triodontophorus* spp., *Oesophagodonrus* spp., *Trichonema* spp., *Gyalocephahlus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomwn* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cvstocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hvostrongylus* spp., *Obeliscoides* spp., *Amidostomwn* spp., *Ollulanus* spp.

From the order of the *Spirurida* for example: *Oayuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Many known nematicides are equally active against other parasitic helminths and are therefore used to control human and animal parasitic worms, which do not necessarily belong to the group of nematoda. Therefore, it is envisaged by the present invention that the compounds described herein may also be used as anthelmintic drugs in a more general meaning. Pathogenic endoparasitic helminths include platyhelmintha (e.g. monogenea, cestodes and trematodes), acanthocephala, and pentastoma. The following helminths may be mentioned by way of example and by way of preference—but without any limitation:

Monogenea: e.g.: *Gyrodactylus* spp., *Dactylogyrus* spp., *Polystoma* spp.

Cestodes: From the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hvdatigera* spp., *Davainea* spp., *Raillietina* spp., *Hymenolepis* spp., *Echinolepis* spp., *Echinocotyle* spp., *Diorchis* spp., *Dipylidium* spp., *Joyuxiella* spp., *Diplopylidium* spp.

Trematodes: From the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Colylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nmanophyetus* spp., *Opisthorchis* spp., *Clonorchis* spp., *Metorchis* spp., *Heterophyes* spp., *Metagonimus* spp.

Acantocephala: From the order of the Oligacanthorhynchida z.B: *Macracanthorhynchus* spp., *Prosthenorchis* spp.: from the order of the Polymorphida for example: *Filicollis* spp.; from the order of the Moniliformida for example: *Moniliformis* spp., From the order of the Echinorhynchida for example *Acanthocephalus* spp., *Echinorhynchus* spp., *Leptorhynchoides* spp.

Pentastoma: From the order of the Porocephalida for example *Linguatula* spp.

In the veterinary field and in animal keeping, the administration of the active compounds according to the invention is carried out in the known manner directly or enterally, parenterally, dermally or nasally in the form of suitable preparations. Administration can be carried out prophylactically or therapeutically.

A further aspect of the invention are nematicidal compositions, comprising an effective amount of at least one compound as defined herein and at least one of the following: surfactant, solid or liquid diluent, characterized in that the surfactant or the diluent is normally used in nematicidal compositions. In an embodiment, said composition comprises at least two compounds as defined herein.

A related aspect of the invention is a method for preparing a nematicidal composition as described herein, comprising the step of mixing at least one compound as described herein with a surfactant or diluent normally used in nematicidal compositions. In an embodiment, said method comprises mixing at least two compounds as defined herein with a surfactant or diluent normally used in nematicidal compositions.

In particular, the present invention relates to nematicidal composition developed to be used in agriculture or horticulture. These nematicidal compositions may be prepared in a manner known per se.

In the animal health field, i.e. in the field of veterinary medicine, the active compounds according to the present invention are active against animal parasites, in particular ectoparasites or endoparasites. The term endoparasite includes in particular helminths and protozoae, such as coccidia. Ectoparasites are typically and preferably arthropods, in particular insects and acarids. The compounds of formula (I) are preferably active against helminths.

In the field of veterinary medicine the compounds according to the invention are suitable, with favourable warm blood toxicity, for controlling parasites which occur in animal breeding and animal husbandry in livestock, breeding, zoo, laboratory, experimental and domestic animals. They are active against all or specific stages of development of the parasites.

Agricultural livestock include, for example mammals, such as, sheep, goats, horses, donkeys, camels, buffaloes, rabbits, reindeers, fallow deers, and in particular cattle and pigs; or poultry such as turkeys, ducks, geese, and in particular chickens; or fish or crustaceans e.g. in aquaculture; or as the case may be insects such as bees.

Domestic animals include, for example mammals, such as hamsters, guinea pigs, rats, mice, chinchillas, ferrets or in particular dogs, cats; cage birds; reptiles; amphibians or aquarium fish.

According to a preferred embodiment, the compounds according to the invention are administered to mammals.

According to another preferred embodiment, the compounds according to the invention are administered to birds, namely cage birds or in particular poultry.

By using the active compounds according to the invention to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Exemplary arthropods include, without anylimitation:
from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.; from the order of the Heteropterida, for example *Cimex* spp., *Triatoma* spp., *Rhodnius* spp., *Panstrongylus* spp.; as well as nuisance and hygiene pests from the order of the Blattarida.

Further, among the arthropods, the following acari may be mentioned by way of example, without any limitation:
from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi host ticks); from the order of mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Exemplary parasitic protozoa include—, without anylimitation:

Mastigophora (*Flagellata*), such as, for example. Trypanosomatidae, for example, *Trypanosoma b, brucei, T.b. gambiense, T.b. rhodesiense, T. congolense, T. cruzi, T. evansi, T. equinum, T. lewisi, T. percae, T. simiae, T. vivax, Leishmania brasiliensis. L. donovani, L. tropica*, such as, for example, Trichomonadidae, for example, *Giardia lamblia, G. canis.*

Sarcomastigophora (Rhizopoda), such as Entamoebidae, for example, *Entamoeba histolytica, Hartmanellidae*, for example, *Acanthamoeba* sp., *Harmanella* sp.

Apicomplexa (Sporozoa), such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae. E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis. E. tenella, E. truncata, E. truttae, E. zuernii, Globidium spec., Isospora belli, I. canis, I. felis, I. ohioensis, I. rivolta, I. spec., I. suis, Cystisospora spec., Cryptosporidium spec.*, in particular *C. parvum*; such as Toxoplasmadidae, for example, *Toxoplasma gondii, Hammondia heydornii, Neospora caninum, Besnoitia besnoitii*; such as Sarcocystidae, for example, *Sarcocystis bovicanis, S. bovihominis, S. ovicanis, S. ovifelis, S. neurona, S. spec., S. suihominis*, such as Leucozoidae, for example, *Leucozytozoon simondi*, such as Plasmodiidae, for example, *Plasmodium berghei, P. falciparum, P. malariae. P. ovale, P. vivax, P. spec.*, such as Piroplasmea, for example, *Babesia argentina, B. bovis, B. canis, B. spec., Theileria parva, Theileria* spec., such as Adeleina, for example, *Hepatozoon canis, H. spec.*

Exemplary pathogenic endoparasites, which are helminths, include platyhelmintha (e.g. monogenea, cestodes and trematodes), nematodes, acanthocephala, and pentastoma. Additional exemplary helminths include—, without anylimitation:

Monogenea: e.g.: *Gyrodactylus* spp., *Dactylogyrus* spp., *Polystoma* spp.,

Cestodes: From the order of the Pseudophyllidea for example: *Diphyllobothrium* spp., *Spirometra* spp., *Schistocephalus* spp., *Ligula* spp., *Bothridium* spp., *Diplogonoporus* spp., From the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp., Trematodes: From the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp., Nematodes: Trichinellida for example: *Trichuris* spp., *Capillaria* spp., *Trichomosoides* spp., *Trichinella* spp., From the order of the *Tylenchida* for example: *Micronema* spp., *Strongyloides* spp., From the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the *Spirurida* for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acantocephala: From the order of the Oligacanthorhynchida z.B: *Macracanthorhynchus* spp., *Prosthenorchis* spp.; from the order of the Polymorphida for example: *Filicollis* spp.; from the order of the Moniliformida for example: *Moniliformis* spp., From the order of the Echinorhynchida for example *Acanthocephalus* spp., *Echinorhynchus* spp., *Leptorhynchoides* spp.

Pentastoma: From the order of the Porocephalida for example *Linguatula* spp.

In the veterinary field and in animal keeping, the administration of the active compounds according to the invention is carried out by methods generally known in the art, such as enterally, parenterally, dermally or nasally in the form of suitable preparations. Administration can be carried out prophylactically or therapeutically.

Thus, one embodiment of the present invention refers to compounds according to the invention for use as a medicament.

Another aspect refers to compounds according to the invention for use as an antiendoparasitical agent, in particular a helminthicidal agent or antiprotozoaic agent. For example, compounds according to the invention for use as an antiendoparasitical agent, in particular an helminthicidal agent or antiprotozoaic agent, e.g., in animal husbandry, in animal breeding, in animal housing, in the hygiene sector.

Yet another aspect refers to compounds according to the invention for use as an antiectoparasitical agent, in particular an arthropodicidal agent such as an insecticidal agent or acaricidal agent. For example, compounds according to the invention for use as an antiectoparasitical agent, in particular an arthropodicidal agent such as an insecticidal agent or acaricidal agent, e.g., in animal husbandry, in animal breeding, in animal housing, in the hygiene sector.

The present invention further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides. FAO Plant Production and Protection Papers-173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraflins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants which can be improved by applying the compounds of formula (I) include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or else plants such as tobacco, nuts, coffee, aubergine, sugar cane, tea, pepper, grapevines, hops, bananas, latex plants and ornamentals, for example flowers, shrubs, deciduous trees and coniferous trees. This enumeration is no limitation.

The following plants are considered to be particularly suitable target crops: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp. *Quercus* sp., *Fagus* sp., *Salix* sp., *Populus* sp.

Preferred trees which can be improved in accordance with the method according to the invention are: from the tree species *Aesculus*: *A. hippocastanum*, *A. pariflora*, *A. carnea*; from the tree species *Platanus*: *P. aceriflora*, *P. occidentalis*, *P. racemosa*; from the tree species *Picea*: *P. abies*; from the tree species *Pinus*: *P. radiata*, *P. ponderosa*, *P. contorta*, *P. sylvestre*, *P. elliottii*, *P. montecola*, *P. albicaulis*, *P. resinosa*, *P. palustris*. *P. taeda*. *P. flexilis*, *P. jeffregi*, *P. baksiana*, *P. strobus*; from the tree species *Eucalyptus*: *E. grandis*, *E. globulus*, *E. camadentis*, *E. nitens*, *E. obliqua*, *E. regnans*, *E. pilularus*.

Especially preferred trees which can be improved in accordance with the method according to the invention are: from the tree species *Pinus*: *P. radiata*, *P. ponderosa*, *P. contorta*, *P. sylvestre*, *P. strobus*; from the tree species *Eucalyptus*: *E. grandis*, *E. globulus*, *E. camadentis*.

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.);

fescues (*Festuca* spp.), such as red fescue (*Festuca rubra* L, spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turf grasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpetgrass (*Axonopus affinis* Chase), Bahia grass (*Paspalum notatum* Flugge), Kikuyu grass (*Pennisetum clandestinum* Hochst, ex Chiov.), buffalo grass (*Buchloe dactyloids* (Nutt.) Engelm.), blue grama (*Bouteloua gracilis* (H.B.K.) Lag, ex Griffiths), seashore *paspalum* (*Paspalum vaginatum* Swartz) and sideoats grama (*Boutelotua curtipendula* (Michx. Torr.). Cool-season turf grasses are generally preferred for the use according to the invention. Especially preferred are bluegrass, benchgrass and redtop, fescues and ryegrasses. Bentgrass is especially preferred.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

The control of animal pests by treating the seed of plants has been known for a long time and is a subject of continual improvements. Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by animal pests, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The present invention therefore also relates in particular to a method for protecting seed and germinating plants from attack by pests, by treating the seed with a compound of formula (I).

The invention likewise relates to the use of the compound of formula (I) for treating seed for the purpose of protecting the seed and the resultant plant against animal pests.

The invention relates, furthermore, to seed which for protection against animal pests has been treated with a compound of formula (I).

Furthermore, the invention relates to seed which, following treatment with a compound of formula (I) of the invention, is subjected to a film-coating process in order to prevent dust abrasion of the seed.

One of the advantages of the present invention is that, owing to the particular systemic properties of the compositions of the invention, the treatment of the seed with these compositions provides protection from animal pests not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with a compound of formula (I) of the invention, germination and emergence of the treated seed may be promoted.

It is likewise considered to be advantageous that compound of formula (I) may also be used, in particular, on transgenic seed.

It is also stated that a compound of formula (I) may be used in combination with agents of the signalling technology, as a result of which, for example, colonization with symbionts is improved, such as *rhizobia*, mycorrhiza and/or endophytic bacteria, for example, is enhanced, and/or nitrogen fixation is optimized.

The compositions of the invention are suitable for protecting seed of any variety of plant which is used in agriculture, in greenhouses, in forestry or in horticulture. More particularly, the seed in question is that of cereals (e.g. wheat, barley, rye, oats and millet), maize, cotton, soybeans, rice, potatoes, sunflower, coffee, tobacco, canola, oilseed rape, beets (e.g. sugar beet and fodder beet), peanuts, vegetables (e.g. tomato, cucumber, bean, brassicas, onions and lettuce), fruit plants, lawns and ornamentals. Particularly important is the treatment of the seed of cereals (such as wheat, barley, rye and oats) maize, soybeans, cotton, canola, oilseed rape and rice.

As already mentioned above, the treatment of transgenic seed with a compound of formula (I) is particularly important. The seed in question here is that of plants which generally contain at least one heterologous gene that controls the expression of a polypeptide having, in particular, insecticidal and/or nematicidal properties. These heterologous genes in transgenic seed may come from microorganisms such as *Bacillus, Rhizobium, Pseudomonas, Serratia, Trichoderma, Clavibacter, Glomus* or *Gliocladium*. The present invention is particularly suitable for the treatment of transgenic seed which contains at least one heterologous gene from *Bacillus* sp. With particular preference, the heterologous gene in question comes from *Bacillus thuringiensis*.

For the purposes of the present invention, the compound of formula (I) of the invention is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied directly, in other words without comprising further components and without having been diluted. As a general rule, it is preferable to apply the compositions in the form of a suitable formulation to the seed. Suitable formulations and methods for seed treatment are known to the skilled person and are described in, for example, the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The compound of formula (I) which can be used in accordance with the invention may be converted into the customary seed-dressing formulations, such as solutions, emulsions, suspensions, powders, foams, slurries or other coating compositions for seed, and also ULV formulations.

These formulations are prepared in a known manner, by mixing the compound of formula (I) with customary adjuvants, such as, for example, customary extenders and also solvents or diluents, colorants, wetters, dispersants, emulsifiers, antifoams, preservatives, secondary thickeners, stickers, gibberellins, and also water.

Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under the designations Rhodamin B, C.I. Pigment Red 112 and C.I. Solvent Red 1.

Wetters which may be present in the seed-dressing formulations which can be used in accordance with the invention include all of the substances which promote wetting and which are customary in the formulation of active agrochemical ingredients. Use may be made preferably of alkylnaphthalene-sulphonates, such as diisopropyl- or diisobutyl-naphthalenesulphonates.

Dispersants and/or emulsifiers which may be present in the seed-dressing formulations which can be used in accordance with the invention include all of the nonionic, anionic and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers and also tristryrylphenol polyglycol ethers, and the phosphated or sulphated derivatives of these. Suitable anionic dispersants are, in particular, lignosulphonates, salts of polyacrylic acid, and arylsulphonate-formaldehyde condensates.

Antifoams which may be present in the seed-dressing formulations which can be used in accordance with the invention include all of the foam inhibitors that are customary in the formulation of active agrochemical ingredients. Use may be made preferably of silicone antifoams and magynesium stearate.

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and highly disperse silica.

Stickers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol and tylose.

Gibberellins which may be present in the seed-dressing formulations which can be used in accordance with the invention include preferably the gibberellins A1, A3 (=gibberellic acid), A4 and A7, with gibberellic acid being used with particular preference. The gibberellins are known (cf. R. Wegler, "Chemie der Pflanzenschutz-und Schädlingsbekämpfungsmittel", Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or the preparations obtainable from them by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In that case, additional synergistic effects may occur in interaction with the substances formed through expression.

For the treatment of seed with the seed-dressing formulations which can be used in accordance with the invention, or with the preparations produced from them by addition of water, suitable mixing equipment includes all such equipment which can typically be employed for seed dressing. More particularly, the procedure when carrying out seed dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It is guided by the particular amount of the compound of formula (I) in the formulations, and by the seed. The application rates with regard to the compound of formula (I) are situated generally at between 0.001 and 50 g per kilogram of seed, preferably between 0.01 and 15 g per kilogram of seed.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in over additive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugar beet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut®® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape). IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The treatment of the plants and plant parts with the compounds of formula (I) is carried out directly or by acting on the environment, habitat or storage space using customary treatment methods, for example by dipping, spraying, atomizing, misting, evaporating, dusting, fogging, scattering, foaming, painting on, spreading, injecting, drenching, trickle irrigation and, in the case of propagation material, in particular in the case of seed, furthermore by the dry seed treatment method, the wet seed treatment method, the slurry treatment method, by encrusting, by coating with one or more coats and the like. It is furthermore possible to apply the active substances by the ultra-low volume method or to inject the active substance preparation or the active substance itself into the soil.

A preferred direct treatment of the plants is the leaf application treatment, i.e. compounds of formula (I) or compositions containing them are applied to the foliage, it being possible for the treatment frequency and the application rate to be matched to the infection pressure.

In the case of systemically active compounds, compounds of formula (I) or compositions according to the invention reach the plants via the root system. In this case, the treatment of the plants is effected by allowing the compounds of formula (I) or compositions according to the invention to act on the environment of the plant. This can be done for example bydrenching, incorporating in the soil or into the nutrient solution, i.e. the location of the plant (for example the soil or hydroponic systems) is impregnated with a liquid form of compounds of formula (I) or compositions according to the invention, or by soil application, i.e. the compounds of formula (I) or compositions according to the invention are incorporated into the location of the plants in solid form (for example in the form of granules). In the case of paddy rice cultures, this may also be done by metering the compounds of formula (I) or compositions according to the invention into a flooded paddy field in a solid use form (for example in the form of granules).

The inventive active ingredient may be present in its commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals. The mixtures thus obtained have a broadened spectrum of activity.

Mixtures with fungicides are particularly advantageous. Examples of suitable fungicide mixing partners can be selected from the list consisting of 1) Inhibitors of the ergosterol biosynthesis, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]1H-imidazole-1-carbothioate, (1.65) Pyrisoxazole.

2) Inhibitors of the respiratory chain at complex I or II, for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) Isofetamid.

3) Inhibitors of the respiratory chain at complex III, for example (3.1) ametoctradin, (3.2) amisulbrom, (3.3) azoxystrobin, (3.4) cyazofamid, (3.5) coumethoxystrobin, (3.6) coumoxystrobin, (3.7) dimoxystrobin, (3.8) enoxastrobin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy phenyl)-2-(methoxyimino)-N-methylacetamide, (3.24) (2E)-2-(methoxy imino)-N-methyl-2-(2-{[({(1E)-1-[3-(trifluoromethyl)phenyl]ethylidene}amino)oxy] methyl}phenyl)acetamide, (3.25) (2E)-2-(methoxyimino)-N-methyl-2-{2-[(E)-({(1-[3-(trifluoromethyl)phenyl] ethoxy}imino)methyl]phenyl}acetamide, (3.26) (2E)-2-{2-[({[(1E)-1-(3-{[(E)-1-fluoro-2-phenylvinyl]oxy}phenyl) ethylidene]amino}oxy)methyl]phenyl}-2-(methoxyimino)-N-methylacetamide, (3.27) Fenaminostrobin, (3.28) 5-methoxy-2-methyl-4-(2-([{(1E)-1-[3-(trifluoromethyl) phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulfanyl) methyl]phenyl}-3-methoxyacrylate, (3.30) N-(3-ethyl-3,5,5-trimethylcyclohexyl)-3-formamido-2-hydroxybenzamide, (3.31) 2-(2-[(2,5-dimethylphenoxy)methyl]phenyl)-2-methoxy-N-methylacetamide, (3.32) 2-{2-[(2,5-dimethylphenoxy)methyl]phenyl}-2-methoxy-N-methylacetamide.

4) Inhibitors of the mitosis and cell division, for example (4.1) benomyl, (4.2) carbendazim, (4.3) chlorfenazole, (4.4) diethofencarb, (4.5) ethaboxam, (4.6) fluopicolide, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazaolo[15-a]pyrimidine, (4.14) 3-chloro-5-(6-chloropyridin-3-yl)-6-methyl-4-(2,4,6-trifluorophenyl) pyridazine.

5) Compounds capable to have a multisite action, for example (5.1) bordeaux mixture, (5.2) captafol, (5.3) captan, (5.4) chlorothalonil, (5.5) copper hydroxide, (5.6) copper naphthenate, (5.7) copper oxide, (5.8) copper oxychloride, (5.9) copper(2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable to induce a host defence, for example (6.1) acibenzolar-S-methyl, (6.2) isotianil, (6.3) probenazole, (6.4) tiadinil, (6.5) laminarin.

7) Inhibitors of the amino acid and/or protein biosynthesis, for example (7.1) andoprim, (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline, (7.9) oxytetracycline, (7.10) streptomycin.

8) Inhibitors of the ATP production, for example (8.1) fentin acetate, (8.2) fentin chloride, (8.3) fentin hydroxide, (8.4) silthiofam.

9) Inhibitors of the cell wall synthesis, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate, (9.10) polyoxin B.

10) Inhibitors of the lipid and membrane synthesis, for example (10.1) biphenyl, (10.2) chloroneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of the melanin biosynthesis, for example (11.1) carpropamid, (11.2) diclocymet, (11.3) fenoxanil, (11.4) phthalide, (11.5) pyroquilon, (11.6) tricyclazole, (11.7) 2,2,2-trifluoroethyl {3-methyl-1-[(4-methylbenzoyl)amino]butan-2-yl}carbamate.

12) Inhibitors of the nucleic acid synthesis, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazol, (12.9) metalaxyl, (12.10) metalaxyl-M (mefenoxam), (12.11) ofurace, (12.12) oxadixyl, (12.13) oxolinic acid, (12.14) octhilinone.

13) Inhibitors of the signal transduction, for example (13.1) chlozolinate, (13.2) fenpiclonil, (13.3) fludioxonil, (13.4) iprodione, (13.5) procymidone, (13.6) quinoxyfen, (13.7) vinclozolin, (13.8) proquinazid.

14) Compounds capable to act as an uncoupler, for example (14.1) binapacryl, (14.2) dinocap, (14.3) ferimzone, (14.4) fluazinam, (14.5) meptyldinocap.

15) Further compounds, for example (15.1) benthiazole, (15.2) bethoxazin, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat metilsulfate, (15.17) diphenylamine, (15.18) ecomate, (15.19) fenpyrazamine, (15.20) flumetover, (15.21) fluoroimide, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.37) oxamocarb, (15.38) oxyfenthiin, (15.39) pentachlorophenol and salts, (15.40) phenothrin, (15.41) phosphorous acid and its salts, (15.42) propamocarb-fosetylate, (15.43) propanosine-sodium, (15.44) pyrimorph, (15.45) (2E)-3-(4-tert-butlphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrine, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-y]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulfonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl) ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl) thiophene-2-sulfonohydrazide, (15.74) 5-fluoro-2-[(4-fluorobenzyl)oxy]pyrimidin-4-amine, (15.75) 5-fluoro-2-[(4-methylbenzyl)oxy]pyrimidin-4-amine, (15.76) 5-methyl-6-octyl[1,2,4]triazolo[1,5-a]pyrimidin-7-amine, (15.77) ethyl (2Z)-3-amino-2-cyano-3-phenylacrylate, (15.78) N'-(4-{[3-(4-chlorobenzyl)-1,2,4-thiadiazol-5-yl] oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-arboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene] amino}oxy)methyl]pyridin-2-yl}carbamate, (15.91) phenazine-1-carboxylic acid, (15.92) quinolin-8-ol, (15.93) quinolin-8-ol sulfate (2:1), (15.94) tert-butyl {6-[({[(1-methyl-1H-tetrazol-5-yl)(phenyl)methylene]amino}oxy) methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl) biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl) nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl] nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3- dimethyl-1H-pyrazole-4-carboxamide (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulfonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulfanyl)-1-{[rel(2R,3S)-3-(2-chlorophenyl)-2-(2,4-difluorophenyl)oxiran-2-yl]methyl}-1H-1,2,4-triazole, (15.136) 5-(allylsulfanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) Abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-isopropylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-arboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-arboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazole-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-H- pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazol-5-amine.

Mixtures with insecticides are also particularly advantageous. Examples of suitable insecticide mixing partners can be selected from the list consisting of (1) Acetylcholinesterase (AChe) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC and Xylylcarb or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl)salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon and Vamidothion.

(2) GABA-gated chloride channel antagonists, for example cyclodiene organochlorines, e.g. Chlordane and Endosulfan or phenylpyrazoles (fiproles), e.g. Ethiprole and Fipronil.

(3) Sodium channel modulators/voltage-dependent sodium channel blockers, for example pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin and Transfluthrin or DDT or Methoxychlor.

(4) Nicotinic acetylcholine receptor (nAChR) agonists, for example neonicotinoids, e.g. Acetamiprid, Clothianidin, Dinotefuran, Imidacloprid, Nitenpyram, Thiacloprid and Thiamethoxam or Nicotine or Sulfoxaflor.

(5) Nicotinic acetylcholine receptor (nAChR) allosteric activators, for example spinosyns, e.g. Spinetoram and Spinosad.

(6) Chloride channel activators, for example avermectins/milbemycins, e.g. Abamectin, Emamectin benzoate, Lepimectin and Milbemectin.

(7) Juvenile hormone mimics, for example juvenile hormon analogues, e.g. Hydroprene, Kinoprene and Methoprene or Fenoxycarb or Pyriproxyfen.

(8) Miscellaneous non-specific (multi-site) inhibitors, for example alkyl halides, e.g. Methyl bromide and other alkyl halides; or Chloropicrin or Sulfuryl fluoride or Borax or Tartar emetic.

(9) Selective homopteran feeding blockers, e.g. Pymetrozine or Flonicamid.

(10) Mite growth inhibitors, e.g. Clofentezine, Hexythiazox and Diflovidazin or Etoxazole.

(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example Diafenthiuron or organotin miticides, e.g. Azocyclotin, Cyhexatin and Fenbutatin oxide or Propargite or Tetradifon.

(13) Uncouplers of oxidative phoshorylation via disruption of the proton gradient, for example Chlorfenapyr, DNOC and Sulfluramid.

(14) Nicotinic acetylcholine receptor (nAChR) channel blockers, for example Bensultap, Cartap hydrochloride, Thiocyclam and Thiosultap-sodium.

(15) Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide and Tebufenozide.

(19) Octopamine receptor agonists, for example Amitraz.

(20) Mitochondrial complex III electron transport inhibitors, for example Hydramethylnon or Acequinocyl or Fluacrypyrim.

(21) Mitochondrial complex I electron transport inhibitors, for example METI acaricides, e.g. Fenazaquin, Fenpyroximate, Pyrimidifen, Pyridaben, Tebufenpyrad and Tolfenpyrad or Rotenone (Derris).

(22) Voltage-dependent sodium channel blockers, e.g. Indoxacarb or Metaflumizone.

(23) Inhibitors of acetyl CoA carboxylase, for example tetronic and tetramic acid derivatives, e.g. Spirodiclofen, Spiromesifen and Spirotetramat.

(24) Mitochondrial complex IV electron transport inhibitors, for example phosphines, e.g. Aluminium phosphide, Calcium phosphide. Phosphine and Zinc phosphide or Cyanide.

(25) Mitochondrial complex II electron transport inhibitors, for example Cyenopyrafen and Cyflumetofen.

(28) Ryanodine receptor modulators, for example diamides, e.g. Chlorantraniliprole, Cyantraniliprole and Flubendiamide.

Further active ingredients with unknown or uncertain mode of action, for example Afidopyropen, Azadirachtin, Benclothiaz, Benzoximate, Bifenazate, Bromopropylate, Chinomethionat, Cryolite, Dicofol, Diflovidazin, Fluensulfone, Flometoquin, Flufenerim, Flufenoxystrobin, Flufiprole, Fluopyram, Flupyradifurone, Fufenozide, Heptafluthrin, Imidaclothiz, Iprodione, Meperfluthrin. Paichongding, Pyflubumide, Pyrifluquinazon, Pyriminostrobin, Tetramethylfluthrin and Iodomethane; furthermore products based on *Bacillus firmus* (including but not limited to strain CNCM I-1582, such as, for example, VOTiVO™, BioNem) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluorethyl)sulfinyl]phenyl}-3-(trifluoromethyl)-1H-1,2,4-triazol-5-amine (known from WO20061043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO20061003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO02003/076415), PF1364 (CAS-Reg.No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-clhoro-5-methoxyphenyl)sulfonyl]-6-(trifluoromethyl)imidazo[1,2-a]pyridine-2-carboxamide (known from WO2010/129500), 8-chloro-N-[(2-chloro-5-methoxyphenyl)sulfonyl]-6-(trifluoromethyl)imidazo[1,2-a]pyridine-2-carboxamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxy imidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Mixtures with nematicides are also particularly advantageous. Examples of suitable nematicide mixing partners can be selected from the list consisting of Dichloropropene, Metam sodium, Metam potassium, Chloropicrin, Oxamyl, Carbofuran, Fosthiazate, Aldicarb, Fenamiphos, Cadusafos, Abamectin, Cyanamide, Dazomet, Methylbromide, Terbufos, Ethoprophos, Ethylen dibromide, Phorate, Methylisothiocyanate, Thiodicarb, Sodium tetrathiocarbonate, Iprodione, Fluensulfone, Imicyafos, Dimethyl disulfide, Spirotetramate, Fluopyram, 1-{2-fluoro-4-methyl-5-[(2,2,2-trifluoroethyl)sulfinyl]phenyl}-3-(trifluoromethyl)-1H-1,2,4-triazol-5-amine, 8-chloro-N-[(2-chloro-5-methoxyphenyl)sulfonyl]-6-(trifluoromethyl) imidazo[1,2-a]pyridine-2-carboxamide, 8-chloro-N-[(4-cyano-2,5-dimethylphenyl)sulfonyl]-6-(trifluoromethyl) imidazo[1,2-a]pyridine-2-carboxamide, 2-(4-chlorophenyl)-5-(2-thienyl)-1,3,4-oxadiazole, 5-phenyl-2-(2-thienyl)-1,3-oxazole, 5-(4-chlorophenyl)-2-(2-thienyl)-1,3-oxazole, 5-(4-bromophenyl)-2-(2-thienyl)-1,3-oxazole or 2-(4-chlorophenyl)-5-(2-thienyl)-2H-tetrazole.

For the animal health field, mixtures with anthelmintics are also particularly advantageous.

Exemplary mixing partners include, without any limitation:

Anthelmintic actives, including trematicidal and cestocidal actives:

From the class of macrocyclic lactones, for example:

abamectin, doramectin, emamectin, eprinomectin, ivermectin, milbemycin, moxidectin, nemadectin, selamecctin;

from the class of benzimidazoles and probenzimidazoles, for example:

albendazole, albendazole sulfoxide, cambendazole, cyclobendazole, febantel, fenbendazole, flubendazole, mebendazole, netobimin, oxfendazole, oxibendazole, parbendazole, thiabendazole, thiophanate, triclabendazole:

from the class of cyclooctadepsipeptides, for example:

emodepside, PF1022;

from the class of aminoacetonitrile derivatives, for example:

monepantel:

from the class of tetrahydropyrimidines, for example:

morantel, pyrantel, oxantel;

from the class of imidazothiazoles, for example:

butamisole, levamisole, tetramisole:

from the class of salicylanilides, for example:

bromoxanide, brotianide, clioxanide, closantel, niclosamide, oxyclozanide, rafoxanide, tribromsalan;

from the class of paraherquamides, for example:

derquantel, paraherquamide;

from the class of aminophenylamidines, for example:

amidantel, deacylated amidantel (dAMD), tribendimidine;

from the class of organophosphates, for example:

coumaphos, crufomate, dichlorvos, haloxon, naphthalofos, trichlorfon;

from the class of substituted phenols, for example:

bithionole, disophenol, hexachlorophen, niclofolan, meniclopholan, nitroxynil;

from the class of piperazinones, for example:

praziquantel, epsiprantel;

from diverse other classes, for example:

amoscanate, bephenium, bunamidine, clonazepam, clorsulon, diamfenetide, dichlorophen, diethylcarbamazine, emetine, hetolin, hycanthone, lucanthone, miracil, mirasan, niclosamide, niridazole, nitroxynile, nitroscanate, oltipraz, omphalotin, oxamniquine, paromomycin, piperazine, resorantel.

All named mixing partners can, if their functional groups enable this, optionally form salts with suitable bases or acids.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

The active substances, active substance combinations or compositions according to the invention can also be combined with microbials.

The microbials according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development. The abovementioned microbials include:

Microbials from the domain Bacteria, microbials from the domain Fungi, insecticidal microbials from the domain Protozoa, insecticidal microbials from the domain Viruses, and microbials from the domain of entomopathogenic nematodes.

The various aspects of the invention will now be illustrated with reference to the following production and use examples in a non limiting manner.

PREPARATION EXAMPLES $^1$H-NMR Data $^1$H-NMR-data were determined with a Bruker Avance 400 equipped with a flow cell (60 μl volume) or with a Bruker AVIII 400 equipped with 1.7 mm cryo-CPTCT probe head or with a Bruker AVII 600 (600.13 MHz) equipped with a cyroTCI probe head or with a Bruker AVIII 600 (601.6 MHz) equipped with a cryo CPMNP probe head with tetramethylsilane as reference (0.0) and the solvents CD$_3$CN, CDCl$_3$, D$_6$-DMSO.

NMR-data of selected examples are listed in classic format (chemical shift δ, multiplicity, number of hydrogen atoms) or as NMR-peak-lists.

The NMR spectra of the steps of preparation example 1 and the NMR spectra of examples 1-5 have been measured on a Varian 400 MHz Mercury Plus.

Preparation Example 1

Step 1

Synthesis of ethyl (5-bromo-3-chloropyridin-2-yl)-(cyano)acetate

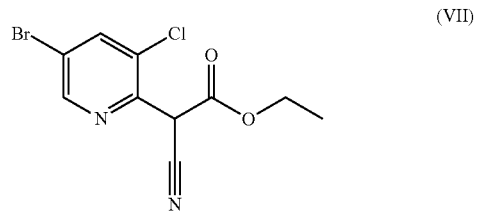 [SMILES: CCOC(=O)C(C#N)c1ncc(Br)cc1Cl]

(VII)

To a suspension of NaH (4.0 g, 1.5 eq.) in DMF (45 ml) at 0° C., ethyl cyanoacetate (10.6 ml, 1.5 eq.) was added and stirred at room temperature for 30 minutes. Then 5-bromo-2,3-dichloropyridine (15.0 g, 1.0 eq.) in DMF (30 ml) was added to the reaction mixture at room temperature and stirred at 80° C., for 4 hours. After completion of the reaction, the reaction mixture was diluted with water and extracted with ethyl acetate. The combined organic layers were washed with water, brine, dried over anhydrous sodium sulphate and the solvent was removed under reduced pressure. The crude product was purified over silica gel (100-200 mesh) column chromatography by eluting with 5% EtOAc/pet ether, this yielded 10.0 g (49.8%).

LCMS: (M+H): 303

$^1$H-NMR (400 MHz, CDCl$_3$); δ 1.3 (t, 3H), 4.3 (q, 2H), 5.3 (s, 1H), 8.0 (s, 1H), 8.6 (s, 1H).

Step 2

Synthesis of (5-bromo-3-chloropyridin-2-yl)acetonitrile

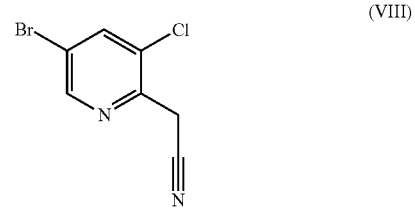 [SMILES: N#CCc1ncc(Br)cc1Cl]

(VIII)

To a solution of ethyl (5-bromo-3-chloropyridin-2-yl)(cyano)acetate (10.0 g, 1.0 eq.) in DMSO (30 ml) and water (5 ml) at room temperature, NaCl (636 mg, 0.33 eq) was added and the reaction mixture was stirred at 170 OC for one hour. After completion of reaction, the reaction mixture was diluted with water and extracted with ethyl acetate. The combined organic layers were washed with water, brine, dried over anhydrous sodium sulphate and the solvent was removed under reduced pressure. The crude product was purified over silica gel (100-200 mesh) column chromatography by eluting with 3% EtOAc/pet ether to yield 7.0 g (91.8%).

LCMS: (M−H): 228.8

$^1$H-NMR (400 MHz, CDCl$_3$); δ 4 (s, 2H) 7.9 (s, 1H), 8.6 (s, 1H).

Step 3

Synthesis of tert-butyl [2-(5-bromo-3-chloropyridin-2-yl)ethyl]carbamate

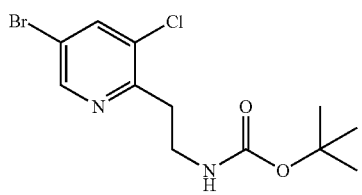

(IX)

The solution of (5-bromo-3-chloropyridin-2-yl)acetonitrile (2×3.5 g, 1.0 eq.) in methanol (2×28 ml) at 0° C., BOC anhydride (2×3.5 ml, 1.1 eq.), NiCl$_2$.6H$_2$O (2×1.08 g, 0.3 eq.), NaBH$_4$ (2×1.72 g, 3.0 eq.) were added and the reaction mixture was stirred at room temperature for 30 minutes. After completion of reaction the reaction mixture was concentrated under reduced pressure, the residue was diluted with water and extracted with ethyl acetate. The combined organic layers were washed with water, brine, dried over anhydrous sodium sulphate and the solvent was removed under reduced. The crude product was purified over silica gel (100-200 mesh) column chromatography by eluting with 10% EtOAc/pet ether to yield 5.0 g (49.2%).

LCMS: (M+H): 335

$^1$H-NMR (400 MHz, CDCl$_3$); δ 1.4 (s, 9H), 3.1 (m, 2H), 3.6 (m, 2H), 5.1 (br, 1H), 7.8 (s, 1H), 8.5 (s, 1H).

Step 4

Synthesis of 2-(5-bromo-3-chloropyridin-2-yl)ethanamine hydrochloride

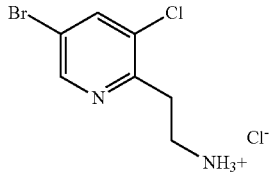

(X)

The solution of tert-butyl [2-(5-bromo-3-chloropyridin-2-yl)ethyl]carbamate (5.0 g, 1.0 eq.) in methanol (30 ml) at room temperature, methanolic HCl (50 ml) was added and the reaction mixture was stirred at 70° C., for one hour. After completion of reaction, the reaction mixture was concentrated under reduced pressure. The crude product was purified by ethyl acetate washings to yield 3.0 g (74%).

LCMS: (M+H): 235

$^1$H-NMR (400 MHz, D$_6$-DMSO); δ: 3.2 (m, 4H), 8.2 (br, 2H), 8.4 (s, 1H), 8.6 (s, 1H).

Step 5

Synthesis of N-[2-(5-bromo-3-chloropyridin-2-yl)ethyl]-2-(trifluoromethyl)benzamide

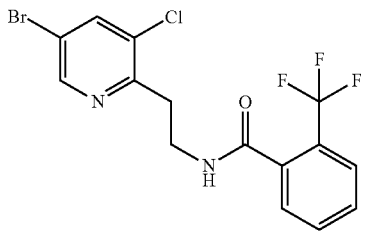 [SMILES: O=C(NCCc1ncc(Br)cc1Cl)c1ccccc1C(F)(F)F]

To a solution of 2-(5-bromo-3-chloropyridin-2-yl)ethanamine hydrochloride (3.0 g, 1.0 eq.) in THF (30 ml) at room temperature, TEA (4.6 ml, 3.0 eq.), 2-trifluoromethyl benzoic acid (2.3 g, 1.1 eq.), EDC.HCl (3.16 g, 1.5 eq.) were added and stirred for 15 minutes. Then HOBT (2.23 g, 1.5 eq.) was added to the reaction mixture and continued the reaction at same temperature for four hours. After completion of reaction, the reaction mixture was diluted with 2N HCl and extracted with ethyl acetate. The combined organic layers were washed with Na$_2$CO$_3$ solution, brine, dried over anhydrous sodium sulphate and the solvent was removed under reduced pressure to yield 3.0 g, (68.2%).

LCMS: (M+H): 407

$^1$H-NMR (400 MHz, CDCl$_3$); δ 3.2 (m, 2H), 4 (m, 2H), 6.6 (br, 1H), 7.5-7.6 (m, 3H), 7.7 (m, 1H), 7.8 (s, 1H), 8.4 (s, 1H).

Step 6

Synthesis of N-{2-[3-chloro-5-(1H-pyrazol-1-yl)pyridin-2-yl]ethyl}-2-(trifluoromethyl)benzamide (expl. 4)

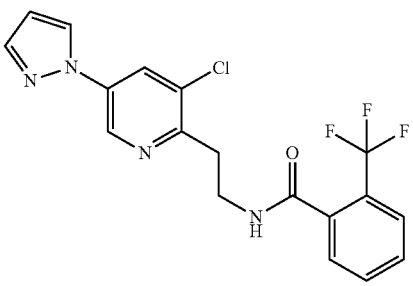 [SMILES: O=C(NCCc1ncc(-n2cccn2)cc1Cl)c1ccccc1C(F)(F)F]

To a stirred solution of N-[2-(5-bromo-3-chloropyridin-2-yl)ethyl]-2-(trifluoromethyl)benzamide (300 mg, 1.0 eq.) in acetonitrile (6 ml) at room temperature, pyrazole (60 mg, 1.2 eq.), copper(I) oxide (11 mg, 0.1 eq.), salicylaldoxime (20 mg, 0.2 eq.) cesium carbonate (480 mg, 2.0 eq.) were added and the reaction mixture was heated to 75° C., for 24 hours. After completion of reaction, the reaction mixture was diluted with ethyl acetate and filtered. The filtrate was concentrated under reduced pressure. The crude product was purified by prep HPLC to yield 90 mg (31%).

$^1$H-NMR (400 MHz, CDCl$_3$); δ CDCl3: 3.3 (m, 2H), 4 (m, 2H), 6.5 (s, 1H), 6.8 (br, 1H), 7.5-7.6 (m, 3H), 7.7 (m., 1H), 7.8 (s, 1H), 7.9 (s, 1H), 8.1 (s, 1H), 8.8 (s, 1H).

Preparation Example 2

Synthesis of N-{2-[5-chloro-6'-(trifluoromethyl)-3,3'-bipyridin-6-yl]ethyl}-2-(trifluoromethyl) benzamide (expl. 7)

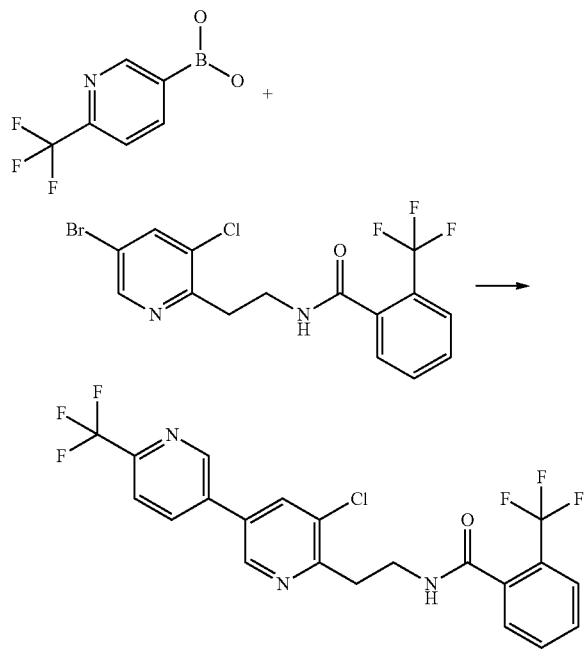

114 mg (0.28 mmol) N-[2-(5-bromo-3-chloropyridin-2-yl)ethyl]-2-(trifluoromethyl)benzamide (from step 5) and 53.5 mg (0.28 mmol) [6-(trifluoromethyl)pyridin-3-yl]boronic acid were dissolved in 4 mL dioxane. Thereafter, 20.7 mg (0.02 mmol) dichloro-bis(tricyclohexylphosphine) palladium(II) and 182.5 mg (0.56 mmol) cesium carbonate in 4 mL water were added and treated in a sealed microwave vial in a Biotage microwave oven (Initiator) at 100 OC for 20 minutes. The reaction mixture was filtered over a silica gel—sodium sulfate cartridge, the solvents were evaporated and the crude product was purified by silica gel chromatography (cyclohexane/ethyl acetate gradient) to afford 87 mg (65.6%) of the title compound as off-white solid.

¹H-NMR (400 MHz, d6-DMSO); δ 9.21 (s, 1H), 8.99 (s, 1H), 8.64 (t, 1H, NH), 8.53-8.51 (d, 1H), 8.46 (s, 1H), 8.06-8.04 (d, 1H), 7.78-7.51 (m, 4H), 3.72-3.67 (q, 2H), 3.22-3.19 (t, 2H).

Preparation Example 3

Step 1

Synthesis of 2-(5-bromo-3-chloropyridin-2-yl)-2,2-difluoroethanamine was performed in analogy to WO 2013/064460 A1 (referred as intermediates IIa-14 and IIa-15)

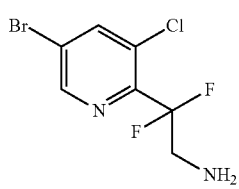

(XVII)

¹H-NMR (400 MHz, d6-DMSO); δ 8.78 (d, J=1.6 Hz, 1H), 8.52 (d, J=2.0 Hz, 1H), 3.37 (t, J=14.8 Hz, 2H), 1.72 (s, 2H).

Step 2

Synthesis of N-[2-(5-bromo-3-chloropyridin-2-yl)-2,2-difluoroethyl]-2-(trifluoromethyl)benzamide

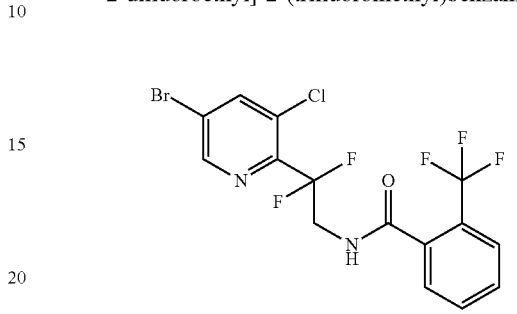

To a solution of 2-(5-bromo-3-chloropyridin-2-yl)-2,2-difluoroethanamine (2.56 g, 1.03 eq.) in dichloromethane (50 ml) at room temperature. TEA (3.38 ml, 3.0 eq.) and 2-trifluoromethyl benzoic acid chloride (1.68 g, 1.0 eq.) were added and stirred over night. After completion of reaction, the reaction mixture was diluted with water and extracted with dichloromethane. The solvent of the combined organic layers was evaporated under reduced pressure. The residue was purified by silica gel chromatography (cyclohexane/ethyl acetate) to yield 2.86 g (68.5%) as off-white solid.

¹H-NMR (400 MHz, d6-DMSO); δ 8.97 (t, 1H, NH), 8.80 (d, 1H), 8.56 (d, 1H), 7.77-7.63 (m, 3H), 7.45 (d, 1H), 4.28-4.19 (m, 2H).

Step 3

Synthesis of N-{2-[5-chloro-6'-(trifluoromethyl)-3,3'-bipyridin-6-yl]-2,2-difluoroethyl}-2-(trifluoromethyl) benzamide (expl. 11)

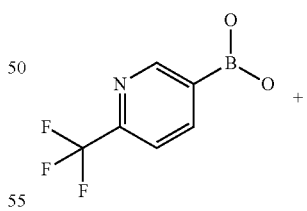

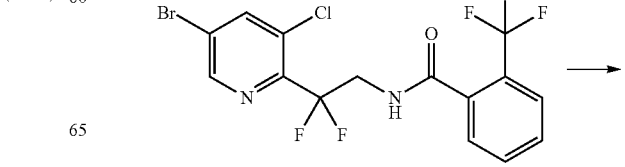

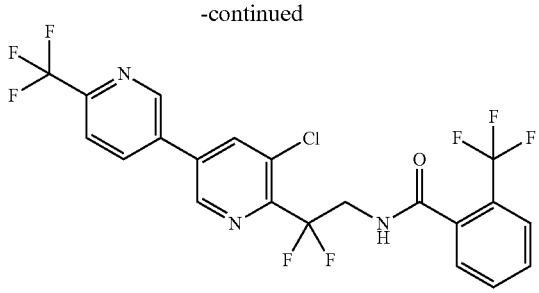

100 mg (0.22 mmol) N-[2-(5-bromo-3-chloropyridin-2-yl)-2,2-difluoroethyl]-2-(trifluoromethyl)benzamide (from step 2) and 47.3 mg (0.24 mmol) [6-(trifluoromethyl)pyridin-3-yl]boronic acid were dissolved in 3 mL dioxane. Thereafter, 16.5 mg (0.02 mmol) 1,1'-bis-(diphenylphosphino)-ferrocen)-palladium-dichloromethane complex and 1.12 mL 2 M (2.23 mmol) aqueous sodium carbonate solution were added and treated in a sealed microwave vial in a Biotage microwave oven (Initiator) at 100° C., for 20 minutes. The reaction mixture was filtered over a silica gel-sodium sulfate cartridge, the solvents were evaporated and the crude product was purified by preparative HPLC to afford 54.3 mg (42.95%) of the title compound as off-white solid.

$^1$H-NMR (400 MHz, d6-DMSO); δ 9.27 (s, 1H), 9.13 (s, 1H), 9.03 (t, 1H, NH), 8.68 (s, 1H), 8.60 (d, 1H), 8.11 (s, 1H), 7.79-7.64 (m, 3H), 7.49 (d, 1H), 4.37-4.28 (m, 2H).

According to the methods described above, the following compounds of general formula (I) have been prepared.

Compounds of formula (I-1)

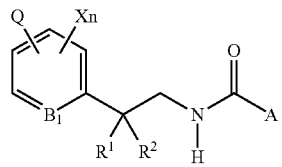

$R^1$, $R^2$, $B_1$, Q, X, n, A as defined by each individual structure.

| example No. | Formel | logP [1] (HCOOH) | (M+) + 1 (LC/MS) | 1H-NMR |
|---|---|---|---|---|
| 1 | | 1.21 | 395.0 | CDCl3: 3.3 (m, 2H), 4 (m, 2H), 6.5 (s, 1H), 6.8 (br, 1H), 7.5-7.6 (m, 3H), 7.7 (m, 1H), 7.8 (s, 1H), 7.9 (s, 1H), 8.1 (s, 1H), 9.8 (s, 1H) |
| 2 | | 3.65 | 463.0 | CDCl3: 3.3 (m, 2H), 4 (m, 2H), 6.7 (br, 1H), 7.5 (m, 3H), 7.7 (m, 1H), 7.9 (s, 1H), 8.1 (s, 1H), 8.2 (s, 1H), 8.8 (s, 1H) |
| 3 | | 3.68 | 463.0 | CDCl3: 3.2 (m, 2H), 3.7 (m, 2H), 7.2 (s, 1H), 7.5 (m, 1H), 7.6-7.8 (m, 3H), 8.5 (s, 1H), 8 6 (m, 1H), 8.9 (s, 1H), 9.1 (s, 1H) |
| 4 | | 2.69 | 395.1 | CDCl3: 3.3 (m, 2H), 4 (m, 2H), 6.5 (s, 1H), 6.8 (br, 1H), 7.5-7.6 (m, 3H), 7.7 (m, 1H), 7.8 (s, 1H), 7.9 (s, 1H), 8.1 (s, 1H), 8.8 (s, 1H) |

-continued
Compounds of formula (I-1)
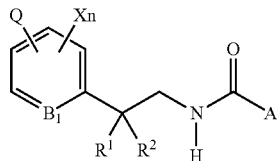
$R^1$, $R^2$, $B_1$, Q, X, n, A as defined by each individual structure.
| example No. | Formel | logP [1] (HCOOH) | (M+) + 1 (LC/MS) | 1H-NMR |
|---|---|---|---|---|
| 5 | | 2.06 | 396.1 | D6-DMSO: 3.2 (m, 2H), 3.7 (m, 2H), 7.5 (m, 1H), 7.6 (m, 1H), 7.7-7.8 (m, 2H), 8.3 (s, 1H), 8.5 (s, 1H), 8.7 (m, 1H), 9.1 (s, 1H), 9.4 (s, 1H) |
| 6 | | 3.0 | 440.0; 442.0 | NMR peak list |
| 7 | | 3.29 | 474.1 | NMR peak list |
| 8 | | 3.21 | 431.2 | NMR peak list |
| 9 | | 3.53 | 445.2 | NMR peak list |

-continued
Compounds of formula (I-1)
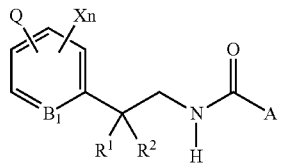
R¹, R², B₁, Q, X, n, A as defined by each individual structure.
| example No. | Formel | logP [1] (HCOOH) | (M+) + 1 (LC/MS) | 1H-NMR |
|---|---|---|---|---|
| 10 | | 2.84 | 460.2 | NMR peak list |
| 11 | | 3.42 | 510.2 | NMR peak list |
| 12 | | 3.21 | 476.2 | NMR peak list |
| 13 | | 1.86 | 456.2 | NMR peak list |

-continued
Compounds of formula (I-1)
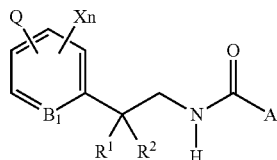
$R^1, R^2, B_1, Q, X, n, A$ as defined by each individual structure.
| example No. | Formel | logP [1) (HCOOH) | (M+) + 1 (LC/MS) | 1H-NMR |
|---|---|---|---|---|
| 14 | 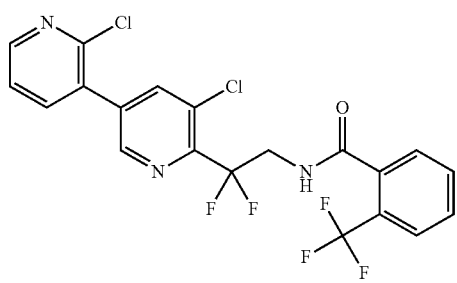 [SMILES: O=C(NCC(F)(F)c1ncc(-c2cccnc2Cl)cc1Cl)c1ccccc1C(F)(F)F] | 3.0 | 476.2 | NMR peak list |
| 15 | 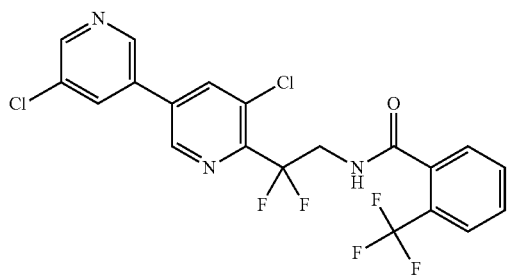 [SMILES: O=C(NCC(F)(F)c1ncc(-c2cncc(Cl)c2)cc1Cl)c1ccccc1C(F)(F)F] | 3.17 | 476.2 | NMR peak list |
| 16 | 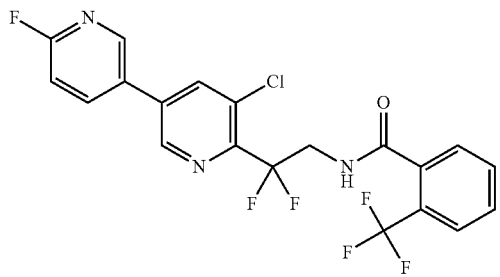 [SMILES: O=C(NCC(F)(F)c1ncc(-c2ccc(F)nc2)cc1Cl)c1ccccc1C(F)(F)F] | 3.02 | 460.0 | NMR peak list |
| 17 | 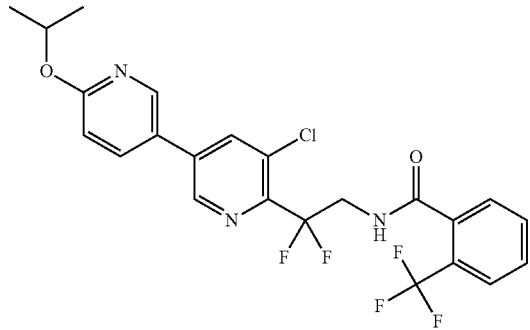 [SMILES: CC(C)Oc1ccc(-c2cnc(C(F)(F)CNC(=O)c3ccccc3C(F)(F)F)c(Cl)c2)cn1] | 4.15 | 500.3 | NMR peak list |

-continued
Compounds of formula (I-1)
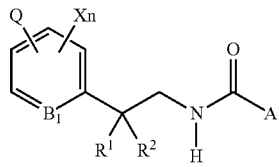
$R^1$, $R^2$, $B_1$, Q, X, n, A as defined by each individual structure.
| example No. | Formel | logP [1] (HCOOH) | (M+) + 1 (LC/MS) | 1H-NMR |
|---|---|---|---|---|
| 18 | | 3.68 | 512.2 | NMR peak list |
| 19 | | 2.27 | 442.2 | NMR peak list |
| 20 | | 3.94 | 540.2 | NMR peak list |
| 21 | | 2.88 | 476.2 | NMR peak list |

-continued
Compounds of formula (I-1)
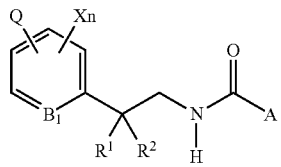
$R^1$, $R^2$, $B_1$, Q, X, n, A as defined by each individual structure.
| example No. | Formel | logP [1] (HCOOH) | (M+) + 1 (LC/MS) | 1H-NMR |
|---|---|---|---|---|
| 22 | | 2.0 | 442.2 | NMR peak list |
| 23 | | 2.96 | 460.2 | NMR peak list |
| 24 | | 3.17 | 476.1 | NMR peak list |
| 25 | | 3.84 | 512.1 | NMR peak list |

-continued
Compounds of formula (I-1)
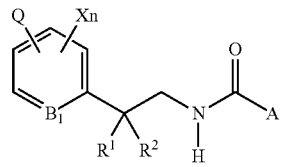
$R^1, R^2, B_1, Q, X, n, A$ as defined by each individual structure.
| example No. | Formel | logP [1] (HCOOH) | (M+) + 1 (LC/MS) | 1H-NMR |
|---|---|---|---|---|
| 26 | 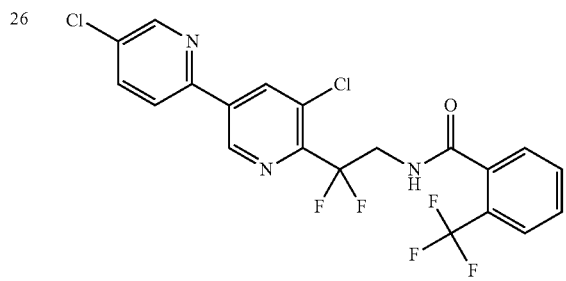 | | | |
| 27 | 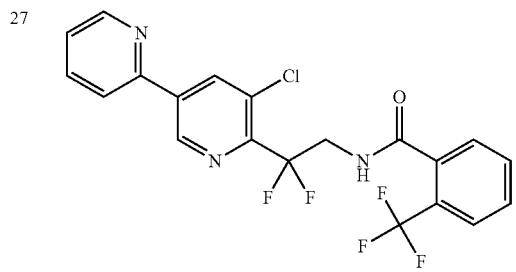 | | | |
| 28 | 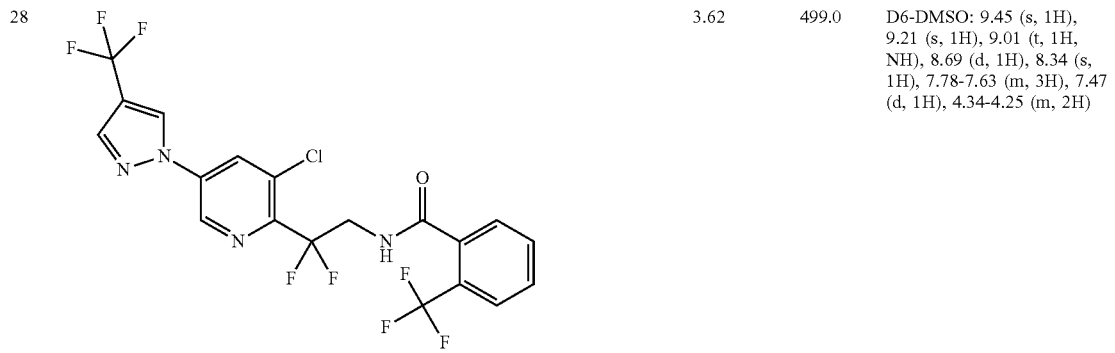 | 3.62 | 499.0 | D6-DMSO: 9.45 (s, 1H), 9.21 (s, 1H), 9.01 (t, 1H, NH), 8.69 (d, 1H), 8.34 (s, 1H), 7.78-7.63 (m, 3H), 7.47 (d, 1H), 4.34-4.25 (m, 2H) |
| 29 | 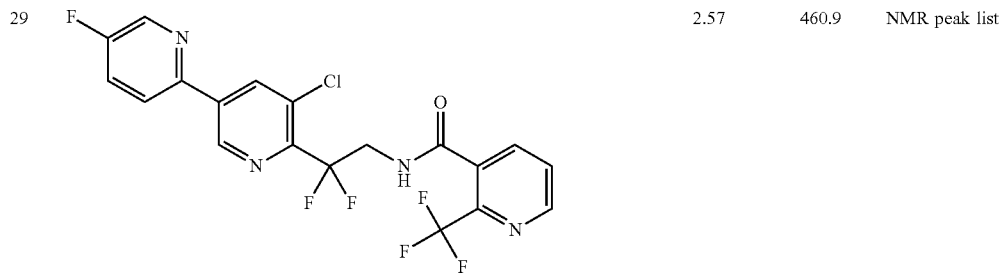 | 2.57 | 460.9 | NMR peak list |

-continued
Compounds of formula (I-1)
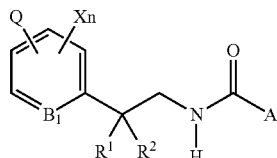
R¹, R², B₁, Q, X, n, A as defined by each individual structure.
| example No. | Formel | logP [1] (HCOOH) | (M+) + 1 (LC/MS) | 1H-NMR |
|---|---|---|---|---|
| 30 | | 2.75 | 461.9 | NMR peak list |
| 31 | | 3.94 | 455.0; 456.0 | NMR peak list |
| 32 | | 2.66 | 457.0 | NMR peak list |
| 33 | | 3.26 | 472.7 | NMR peak list |
| 34 | | 2.77 | 473.0 | NMR peak list |

-continued
Compounds of formula (I-1)
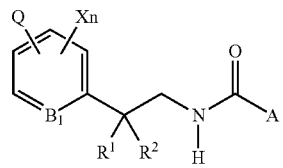
$R^1, R^2, B_1, Q, X, n, A$ as defined by each individual structure.
| example No. | Formel | logP [1] (HCOOH) | (M+) + 1 (LC/MS) | 1H-NMR |
|---|---|---|---|---|
| 35 | | 3.55 (neutral) | 506.1 | CDCl$_3$: 8.94 (d, 1H), 8.69 (d, 1H), 8.07 (dd, 1H), 7.98 (m, 1H), 7.85 (d, 1H), 7.69 (d, 1H), 7.58 (m, 3H), 6.48 (t, 1H, NH), 4.41-4.19 (m, 2H), 1.70 (d, 3H, CH$_3$) |
| 36 | | 3.17 | 507.0 | NMR peak list |
| 37 | | 3.79 | 452.0 | NMR peak list |
| 38 | | 1.69 | 453.0 | NMR peak list |
| 39 | | 2.99 | 455.9 | NMR peak list |

Compounds of formula (I-1)

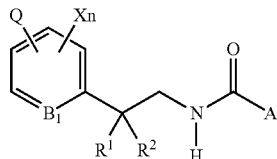

$R^1$, $R^2$, $B_1$, Q, X, n, A as defined by each individual structure.

| example No. | Formel | logP [1]) (HCOOH) | (M+) + 1 (LC/MS) | 1H-NMR |
|---|---|---|---|---|
| 40 | | 2.49 | 456.9 | NMR peak list |
| 41 | | 3.28 | 478.0 | D6-DMSO: 9.09 (s, 1H), 9.02 (t, 1H), 870-8.61 (m, 3H), 7.79-7.64 (m, 3H), 7.48 (d, 1H), 4.36-4.27 (m, 2H). |
| 42 | | 1.97 | 485.1 | D6-DMSO: 8.97 (t, 1H), 8.94 (d, 1H), 8.64 (d, 1H), 8.37 (d, 1H), 8.05-8.02 (dd, 1H), 7.78-7.71 (m, 2H), 7.65 (dd, 1H), 7.49 (d, 1H), 6.78 (d, 1H), 4.29-4.28 (m, 2H), 3.10 (s, 6H). |

NMR Peak Lists $^1$H-NMR data of selected examples are written in form of $^1$H-NMR-peak lists. The δ-value in ppm and the signal intensity are listed to each signal peak in round brackets. Between the δ-value—signal intensity pairs are semicolons as delimiters.

The peak list of an example has therefore the form:

$δ_1$ (intensity$_1$); $δ_2$ (intensity$_2$); . . . ; $δ_i$ (intensity$_i$); . . . ; $δ_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

Tetramethylsilane and/or the chemical shift of the used solvent, especially in the case of spectra measured in DMSO, have been used for calibrating. Therefore, tetramethylsilane peak can occur but not necessarily in NMR peak lists.

The $^1$H-NMR peak lists are similar to classical $^1$H-NMR prints and contain therefore usually all peaks, which are listed at classical NMR-interpretation.

Additionally they can show like classical $^1$H-NMR prints signals of solvents, stereoisomers of the target compounds, which are also object of the invention, and/or peaks of impurities.

The usual peaks of solvents, for example peaks of DMSO in DMSO-D6 and the peak of water, are given in the $^1$H-NMR peak lists to show compound signals in the delta-range of solvents and/or water. They have usually on average a high intensity.

The peaks of stereoisomers of the target compounds and/or peaks of impurities have usually on average a lower intensity than peaks of target compounds (for example with a purity>90%).

Such stereoisomers and/or impurities can be typical for the specific preparation process. Therefore, their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

Table with NMR Peaklists

Example 6: $^1$H-NMR(400.0 MHz, DMSO):
δ = 8.923(15.2); 8.918(15.5); 8.869(12.3); 8.862(12.3); 8.651(3.4); 8.637(6.9); 8.623(3.4); 8.371(16.0); 8.365(15.8); 8.319(8.0); 8.313(7.8); 8.298(8.5); 8.292(8.4); 7.775(6.9); 7.755(9.3); 7.737(3.1); 7.719(7.8); 7.701(5.6); 7.679(12.9); 7.658(13.6); 7.633(7.1); 7.614(2.7); 7.528(8.3); 7.509(6.9); 6.579(0.5); 4.038(0.5); 4.020(0.5); 3.700(4.0); 3.683(9.0); 3.667(9.2); 3.650(4.7); 3.324(76.3); 3.202(8.8); 3.184(14.3); 3.166(7.6); 3.147(0.4); 3.128(0.3); 2.676(0.9); 2.671(1.2); 2.667(0.9); 2.608(0.4); 2.541(1.0); 2.524(3.8); 2.511(66.7); 2.507(130.6); 2.502(171.1); 2.498(125.3); 2.494(61.7); 2.333(0.8); 2.329(1.1); 2.325(0.8); 1.989(2.0); 1.397(0.9); 1.271(1.2); 1.259(2.2); 1.244(1.6); 1.237(1.2); 1.193(0.6); 1.175(1.5); 1.169(3.6); 1.157(0.6); 0.008(0.6); 0.000(14.0); −0.009(0.5)

Example 7: $^1$H-NMR(400.0 MHz, DMSO):
δ = 9.213(10.8); 9.208(10.6); 8.998(15.2); 8.993(15.0); 8.663(3.3); 8.648(6.5); 8.634(3.2); 8.532(5.6); 8.527(5.4); 8.511(6.1); 8.506(6.0); 8.458(16.0); 8.453(15.2); 8.316(1.2); 8.058(11.2); 8.038(10.3); 7.777(6.9); 7.757(9.2); 7.739(3.0); 7.721(7.8); 7.702(5.5); 7.654(5.4); 7.635(7.0); 7.616(2.6); 7.532(8.2); 7.514(6.9); 4.319(0.4); 4.038(0.4); 4.020(0.4); 3.716(3.9); 3.699(8.9); 3.683(9.2); 3.666(4.5); 3.322(131.2); 3.224(8.7); 3.206(14.2); 3.188(7.5); 2.675(1.6); 2.671(2.1); 2.667(1.5); 2.541(1.3); 2.524(6.4); 2.510(127.0); 2.506(243.7); 2.502(313.6); 2.497(228.6); 2.493(112.2); 2.333(1.6); 2.329(2.2); 2.324(1.6); 1.989(1.5); 1.360(2.2); 1.193(0.4); 1.175(0.8); 1.157(0.4); 0.008(0.9); 0.000(23.2); −0.008(0.9)

Example 8: $^1$H-NMR(400.0 MHz, DMSO):
δ = 8.985(3.3); 8.971(6.8); 8.955(3.6); 8.942(14.3); 8.938(14.6); 8.523(15.6); 8.492(0.3); 8.412(14.2); 8.408(13.9); 8.317(0.8); 7.936(0.3); 7.857(9.5); 7.853(16.0); 7.849(9.9); 7.799(0.4); 7.781(7.3); 7.761(10.0); 7.747(3.3); 7.729(8.2); 7.710(5.7); 7.668(5.8); 7.649(7.3); 7.630(2.8); 7.472(8.6); 7.453(7.6); 7.215(13.2); 7.212(13.1); 4.326(3.3); 4.310(3.3); 4.289(7.5); 4.273(7.3); 4.251(3.9); 4.235(3.5); 3.345(159.1); 3.219(0.4); 3.205(0.3); 2.996(0.5); 2.711(0.5); 2.676(1.8); 2.672(2.3); 2.667(1.7); 2.542(130.3); 2.507(297.5); 2.503(386.0); 2.498(282.1); 2.434(0.7); 2.427(0.6); 2.406(0.3); 2.376(0.3); 2.368(0.7); 2.334(1.8); 2.329(2.3); 2.325(1.8); 2.292(0.5); 2.048(0.4); 1.259(0.5); 1.235(2.1); 0.146(0.5); 0.008(3.8); 0.000(101.9); −0.008(3.8); −0.021(0.4); −0.150(0.6)

Example 9: $^1$H-NMR(400.0 MHz, DMSO):
δ = 8.994(3.3); 8.979(7.2); 8.963(3.3); 8.757(14.2); 8.753(14.1); 8.439(0.4); 8.317(1.0); 8.177(14.4); 8.172(14.0); 7.872(0.4); 7.855(0.5); 7.782(7.1); 7.762(9.7); 7.750(3.4); 7.731(7.9); 7.713(5.8); 7.684(15.7); 7.680(16.0); 7.669(6.1); 7.650(7.2); 7.631(2.8); 7.569(0.3); 7.553(0.7); 7.533(0.5); 7.520(0.4); 7.504(0.5); 7.483(8.2); 7.464(7.2); 6.953(14.6); 6.948(14.3); 4.340(3.1); 4.325(3.4); 4.303(7.3); 4.288(7.0); 4.266(3.7); 4.251(3.4); 3.338(161.3); 3.229(0.5); 3.170(0.5); 2.712(0.4); 2.676(1.7); 2.671(2.5); 2.542(112.1); 2.507(320.9); 2.503(392.5); 2.498(281.0); 2.494(136.2); 2.447(0.8); 2.418(0.5); 2.395(0.4); 2.367(0.7); 2.346(0.6); 2.334(1.7); 2.329(2.3); 2.325(1.8); 2.291(0.5); 2.271(0.4); 2.186(0.4); 1.740(0.4); 1.685(0.3); 1.258(0.5); 1.235(1.9); 0.146(0.4); 0.008(4.2); 0.000(95.8); −0.008(3.4); −0.150(0.5)

Example 10: $^1$H-NMR(400.0 MHz, DMSO):
δ = 11.825(0.4); 9.108(15.4); 9.103(15.5); 9.036(3.5); 9.020(7.3); 8.998(9.8); 8.993(16.0); 8.989(9.2); 8.737(1.3); 8.732(1.6); 8.720(14.4); 8.713(14.8); 8.637(15.9); 8.632(15.6); 8.566(0.4); 8.470(1.2); 8.465(1.2); 8.363(4.6); 8.358(6.1); 8.352(4.4); 8.338(4.9); 8.331(6.0); 8.326(4.5); 8.317(2.4); 7.786(7.5); 7.766(10.1); 7.756(4.0); 7.737(8.3); 7.718(6.0); 7.673(6.2); 7.654(7.8); 7.635(3.0); 7.576(0.4); 7.551(0.6); 7.530(0.7); 7.487(8.7); 7.468(7.7); 7.448(1.0); 7.429(1.0); 7.202(0.4); 7.074(0.4); 6.945(0.6); 4.360(3.2); 4.345(3.3); 4.323(7.5); 4.308(7.1); 4.285(4.1); 4.271(3.7); 4.250(0.9); 4.233(0.8); 4.213(0.5); 4.197(0.4); 3.693(0.4); 3.602(0.4); 3.561(0.5); 3.536(0.4); 3.520(0.6); 3.475(0.7); 3.343(423.4); 3.197(0.6); 3.193(0.6); 3.141(0.5); 3.132(0.4); 3.098(0.4); 3.044(0.5); 2.996(0.9); 2.712(0.7); 2.676(4.0); 2.671(5.4); 2.667(4.1); 2.576(0.7); 2.564(0.9); 2.542(177.9); 2.525(13.8); 2.511(354.3); 2.507(712.0); 2.502(925.0); 2.498(662.6); 2.493(317.2); 2.450(1.2); 2.409(0.7); 2.392(0.7); 2.367(0.9); 2.334(4.1); 2.329(5.4); 2.325(3.9); 2.292(1.1); 2.253(0.5); 2.243(0.4); 2.075(0.4); 1.299(0.4); 1.259(0.9); 1.235(3.8); 0.854(0.5); 0.146(0.7); 0.008(6.7); 0.000(191.1); −0.009(6.0); −0.150(0.9); −3.686(0.4)

Example 11: $^1$H-NMR(400.0 MHz, DMSO):
δ = 9.268(11.5); 9.263(11.1); 9.127(15.1); 9.122(14.9); 9.043(3.5); 9.028(7.3); 9.012(3.4); 8.678(16.0); 8.673(14.9); 8.601(5.6); 8.596(5.5); 8.581(6.2); 8.576(6.1); 8.317(1.0); 8.111(11.7); 8.090(10.8); 7.787(7.0); 7.767(9.6); 7.756(3.3); 7.737(7.9); 7.718(5.6); 7.674(5.6); 7.655(7.1); 7.636(2.6); 7.491(8.4); 7.472(7.3); 4.371(3.1); 4.356(3.1); 4.334(7.1); 4.318(6.8); 4.296(3.5); 4.281(3.3); 3.477(0.3); 3.464(0.4); 3.449(0.4); 3.432(0.5); 3.346(284.9); 3.270(0.8); 2.996(12); 2.712(0.4); 2.677(1.7); 2.672(2.2); 2.668(1.6); 2.542(87.5); 2.525(6.4); 2.512(151.6); 2.507(295.7); 2.503(376.8); 2.498(265.0); 2.494(123.3); 2.437(0.4); 2.368(0.3); 2.334(1.7); 2.330(2.2); 2.325(1.6); 2.293(0.6); 1.259(0.4); 1.235(2.0); 0.008(2.7); 0.000(64.8); −0.008(2.0)

Example 12: $^1$H-NMR(400.0 MHz, DMSO):
δ = 9.059(12.7); 9.054(12.7); 9.027(3.2); 9.012(6.4); 8.996(3.1); 8.937(11.6); 8.930(11.2); 8.737(0.3); 8.732(0.3); 8.595(13.1); 8.591(12.6); 8.391(6.9); 8.384(6.6); 8.370(7.3); 8.363(7.2); 8.317(0.8); 7.785(6.2); 7.765(8.7); 7.753(3.1); 7.731(16.0); 7.710(12.3); 7.672(5.2); 7.653(6.4); 7.634(2.4); 7.485(7.5); 7.466(6.5); 4.356(2.8); 4.340(2.8); 4.319(6.4); 4.303(6.0); 4.282(3.3); 4.266(3.1); 4.235(0.2); 3.482(0.3); 3.448(0.5); 3.346(398.2); 3.279(1.0); 3.224(0.4); 2.996(1.1); 2.712(0.4); 2.676(1.7); 2.672(2.2); 2.667(1.6); 2.565(0.5); 2.542(91.2); 2.507(294.0); 2.503(376.0); 2.498(269.3); 2.434(0.4); 2.418(0.4); 2.368(0.5); 2.329(2.3); 2.325(1.8); 2.292(0.7); 1.298(0.3); 1.258(0.4); 1.235(2.1); 0.008(2.0); 0.000(42.2); −0.008(1.5)

Example 13: $^1$H-NMR(400.0 MHz, DMSO):
δ = 9.037(0.8); 9.021(1.7); 9.006(0.8); 8.715(3.4); 8.710(3.3); 8.577(1.8); 8.568(1.7); 8.564(1.6); 8.317(0.5); 8.289(3.5); 8.284(3.3); 7.786(2.2); 7.767(2.7); 7.751(0.8); 7.733(1.9); 7.714(1.4); 7.673(1.4); 7.655(1.7); 7.636(0.7); 7.487(2.0); 7.469(1.8); 7.427(1.0); 7.414(1.2); 7.408(1.1); 7.395(0.9); 4.377(0.8); 4.361(0.8); 4.340(1.7); 4.324(1.6); 4.303(0.9); 4.287(0.8); 3.492(0.4); 3.345(169.4); 2.995(0.7); 2.712(0.4); 2.676(1.1); 2.672(1.4); 2.667(1.0); 2.542(91.8); 2.507(182.7); 2.503(233.5); 2.498(169.2); 2.464(16.0); 2.368(0.5); 2.334(1.1); 2.329(1.5); 2.325(1.1); 1.235(1.4); 0.000(21.0)

Example 14: $^1$H-NMR(400.0 MHz, DMSO):
δ = 9.050(3.7); 9.035(7.3); 9.019(3.7); 8.992(0.6); 8.977(1.1); 8.963(0.6); 8.794(15.7); 8.790(16.0); 8.737(2.0);
8.732(2.0); 8.554(9.2); 8.549(9.8); 8.542(9.6); 8.537(9.4); 8.492(0.3); 8.468(1.9); 8.463(1.9); 8.380(15.8);
8.376(15.3); 8.316(1.5); 8.243(0.3); 8.062(8.7); 8.058(8.9); 8.043(9.8); 8.039(9.1); 7.973(0.3); 7.842(0.4);
7.824(0.4); 7.787(7.9); 7.767(10.6); 7.748(3.9); 7.730(9.6); 7.711(7.0); 7.674(6.8); 7.654(8.3); 7.636(11.8);
7.624(9.0); 7.618(8.6); 7.605(8.2); 7.583(0.3); 7.569(0.4); 7.525(0.4); 7.522(0.4); 7.478(9.2); 7.459(8.1); 7.430(1.2);
7.074(0.5); 6.947(0.4); 4.400(0.4); 4.382(3.4); 4.366(3.6); 4.343(8.0); 4.328(7.6); 4.306(4.0); 4.289(3.9); 4.271(0.8);
4.250(1.2); 4.234(1.2); 4.213(0.7); 4.198(0.8); 3.822(0.4); 3.810(0.3); 3.711(0.4); 3.684(0.4); 3.653(0.4); 3.620(0.4);
3.611(0.4); 3.595(0.5); 3.569(0.5); 3.494(0.8); 3.473(1.3); 3.344(1078.2); 3.203(0.5); 3.187(0.4); 3.167(0.4);
3.105(0.4); 2.996(1.5); 2.712(1.8); 2.676(3.5); 2.672(4.8); 2.667(3.6); 2.604(0.9); 2.599(0.7); 2.542(402.8);
2.507(608.4); 2.503(779.4); 2.498(566.5); 2.460(1.4); 2.452(1.3); 2.430(0.6); 2.368(1.7); 2.348(0.4); 2.329(4.6);
2.303(0.4); 2.292(1.0); 2.279(0.4); 2.075(0.4); 1.589(0.4); 1.298(0.6); 1.258(0.9); 1.235(4.3); 0.853(0.5); 0.008(2.4);
0.000(57.9)
Example 15: $^1$H-NMR(400.0 MHz, DMSO):
δ = 9.253(1.1); 9.210(0.7); 9.168(0.7); 9.142(0.8); 9.136(0.9); 9.112(2.3); 9.101(14.0); 9.097(14.3); 9.056(14.8);
9.051(14.9); 9.036(3.6); 9.020(6.8); 9.004(3.2); 8.936(0.6); 8.920(0.6); 8.872(0.4); 8.757(14.3); 8.751(14.7);
8.739(3.0); 8.734(2.3); 8.721(0.8); 8.716(0.9); 8.646(14.4); 8.641(14.4); 8.576(0.7); 8.570(1.5); 8.564(1.8);
8.524(9.8); 8.519(16.0); 8.513(8.9); 8.468(1.2); 8.413(1.3); 8.316(2.2); 8.102(0.9); 8.097(1.2);
7.787(6.9); 7.767(9.7); 7.756(4.1); 7.737(7.9); 7.718(5.7); 7.698(0.7); 7.673(5.7); 7.655(7.4); 7.635(3.0); 7.530(0.4);
7.488(7.9); 7.469(7.0); 7.445(0.9); 7.202(0.5); 7.077(0.4); 6.947(0.5); 4.360(3.2); 4.344(3.5); 4.322(7.0); 4.307(6.7);
4.285(3.9); 4.269(3.4); 4.241(0.6); 3.695(0.4); 3.650(0.4); 3.588(0.6); 3.559(0.6); 3.541(0.6); 3.521(1.0); 3.507(0.7);
3.483(0.9); 3.457(1.4); 3.433(2.0); 3.346(1498.8); 3.214(0.9); 3.195(0.6); 3.159(0.5); 3.157(0.5); 3.130(0.4);
3.084(0.4); 2.996(1.4); 2.712(1.0); 2.676(4.3); 2.672(5.9); 2.667(4.3); 2.647(0.4); 2.606(0.6); 2.566(0.7);
2.542(223.2); 2.511(366.4); 2.507(727.3); 2.503(943.2); 2.498(675.6); 2.494(321.3); 2.447(1.3); 2.443(1.2);
2.368(1.0); 2.334(4.3); 2.329(5.5); 2.325(4.1); 2.307(0.4); 2.293(1.4); 2.277(0.5); 1.297(0.8); 1259(1.0); 1.235(5.0);
0.853(0.5); 0.008(2.7); 0.000(73.6); −0.009(2.5)
Example 16: $^1$H-NMR(400.0 MHz, DMSO):
δ = 9.175(0.6); 9.170(0.6); 9.046(15.5); 9.041(15.7); 9.029(3.6); 9.013(7.1); 8.998(3.5); 8.980(0.5); 8.910(0.4);
8.802(0.6); 8.796(0.6); 8.773(10.5); 8.766(10.6); 8.737(0.8); 8.732(0.8); 8.574(16.0); 8.569(15.5); 8.534(4.0);
8.528(3.8); 8.513(5.8); 8.508(5.5); 8.507(5.4); 8.494(4.1); 8.487(4.4); 8.468(0.7); 8.338(0.5); 8.316(0.9);
8.307(0.8); 8.302(0.8); 7.786(6.9); 7.766(9.6); 7.755(3.7); 7.736(8.1); 7.717(5.9); 7.697(0.4); 7.673(5.7); 7.654(7.3);
7.635(2.8); 7.487(8.2); 7.469(7.3); 7.449(0.6); 7.440(0.5); 7.432(0.5); 7.414(6.7); 7.408(6.9); 7.393(6.6); 7.386(6.6);
7.361(0.4); 7.355(0.4); 7.340(0.4); 7.334(0.3); 4.359(3.1); 4.343(3.1); 4.322(7.3); 4.306(7.0); 4.284(4.0); 4.268(3.7);
4.251(0.6); 4.236(0.5); 3.461(0.3); 3.438(0.5); 3.347(514.5); 2.997(1.2); 2.713(1.0); 2.682(0.7); 2.677(1.3);
2.672(1.7); 2.668(1.2); 2.575(0.3); 2.567(0.3); 2.543(310.0); 2.526(4.3); 2.512(116.7); 2.508(235.4); 2.503(304.9);
2.499(214.6); 2.494(99.4); 2.369(1.1); 2.339(0.8); 2.334(1.4); 2.330(1.9); 2.325(1.4); 2.321(0.7); 2.295(0.5);
1.258(0.4); 1.234(1.7); 0.008(0.8); 0.000(21.2); −0.009(0.6)
Example 17: $^1$H-NMR(400.0 MHz, DMSO):
δ = 9.012(0.7); 8.996(1.4); 8.985(2.9); 8.981(3.1); 8.680(2.2); 8.673(2.2); 8.467(2.6); 8.462(2.4); 8.211(1.4);
8.204(1.3); 8.189(1.4); 8.183(1.3); 7.784(1.2); 7.764(1.7); 7.753(0.6); 7.734(1.5); 7.716(1.0); 7.671(1.0); 7.652(1.3);
7.633(0.5); 7.486(1.5); 7.467(1.3); 6.913(2.2); 6.892(2.2); 5.353(0.4); 5.337(1.1); 5.322(1.5); 5.306(1.1); 5.291(0.4);
4.349(0.6); 4.334(0.6); 4.312(1.2); 4.296(1.2); 4.275(0.6); 4.259(0.6); 3.344(125.5); 2.677(0.4); 2.672(0.5);
2.668(0.4); 2.543(48.1); 2.508(71.1); 2.503(88.8); 2.499(63.0); 2.335(0.4); 2.330(0.5); 2.326(0.4); 1.335(16.0);
1.319(15.9); 1302(0.3); 1235(0.5); 0.008(0.5); 0.000(10.5); −0.008(0.4)
Example 18: $^1$H-NMR(400.0 MHz, DMSO):
δ = 9.330(0.4); 9.159(2.0); 9.155(1.9); 9.127(0.5); 9.050(3.0); 9.035(6.2); 9.020(3.3); 8.797(12.7); 8.783(12.5);
8.729(0.3); 8.715(2.0); 8.711(1.9); 8.384(13.3); 8.380(12.5); 8.316(2.0); 8.190(1.3); 8.130(13.6); 8.110(15.6);
7.820(0.9); 7.797(16.0); 7.787(7.3); 7.777(15.2); 7.767(9.5); 7.748(2.7); 7.730(7.1); 7.711(5.0); 7.674(5.6);
7.655(6.9); 7.636(2.6); 7.544(0.4); 7.539(0.4); 7.528(0.5); 7.519(0.8); 7.507(0.6); 7.485(2.1); 7.474(7.8); 7.456(7.0);
7.440(1.0); 7.433(1.1); 7.422(0.4); 7.417(0.5); 7.381(1.1); 7.358(0.8); 7.345(0.8); 7.320(0.4); 7.204(0.4); 7.162(0.7);
7.142(1.0); 7.122(0.6); 7.077(0.4); 6.948(0.5); 4.376(2.6); 4.361(2.9); 4.339(6.1); 4.323(6.2); 4.302(3.3); 4.285(3.0);
4.134(0.4); 4.097(0.5); 4.083(0.7); 4.064(0.6); 4.055(0.6); 4.039(0.5); 4.029(0.4); 4.013(0.4); 3.613(0.3); 3.541(0.3);
3.502(0.5); 3.480(0.8); 3.468(0.6); 3.348(1157.7); 3.264(1.5); 3.237(1.3); 3.207(0.7); 3.168(0.5); 3.139(0.4);
3.125(0.4); 2.996(2.3); 2.713(1.4); 2.676(2.8); 2.672(3.6); 2.667(2.5); 2.542(395.9); 2.525(10.0); 2.512(244.1);
2.507(480.0); 2.503(615.7); 2.498(438.2); 2.494(209.4); 2.395(0.6); 2.369(1.7); 2.334(3.0); 2.329(3.8); 2.325(2.8);
2.294(1.1); 2.270(0.4); 2.075(0.4); 1.298(0.6); 1.259(1.0); 1.235(4.1); 0.854(0.6); 0.008(1.7); 0.000(47.5); −0.008(1.7)
Example 19: $^1$H-NMR(400.0 MHz, DMSO):
δ = 9.080(12.1); 9.075(12.4); 9.055(15.8); 9.050(16.0); 9.028(3.6); 9.012(7.5); 8.997(3.6); 8.704(8.3); 8.701(8.7);
8.692(8.8); 8.689(8.7); 8.572(16.0); 8.567(15.5); 8.315(4.9); 8.311(6.6); 8.305(4.8); 8.295(5.1); 8.290(6.8);
8.285(4.8); 7.784(7.7); 7.765(10.6); 7.755(3.8); 7.736(8.7); 7.717(6.1); 7.672(6.1); 7.653(7.9); 7.634(3.0);
7.600(6.4); 7.588(6.4); 7.580(6.4); 7.568(6.0); 7.490(9.1); 7.471(8.0); 4.364(3.5); 4.348(3.5); 4.326(8.0); 4.311(7.7);
4.289(4.0); 4.273(3.7); 3.363(43.0); 2.996(0.8); 2.676(1.4); 2.672(2.0); 2.667(1.5); 2.542(42.8); 2.525(5.5);
2.511(128.3); 2.507(256.3); 2.503(332.5); 2.498(238.4); 2.469(0.8); 2.464(0.8); 2.444(0.4); 2.334(1.6); 2.328(2.1);
2.325(1.5); 2.292(0.6); 1.259(0.4); 1.235(1.7); 0.146(0.6); 0.008(4.5); 0.000(119.3); −0.009(4.7); −0.150(0.5)
Example 20: $^1$H-NMR(400.0 MHz, DMSO):
δ = 9.022(13.0); 9.017(14.1); 9.003(5.9); 8.988(2.7); 8.740(9.9); 8.734(9.8); 8.525(11.8); 8.520(11.6); 8.349(6.3);
8.343(6.0); 8.328(6.6); 8.321(6.5); 7.784(5.5); 7.765(7.6); 7.753(2.5); 7.735(6.2); 7.716(4.4); 7.671(4.4); 7.652(5.6);
7.633(2.1); 7.487(6.6); 7.468(5.7); 7.187(9.8); 7.165(9.6); 5.117(4.7); 5.095(15.3); 5.072(16.0); 5.049(5.5);
4.354(2.4); 4.339(2.4); 4.317(5.5); 4.301(5.2); 4.280(2.7); 4.264(2.6); 3.348(120.7); 2.996(0.5); 2.712(0.6);
2.676(1.2); 2.672(1.6); 2.667(1.2); 2.542(181.5); 2.525(4.7); 2.511(108.5); 2.507(214.1); 2.503(276.4);
2.498(197.6); 2.494(94.7); 2.368(0.7); 2.334(1.3); 2.329(1.7); 2.325(1.2); 2.292(0.4); 1.259(0.4); 1.235(1.5);
0.146(0.4); 0.008(3.5); 0.000(88.9); −0.009(3.0); −0.150(0.3)
Example 21: $^1$H-NMR(400.0 MHz, DMSO):
δ = 9.052(2.3); 9.037(4.8); 9.021(2.4); 8.813(10.2); 8.808(10.4); 8.717(15.0); 8.663(8.4); 8.650(8.6); 8.410(10.5);
8.406(10.3); 8.317(1.0); 7.781(11.1); 7.768(16.0); 7.749(2.2); 7.732(5.5); 7.713(4.0); 7.674(3.9); 7.654(4.9);
7.636(1.8); 7.482(5.8); 7.463(5.1); 4.385(2.1); 4.369(2.1); 4.347(4.9); 4.331(4.8); 4.309(2.5); 4.294(2.3); 3.489(0.4);
3.338(261.5); 3.158(0.5); 2.712(0.4); 2.676(2.0); 2.671(2.7); 2.667(2.0); 2.606(0.8); 2.590(0.4); 2.542(73.9);

2.525(7.5); 2.511(173.2); 2.507(346.8); 2.503(451.7); 2.498(324.5); 2.494(155.9); 2.462(0.9); 2.451(0.6); 2.334(2.0); 2.329(2.7); 2.325(2.0); 2.291(0.6); 1.297(0.3); 1.258(0.5); 1.235(2.2); 0.145(0.4); 0.008(3.2); 0.000(88.9); −0.009(3.0); −0.150(0.4)

Example 22: $^1$H-NMR(400.0 MHz, DMSO):
δ = 9.106(11.4); 9.101(11.3); 9.030(2.6); 9.015(5.3); 8.999(2.5); 8.754(15.2); 8.750(9.8); 8.742(10.3); 8.738(16.0); 8.615(11.7); 8.610(11.2); 8.317(0.7); 7.931(15.6); 7.927(10.0); 7.920(9.9); 7.916(15.0); 7.782(5.3); 7.762(7.4); 7.754(2.6); 7.734(6.2); 7.716(4.4); 7.670(4.3); 7.651(5.5); 7.632(2.1); 7.483(6.3); 7.465(5.7); 4.361(2.4); 4.346(2.5); 4.324(5.6); 4.309(5.4); 4.287(2.8); 4.271(2.6); 3.475(0.4); 3.348(116.6); 2.996(1.7); 2.712(0.7); 2.676(1.2); 2.672(1.7); 2.667(1.2); 2.542(220.2); 2.525(4.5); 2.512(110.6); 2.507(220.2); 2.503(284.7); 2.498(202.9); 2.494(95.6); 2.445(0.4); 2.433(0.4); 2.369(0.9); 2.334(1.4); 2.329(1.8); 2.325(1.3); 2.292(0.4); 1.259(0.4); 1.235(1.7); 0.008(2.0); 0.000(51.0); −0.009(17)

Example 23: $^1$H-NMR(400.0 MHz, DMSO):
δ = 9.312(0.8); 9.152(15.1); 9.148(15.4); 9.038(3.6); 9.023(7.4); 9.007(3.5); 8.977(0.5); 8.935(0.6); 8.738(1.0); 8.733(1.0); 8.679(15.8); 8.674(15.5); 8.469(1.0); 8.464(1.0); 8.423(12.7); 8.410(13.5); 8.373(0.8); 8.360(0.8); 8.317(0.8); 7.958(0.6); 7.946(0.6); 7.922(8.2); 7.918(5.4); 7.913(5.1); 7.909(7.8); 7.835(1.1); 7.805(16.0); 7.783(7.5); 7.764(10.4); 7.754(4.3); 7.735(8.5); 7.717(6.4); 7.700(0.6); 7.672(6.2); 7.653(7.8); 7.634(3.0); 7.504(0.5); 7.482(8.7); 7.463(7.9); 7.449(1.2); 7.430(0.6); 7.360(0.9); 4.359(3.3); 4.344(3.4); 4.322(7.7); 4.306(7.4); 4.285(4.3); 4.270(3.9); 4.250(0.9); 4.236(0.7); 4.215(0.3); 4.197(0.4); 3.460(0.4); 3.455(0.4); 3.441(0.6); 3.347(477.2); 3.249(0.4); 3.243(0.5); 2.996(1.2); 2.712(1.2); 2.677(1.7); 2.672(2.4); 2.667(1.7); 2.571(0.7); 2.565(0.8); 2.542(310.6); 2.525(6.8); 2.512(150.2); 2.507(301.9); 2.503(394.3); 2.498(282.4); 2.494(135.5); 2.468(0.9); 2.457(0.6); 2.424(0.4); 2.368(1.4); 2.334(1.8); 2.330(2.3); 2.325(1.8); 2.293(0.6); 1.298(0.4); 1.259(0.6); 1.234(2.3); 0.008(1.9); 0.000(49.2); −0.008(1.7)

Example 24: $^1$H-NMR(400.0 MHz, DMSO):
δ = 10.952(1.2); 9.137(14.9); 9.133(14.2); 9.035(3.9); 9.021(7.6); 9.006(3.6); 8.978(1.0); 8.682(15.9); 8.677(14.8); 8.583(12.6); 8.570(13.2); 8.317(6.5); 8.119(15.7); 8.116(15.0); 7.968(10.6); 7.964(8.9); 7.954(9.7); 7.950(9.0); 7.784(7.4); 7.763(10.2); 7.752(3.5); 7.735(8.1); 7.716(6.3); 7.672(5.9); 7.653(7.7); 7.632(2.9); 7.494(1.2); 7.481(8.7); 7.463(7.6); 7.431(1.1); 7.201(1.4); 7.074(1.3); 6.946(1.4); 6.027(1.0); 5.587(1.0); 4.818(1.1); 4.356(3.6); 4.341(3.5); 4.318(7.3); 4.303(6.7); 4.279(4.3); 4.265(3.9); 4.233(1.2); 4.213(1.2); 4.019(1.1); 4.012(1.0); 3.831(1.2); 3.796(1.1); 3.758(1.0); 3.739(1.1); 3.721(1.3); 3.719(1.1); 3.710(1.2); 3.661(1.4); 3.639(1.3); 3.629(1.3); 3.600(1.4); 3.584(1.7); 3.576(1.7); 3.526(2.1); 3.501(2.6); 3.459(3.0); 3.346(2916.1); 3.268(3.1); 3.250(2.3); 3.243(2.8); 3.209(1.7); 3.076(1.1); 3.043(1.0); 2.995(2.0); 2.872(1.0); 2.711(3.1); 2.696(1.0); 2.676(11.7); 2.671(16.0); 2.667(11.6); 2.588(2.5); 2.571(4.1); 2.542(935.2); 2.525(45.6); 2.511(1037.1); 2.507(2048.7); 2.502(2630.7); 2.498(1866.0); 2.493(879.5); 2.396(1.8); 2.368(3.9); 2.334(11.3); 2.329(15.5); 2.325(11.6); 2.320(5.9); 2.292(3.5); 2.204(1.1); 1.298(2.2); 1.259(3.6); 1235(13.3); 0.854(1.6); 0.145(1.0); 0.008(9.6); 0.000(279.5); −0.009(10.0); −0.017(1.5); −0.149(1.3); −3.117(1.1); −3.268(1.0)

Example 25: $^1$H-NMR(400.0 MHz, DMSO):
δ = 9.171(3.4); 9.166(3.4); 9.045(0.8); 9.029(1.7); 9.014(0.8); 8.734(3.5); 8.730(3.4); 8.191(16.0); 7.786(1.8); 7.767(2.4); 7.754(0.8); 7.736(2.0); 7.717(1.4); 7.674(1.4); 7.655(1.8); 7.636(0.7); 7.479(2.0); 7.460(1.8); 4.352(0.8); 4.337(0.8); 4.314(1.8); 4.299(1.6); 4.277(0.9); 4.261(0.8); 3.347(188.4); 2.996(0.6); 2.712(0.4); 2.677(0.6); 2.672(0.8); 2.667(0.6); 2.542(100.9); 2.525(2.2); 2.512(51.3); 2.507(101.9); 2.503(131.5); 2.498(93.5); 2.494(44.2); 2.368(0.4); 2.334(0.6); 2.329(0.8); 2.325(0.6); 1.235(0.7); 0.008(0.5); 0.000(12.9); −0.009(0.4)

Example 28: $^1$H-NMR(400.0 MHz, DMSO):
δ = 9.522(0.5); 9.471(0.6); 9.453(0.8); 9.439(11.7); 9.328(0.4); 9.214(11.7); 9.208(11.7); 9.156(0.5); 9.094(0.4); 9.028(2.6); 9.012(5.4); 8.997(2.6); 8.970(0.3); 8.953(0.4); 8.847(0.6); 8.785(0.3); 8.715(0.6); 8.710(0.7); 8.689(11.1); 8.684(10.9); 8.429(0.8); 8.399(16.0); 8.316(2.0); 8.173(0.3); 8.109(0.3); 7.992(0.7); 7.960(0.4); 7.938(0.5); 7.879(0.8); 7.856(0.4); 7.841(0.4); 7.817(0.5); 7.801(0.5); 7.780(5.4); 7.759(7.6); 7.732(6.2); 7.714(4.4); 7.670(4.4); 7.650(5.5); 7.631(2.1); 7.523(0.4); 7.517(0.4); 7.500(0.5); 7.454(5.6); 5.757(1.3); 4.338(2.5); 4.322(2.7); 4.301(5.7); 4.286(5.4); 4.264(3.0); 4.249(2.7); 4.033(0.4); 4.009(0.3); 3.551(0.4); 3.483(0.5); 3.463(0.7); 3.447(0.6); 3.438(0.5); 3.424(1.0); 3.406(1.1); 3.390(2.1); 3.339(1821.8); 3.306(2.8); 3.300(2.3); 3.283(0.7); 3.275(0.8); 3.264(1.0); 3.250(1.0); 3.169(0.3); 2.891(0.9); 2.731(0.8); 2.677(2.5); 2.672(3.5); 2.668(2.5); 2.592(0.3); 2.525(9.1); 2.512(216.0); 2.507(427.4); 2.503(558.1); 2.498(396.7); 2.494(186.4); 2.469(1.1); 2.429(0.4); 2.334(2.6); 2.330(3.4); 2.325(2.5); 1.386(1.9); 1.235(0.6); 1.175(0.7); 1.166(1.2); 1.150(0.6); 0.146(2.0); 0.021(0.7); 0.018(1.0); 0.008(20.0); 0.000(511.9); −0.009(17.4); −0.025(0.5); −0.034(0.4); −0.040(0.4); −0.150(2.0)

Example 29: $^1$H-NMR (400.0 MHz, d$_6$-DMSO):
δ = 9.202 (3.9); 9.187 (8.0); 9.172 (3.8); 9.048 (15.2); 9.043 (15.4); 8.810 (8.3); 8.798 (8.3); 8.776 (11.4); 8.770 (11.6); 8.584 (16.0); 8.580 (15.5); 8.538 (3.8); 8.531 (3.7); 8.517 (6.3); 8.511 (6.0); 8.497 (4.0); 8.490 (3.8); 7.952 (7.1); 7.934 (8.9); 7.807 (7.2); 7.795 (7.2); 7.788 (6.0); 7.776 (5.6); 7.418 (6.8); 7.411 (6.9); 7.397 (6.8); 7.390 (6.6); 4.393 (3.5); 4.377 (3.5); 4.355 (7.9); 4.339 (7.5); 4.317 (4.0); 4.302 (3.7); 4.056 (0.4); 4.038 (1.2); 4.021 (1.2); 4.003 (0.4); 3.331 (78.7); 2.677 (0.6); 2.673 (0.9); 2.668 (0.7); 2.508 (100.2); 2.504 (128.0); 2.499 (96.0); 2.335 (0.6); 2.330 (0.8); 2.326 (0.6); 1.990 (5.1); 1.194 (1.4); 1.176 (2.7); 1.158 (1.4); 0.146 (0.9); 0.007 (9.0); 0.000 (176.8); −0.008 (9.2); −0.150 (0.9)

Example 33: $^1$H-NMR (400.0 MHz, d$_6$-DMSO):
δ = 9.279 (3.2); 9.264 (6.8); 9.248 (3.3); 9.039 (13.4); 9.034 (16.0); 9.024 (12.6); 8.976 (12.5); 8.970 (10.3); 8.776 (9.4); 8.770 (9.7); 8.595 (14.1); 8.590 (13.8); 8.539 (3.3); 8.532 (3.2); 8.518 (5.3); 8.512 (5.1); 8.498 (3.5); 8.491 (3.3); 7.420 (5.9); 7.413 (6.0); 7.399 (5.9); 7.392 (5.8); 4.446 (3.0); 4.430 (3.0); 4.408 (6.9); 4.392 (6.5); 4.370 (3.5); 4.354 (3.2); 4.056 (0.7); 4.038 (2.1); 4.021 (2.1); 4.003 (0.7); 3.331 (96.5); 2.678 (0.7); 2.673 (0.9); 2.668 (0.6); 2.526 (2.4); 2.512 (51.5); 2.508 (100.5); 2.504 (129.9); 2.499 (95.7); 2.335 (0.6); 2.331 (0.9); 2.326 (0.6); 1.990 (8.9); 1.194 (2.3); 1.176 (4.6); 1.158 (2.3); 0.146 (0.8); 0.008 (7.5); 0.000 (171.7); −0.008 (7.4); −0.150 (0.8)

Example 31: $^1$H-NMR (400.0 MHz, CDCl$_3$):
δ = 8.604 (5.7); 8.600 (6.0); 7.908 (6.2); 7.903 (6.4); 7.791 (2.7); 7.691 (3.4); 7.672 (3.9); 7.596 (1.1); 7.579 (3.1); 7.555 (6.3); 7.550 (3.7); 7.542 (7.9); 7.533 (6.4); 7.521 (11.7); 7.504 (3.3); 7.314 (1.1); 7.306 (1.1); 7.297 (1.3); 7.291 (1.9); 7.284 (1.4); 7.275 (2.0); 7.262 (69.8); 7.211 (4.8); 7.190 (8.7); 7.169 (4.2); 6.998 (0.4); 6.833 (1.9); 6.824 (1.9); 6.811 (1.7); 6.802 (1.7); 6.584 (1.2); 6.570 (2.0); 6.557 (1.1); 5.516 (1.2); 4.376 (0.9); 4.361 (0.9); 4.341 (1.7); 4.326 (2.5); 4.310 (0.9); 4.291 (1.8); 4.274 (2.9); 4.257 (1.7); 4.236 (2.4); 4.220 (2.3); 4.200 (0.8); 4.185 (0.8); 1.956 (15.9); 1.902 (16.0); 1.571 (97.8); 1299 (0.6); 1.282 (0.7); 1.266 (1.5); 1.250 (2.0); 0.000 (63.6)

Example 32: $^1$H-NMR (400.0 MHz, CDCl$_3$):
δ = 8.761 (0.4); 8.749 (0.4); 8.617 (0.7); 8.613 (0.7); 8.441 (0.5); 8.435 (0.6); 7.942 (0.8); 7.937 (0.8); 7.920 (0.4); 7.901 (0.4); 7.570 (0.4); 7.558 (0.4); 7.550 (0.4); 7.538 (0.3); 7.264 (5.1); 7.111 (0.4); 7.104 (0.4); 7.090 (0.3); 7.083 (0.3); 1.960 (2.0); 1.907 (2.0); 1.602 (16.0); 0.000 (4.7)

-continued

Example 33: $^1$H-NMR (400.0 MHz, CDCl$_3$):
δ = 8.632 (7.5); 8.630 (7.7); 8.610 (6.5); 8.607 (6.8); 7.931 (7.6); 7.855 (3.4); 7.851 (3.5); 7.849 (3.5); 7.834 (4.0); 7.831 (4.0); 7.828 (3.9); 7.692 (3.9); 7.673 (4.9); 7.602 (1.3); 7.585 (3.6); 7.566 (4.4); 7.548 (3.9); 7.528 (9.7); 7.509 (4.7); 7.490 (6.2); 7.470 (5.4); 7.263 (50.1); 6.497 (2.9); 5.302 (0.6); 4.387 (1.0); 4.372 (1.0); 4.352 (1.8); 4.337 (2.6); 4.321 (1.1); 4.301 (1.9); 4.285 (1.8); 4.269 (1.8); 4.253 (1.9); 4.231 (2.6); 4.216 (2.6); 4.196 (1.1); 4.180 (1.0); 2.047 (1.1); 1.957 (15.8); 1.903 (16.0); 1575 (65.2); 1.426 (2.9); 1.278 (0.7); 1256 (1.8); 0.000 (47.8)

Example 34: $^1$H-NMR (400.0 MHz, CDCl$_3$):
δ = 8.762 (3.3); 8.751 (3.4); 8.625 (6.0); 8.620 (6.2); 8.611 (5.5); 8.605 (5.4); 7.948 (6.5); 7.943 (6.4); 7.919 (3.2); 7.899 (3.6); 7.854 (3.3); 7.848 (3.4); 7.834 (3.7); 7.827 (3.7); 7.568 (3.0); 7.557 (3.0); 7.549 (2.8); 7.537 (2.7); 7.521 (0.7); 7.493 (5.9); 7.473 (5.4); 7.262 (90.5); 6.998 (0.5); 6.592 (1.2); 6.578 (2.0); 6.565 (1.2); 5.302 (1.2); 4.397 (1.0); 4.381 (1.0); 4.362 (1.6); 4.346 (2.1); 4.329 (0.9); 4.309 (1.7); 4.293 (1.6); 4.273 (1.6); 4.258 (1.6); 4.238 (2.6); 4.223 (2.5); 4.203 (1.0); 4.188 (0.9); 4.131 (0.7); 4.113 (0.7); 2.047 (2.9); 1.957 (16.0); 1.904 (16.0); 1.843 (0.4); 1.558 (131.4); 1.278 (0.8); 1.260 (1.7); 1.242 (0.8); 0.146 (0.4); 0.000 (82.5); −0.008 (3.9); −0.150 (0.4)

Example 36: $^1$H-NMR (601.6 MHz, CDCl$_3$):
δ = 19.961 (0.7); 8.941 (6.3); 8.761 (3.5); 8.754 (3.9); 8.680 (7.5); 8.067 (3.6); 8.054 (3.9); 8.000 (7.9); 7.919 (3.1); 7.907 (3.3); 7.848 (5.2); 7.835 (4.6); 7.567 (2.6); 7.555 (3.2); 7.547 (2.4); 7.436 (0.8); 7.265 (146.9); 7.089 (0.9); 6.592 (1.0); 4.388 (0.8); 4.375 (1.1); 4.363 (1.7); 4.353 (1.1); 4.340 (1.1); 4.328 (1.2); 4.269 (1.8); 4.259 (1.7); 4.245 (3.1); 4.235 (2.9); 4.222 (1.3); 4.211 (1.3); 2.580 (0.7); 1.960 (12.0); 1.925 (12.0); 1.697 (6.2); 1.690 (6.4); 1.678 (6.6); 1.673 (6.6); 1665 (6.6); 1.653 (8.3); 1.627 (10.4); 1619 (12.2); 1.608 (16.0); 1.431 (1.1); 1.396 (0.7); 1.254 (2.1); 0.069 (23.0); 0.067 (31.4); 0.065 (28.1); 0.000 (54.1); −0.002 (40.1); −0.005 (22.0)

Example 37: $^1$H-NMR (400.0 MHz, CDCl$_3$):
δ = 8.753 (2.0); 8.743 (2.0); 8.617 (3.6); 8.613 (3.6); 7.939 (3.9); 7.935 (3.8); 7.904 (1.9); 7.886 (2.1); 7.555 (1.7); 7.543 (1.8); 7.536 (1.7); 7.524 (1.6); 7.472 (4.6); 7.452 (5.9); 7.311 (4.9); 7.291 (3.9); 7.262 (45.2); 6.697 (0.7); 6.685 (1.2); 6.670 (0.7); 5.301 (0.9); 4.380 (0.5); 4.364 (0.5); 4.345 (1.0); 4.329 (1.2); 4.312 (0.5); 4.292 (1.1); 4.277 (1.1); 4.270 (1.1); 4.254 (1.0); 4.236 (1.5); 4.221 (1.5); 4.202 (0.5); 4.186 (0.5); 2.436 (0.5); 2.417 (16.0); 1.956 (9.6); 1.903 (9.6); 1.555 (47.1); 0.000 (42.8)

Example 38: $^1$H-NMR (400.0 MHz, CDCl$_3$):
δ = 8.756 (1.7); 8.747 (1.6); 8.744 (1.6); 8.714 (2.7); 8.709 (2.6); 8.627 (3.1); 8.622 (3.0); 7.948 (3.5); 7.943 (3.3); 7.912 (1.6); 7.895 (1.7); 7.893 (1.7); 7.780 (1.7); 7.774 (1.7); 7.760 (1.9); 7.754 (1.8); 7.562 (1.6); 7.551 (1.6); 7.543 (1.5); 7.531 (1.3); 7.307 (2.5); 7.287 (2.3); 7.264 (14.4); 6.658 (0.6); 6.644 (1.0); 6.630 (0.6); 5.302 (1.6); 4.389 (0.5); 4.374 (0.5); 4.354 (0.9); 4.338 (1.1); 4.321 (0.5); 4.302 (0.9); 4.286 (0.9); 4.274 (0.9); 4.258 (0.8); 4.240 (1.3); 4.224 (1.3); 4.205 (0.5); 4.189 (0.4); 2.654 (0.5); 2.635 (16.0); 2.618 (0.4); 2.474 (0.9); 1.958 (8.6); 1.905 (8.6); 1.608 (3.8); 0.007 (0.8); 0.000 (13.7); −0.008 (0.5)

Example 39: $^1$H-NMR (400.0 MHz, CDCl$_3$):
δ = 8.666 (5.3); 8.660 (6.3); 8.654 (5.6); 8.575 (4.6); 8.568 (4.7); 7.960 (6.1); 7.955 (6.0); 7.693 (2.8); 7.674 (3.5); 7.617 (1.9); 7.611 (2.5); 7.606 (2.6); 7.595 (2.1); 7.588 (5.0); 7.584 (3.0); 7.569 (3.0); 7.548 (2.5); 7.530 (7.3); 7.522 (0.9); 7.512 (2.7); 7.262 (55.7); 6.513 (0.9); 6.499 (1.6); 6.484 (0.9); 5.301 (11.3); 4.391 (0.8); 4.376 (0.9); 4.356 (1.6); 4.340 (2.3); 4.324 (0.9); 4.305 (1.6); 4.289 (1.6); 4.278 (1.6); 4.262 (1.6); 4.240 (2.0); 4.224 (2.0); 4.204 (0.9); 4.189 (0.8); 4.131 (0.3); 4.113 (0.4); 2.047 (1.6); 1.963 (15.9); 1.909 (16.0); 1.577 (45.8); 1.278 (0.5); 1.260 (1.2); 1.254 (1.0); 1.242 (0.6); 0.008 (1.6); 0.000 (49.9); −0.009 (1.8)

Example 40: $^1$H-NMR (400.0 MHz, CDCl$_3$):
δ = 8.764 (3.5); 8.755 (3.6); 8.667 (6.4); 8.652 (6.2); 8.648 (5.9); 8.581 (5.7); 8.574 (5.8); 8.491 (0.8); 7.975 (6.5); 7.970 (6.2); 7.953 (0.7); 7.948 (0.6); 7.925 (3.1); 7.905 (3.5); 7.877 (0.4); 7.617 (2.1); 7.612 (2.9); 7.606 (2.0); 7.595 (2.1); 7.590 (2.9); 7.584 (2.0); 7.571 (3.0); 7.559 (3.1); 7.552 (3.0); 7.540 (2.7); 7.521 (1.6); 7.262 (250.8); 6.998 (1.5); 6.575 (2.0); 4.401 (0.9); 4.385 (0.9); 4.366 (1.7); 4.350 (2.1); 4.333 (0.9); 4.313 (1.7); 4.298 (1.7); 4.284 (1.6); 4.268 (1.7); 4.249 (2.5); 4.233 (2.7); 4.219 (0.6); 4.214 (0.9); 4.198 (1.1); 4.184 (0.3); 4.149 (0.6); 4.131 (1.8); 4.113 (1.8); 4.096 (0.6); 2.047 (7.4); 1.964 (15.9); 1.911 (16.0); 1.896 (2.1); 1.843 (1.8); 1.552 (227.5); 1.427 (0.4); 1.333 (1.0); 1.284 (1.4); 1.278 (2.4); 1.260 (4.8); 1.243 (2.3); 0.880 (0.4); 0.846 (0.4); 0.146 (1.2); 0.000 (236.0); −0.150 (1.2)

BIOLOGICAL EXAMPLES

*Cooperia curticei*-Test (COOPCU)

Solvent: dimethyl sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded, 100% efficacy means all larvae are killed; 0% efficacy means no larvae are killed.

In this test for example, the following compounds from the preparation examples showed good activity of 100% at an application rate of 20 ppm: 1, 2, 3, 4, 6, 7, 8, 9, 10, 11, 12, 14, 15, 16, 17, 18, 19, 20, 22, 23, 24, 25, 28

In this test for example, the following compounds from the preparation examples showed good activity of 90% at an application rate of 20 ppm: 13

In this test for example, the following compounds from the preparation examples showed good activity of 80% at an application rate of 20 ppm: 21

*Haemonchus contortus*-Test (HAEMCO)

Solvent: dimethyl sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days percentage of larval mortality are recorded, 100% efficacy means all larvae are killed, 0% efficacy means no larvae are killed.

In this test for example, the following compounds from the preparation examples showed good activity of 100% at an application rate of 20 ppm: 2, 3, 4, 6, 10, 14, 15, 16, 19, 20, 23, 24, 25, 28

In this test for example, the following compounds from the preparation examples showed good activity of 90% at an application rate of 20 ppm: 5, 7, 9, 11, 12, 17, 22

In this test for example, the following compounds from the preparation examples showed good activity of 80% at an application rate of 20 ppm: 1, 18

*Meloidogyne incognita*-Test

Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined on the basis of the percentage of gall formation. 100% means no galls were found and 0% means the number of galls found on the roots of the treated plants was equal to that in untreated control plants.

In this test, for example, the following compounds from the preparation examples showed good activity of 1(0) % at an application rate of 20 ppm: 2, 3, 4, 5, 6, 10, 14, 16, 18, 23, 24, 25, 28, 29 In this test, for example, the following compounds from the preparation examples showed good activity of 90% at an application rate of 20 ppm: 7, 12, 13, 15, 20

*Nippostrongylus brasiliensis*-Test (NIPOBR) (In Vitro Efficacy Test)

Adult *Nippostrongylus brasiliensis* were washed with saline buffer containing 100 U/ml penicillin, 0.1 mg/ml streptomycin and 2.5 µg/ml amphotericin B. Test compounds were dissolved in DMSO, and worms were incubated in medium in a final concentration of 10 µg/ml. An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChe compared to negative control) was 60% or higher at 10 µg/ml: 2; 3; 4; 10; 14; 15; 16; 19; 25; 28

In Vivo Efficacy Test

*Haemonchus contortus/Trichostrongylus colubriformis*/gerbil

Gerbils, experimentally infected with *Haemonchus* and/or *Trichostrongylus*, were treated once during late prepatency. Test compounds were formulated as solutions or suspensions and applied intraperitoneally or orally.

Efficacy was determined per group as reduction of worm count in stomach and small intestine, respectively, after necropsy compared to worm count in an infected and placebo-treated control group.

The following examples were tested and had an activity of 85% or higher at the given treatment:

| Treatment | Haemonchus | Trichostrongylus |
|---|---|---|
| 20 mg/kg intraperitoneally | 16; 28 | 16; 28 |
| 10 mg/kg orally | 16 | |

The invention claimed is:
1. A compound of formula (I)

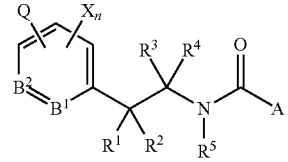

wherein
$B^1$ and $B^2$ represent C—X or N, wherein at least one of $B^1$ and/or $B^2$ is N,
n is 1 or 2, limited by the number of available positions in the ring to which a substituent X can be connected,
each X is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —COONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyl-oxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino,
Q represents an optionally mono- or polysubstituted heteroaromatic ring selected from the group consisting of Q-41, Q-42, Q-43, Q-44, Q-45, Q-46, Q-47, Q-48, Q-49, Q-50, Q-51, Q-52, and Q-53

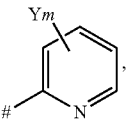

Q-41

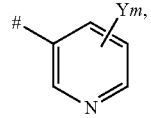

Q-42

-continued

Q-43 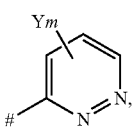

Q-44 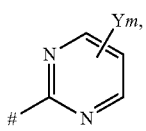

Q-45 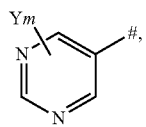

Q-46 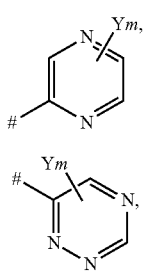

Q-47

Q-48 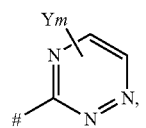

Q-49 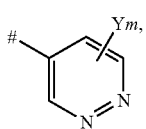

Q-50 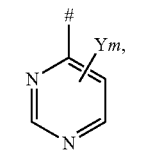

Q-51 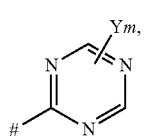

Q-52 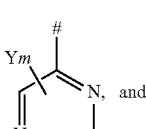, and

Q-53 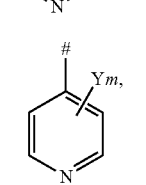

where
the symbol # indicates the point of attachment of each Q,
m is 0, 1 or 2, limited by the number of available positions in Q to which a substituent Y can be connected, and
each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino,
$R^1$, $R^2$, $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^1$ and R$^2$ together with the carbon atom to which they are bonded form a 4- or 5-membered carbocycle and R$^3$ and R$^4$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$ —C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^3$ and R$^4$ together with the carbon atom to which they are bonded form a 3-, 4- or 5-membered carbocycle and R$^1$ and R$^2$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^4$ and R$^2$ together with the carbon atom to which they are bonded form a 3-, 4- or 5-membered non-aromatic carbocycle optionally substituted by substituents selected from the group consisting of one to four C$_1$-C$_4$-alkyl groups and one to four halogen atoms, and R$^1$ and R$^3$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_3$-alkyl, C$_3$-C$_6$-halogenocycloalkyl-C$_1$-C$_3$-alkyl having 1 to 5 halogen atoms, C$_1$-C$_4$-alkylcarbonyl, C$_1$-C$_4$-halogenoalkylcarbonyl having 1 to 5 halogen atoms, —CONH(C$_1$-C$_4$-alkyl), —CON(C$_1$-C$_4$-alkyl)$_2$, —CONH(OC$_1$-C$_4$-alkyl), —CON(OC$_1$-C$_4$-alkyl)(C$_1$-C$_4$-alkyl), C$_1$-C$_4$-alkoxycarbonyl, C$_1$-C$_4$-halogenoalkoxycarbonyl having 1 to 5 halogen atoms, —OC(O)—C$_1$-C$_4$-alkyl, —OC(O)—C$_1$-C$_4$-halogenoalkyl having 1 to 5 halogen atoms, —NHC(O)—C$_1$-C$_4$-alkyl, —NHC(O)—C$_1$-C$_4$-halogenoalkyl having 1 to 5 halogen atoms, —OCONH(C$_1$-C$_4$-alkyl), —OCON(C$_1$-C$_4$-alkyl)$_2$, —OCONH(OC$_1$-C$_4$-alkyl), OCO(OC$_1$-C$_4$-alkyl), —S—C$_1$-C$_4$-alkyl, —S—C$_1$-C$_4$-halogenoalkyl having 1 to 5 halogen atoms, —S(O)—C$_1$-C$_4$-alkyl, —S(O)—C$_1$-C$_4$-halogenoalkyl having 1 to 5 halogen atoms, —S(O)$_2$—C$_1$-C$_4$-alkyl, —S(O)$_2$—C$_1$-C$_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or R$^1$ and R$^3$ together with the carbon atom to which they are bonded form a 3-, 4- or 5-membered non-aromatic carbocycle optionally substituted by substituents selected from the group consisting of one to four C$_1$-C$_4$-alkyl groups and one to four halogen atoms, and R$^2$ and R$^4$ are the same or different and are selected from the group consisting of hydrogen, halogen, cyano, hydroxy, amino, —CHO, —COOH, —CONH$_2$, C$_1$-C$_4$-alkyl, C$_2$-C$_4$-alkenyl, C$_2$-C$_4$-alkynyl, C$_1$-C$_4$-alkylamino, di-(C$_1$-C$_4$-alkyl)amino, C$_1$-C$_4$-alkoxy, C$_1$-C$_4$-halogenoalkyl having 1 to 5 halogen atoms, C$_1$-C$_4$-halogenoalkoxy having 1 to 5 halogen atoms, C$_2$-C$_4$-alkenyloxy, C$_2$-C$_4$-halogenoalkenyloxy having 1 to 5 halogen atoms, C$_3$-C$_4$-alkynyloxy, C$_3$-C$_4$-halogenoalkynyloxy having 1 to 5 halogen atoms, C$_3$-C$_6$-cycloalkyl, C$_3$-C$_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, $R^5$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_2$-$C_4$-alkenyl, $C_2$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di-($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —S(O)$_2$—$C_1$-$C_4$-alkyl, and S(O)$_2$—$C_1$-$C_4$-halogenoalkyl having 1 to 5 halogen atoms, and A represents a phenyl group of formula (A1)

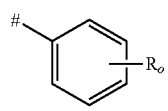

(A1)

in which
the symbol # indicates the point of attachment of A,
o is 0, 1 or 2, and
each R is independently selected from the group consisting of halogen, nitro, —OH, CHO, OCHO, NHCHO, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_3$-$C_6$-cycloalkyl, —S—$C_1$-$C_4$-alkyl, —S—$C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkoxy-$C_2$-$C_4$-alkenyl, $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, $C_1$-$C_4$-alkylsulfonamide, —NH($C_1$-$C_4$-alkyl), N($C_1$-$C_4$-alkyl)$_2$, phenyl (optionally substituted by $C_1$-$C_4$-alkoxy) and phenoxy, or two R bonded to adjacent carbon atoms together represent —O(CH$_2$)$_p$O—, wherein p represents 1 or 2, or A represents a heterocycle of the formula (Het-1)

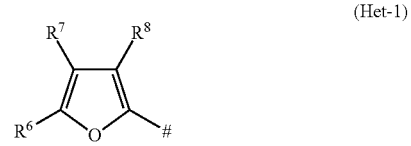

(Het-1)

in which
the symbol # indicates the point of attachment of A,
$R^6$ and $R^7$ are the same or different and are selected from the group consisting of hydrogen, halogen, nitro, $C_1$-$C_4$-alkyl and $C_1$-$C_4$-halogenoalkyl having 1 to 5 halogen atoms, and
$R^8$ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

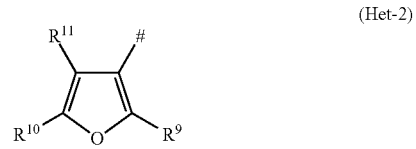

(Het-2)

in which
the symbol # indicates the point of attachment of A,
$R^9$ is selected from the group consisting of hydrogen, halogen, $C_1$-$C_4$-alkyl and $C_1$-$C_4$-halogenoalkyl having 1 to 5 halogen atoms, and
$R^{10}$ and $R^{11}$ are the same or different and are selected from the group consisting of hydrogen, halogen, $C_1$-$C_4$-alkyl, $C_1$-$C_4$-halogenoalkyl having 1 to 5 halogen atoms, and phenyl (optionally substituted by halogen or $C_1$-$C_4$-alkyl), or A represents a heterocycle of the formula (Het-4)

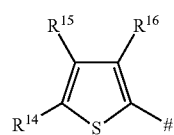

(Het-4)

in which
the symbol # indicates the point of attachment of A,
$R^{14}$ and $R^{15}$ are the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and
$R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A represents a heterocycle of the formula (Het-5)

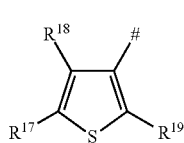

(Het-5)

in which
the symbol # indicates the point of attachment of A,
$R^{17}$ and $R^{18}$ are the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
$R^{19}$ is selected from the group consisting of hydrogen, halogen, $C_1$-$C_4$-alkyl and $C_1$-$C_4$-halogenoalkyl having 1 to 5 atoms, or
A represents a heterocycle of the formula (Het-6)

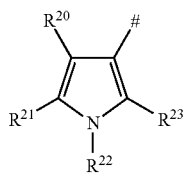

(Het-6)

in which
the symbol # indicates the point of attachment of A,
$R^{20}$ is selected from the group consisting of hydrogen, halogen, cyano, $C_1$-$C_4$-alkyl and $C_1$-$C_4$-halogenoalkyl having 1 to 5 halogen atoms,
$R^{21}$ and $R^{23}$ are the same or different and are selected from the group consisting of hydrogen, halogen, $C_1$-$C_4$-alkyl and $C_1$-$C_4$-halogenoalky having 1 to 5 halogen atoms, and
$R^{22}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, or
A represents a heterocycle of the formula (Het-7)

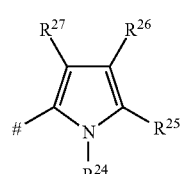

(Het-7)

in which
the symbol # indicates the point of attachment of A,
$R^{24}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, $C_1$-$C_6$-alkylcarbonyl, or benzoyl (optionally substituted by halogen or a $C_1$-$C_4$-alkyl), and
$R^{25}$, $R^{26}$ and $R^{27}$ are the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or A represents a heterocycle of the formula (Het-9)

(Het-9)

in which
the symbol # indicates the point of attachment of A,
$R^{30}$ is selected from the group consisting of hydrogen and $C_1$-$C_4$-alkyl, and
$R^{31}$ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or
A represents a heterocycle of the formula (Het-10)

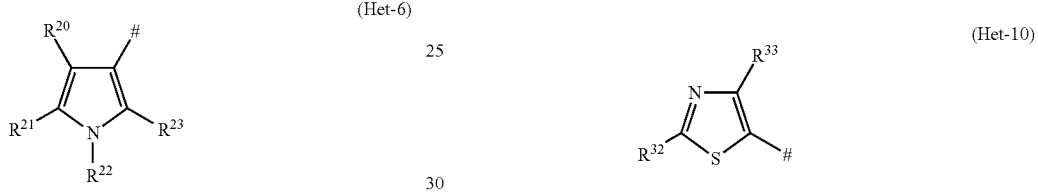

(Het-10)

in which
the symbol # indicates the point of attachment of A,
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and
$R^{33}$ is selected from the group consisting of halogen, $C_1$-$C_4$-alkyl, $C_1$-$C_4$-halogenoalkyl having 1 to 5 halogen atoms, $C_1$-$C_5$-halogenoalkoxy comprising 1 to 9 halogen atoms, amino, substituted or unsubstituted $C_1$-$C_5$-alkylamino and substituted or unsubstituted di-($C_1$-$C_5$-alkyl)-amino, or
A represents a heterocycle of the formula (Het-11)

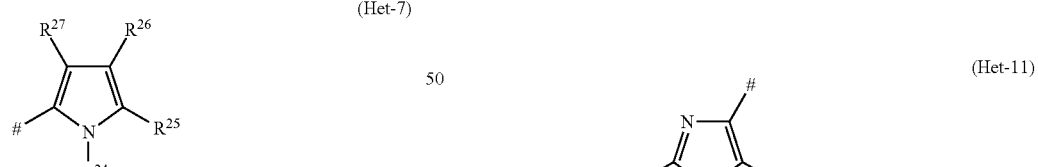

(Het-11)

in which
the symbol # indicates the point of attachment of A,
$R^{34}$ is selected from the group consisting of hydrogen, halogen, $C_1$-$C_4$-alkylamino, di-($C_1$-$C_4$-alkyl)amino, $C_1$-$C_4$-alkyl and $C_1$-$C_4$-halogenoalkyl having 1 to 5 halogen atoms, and
$R^{35}$ is selected from the group consisting of halogen, $C_1$-$C_4$-alkyl and $C_1$-$C_4$-halogenoalkyl having 1 to 5 halogen atoms, or A represents a heterocycle of the formula (Het-12)

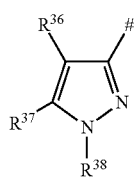
(Het-12)

in which
the symbol # indicates the point of attachment of A,
R³⁶ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl and —S—$C_1$-$C_4$-halogenoalkyl having 1 to 5 halogen atoms,
R³⁷ is selected from the group consisting of hydrogen, halogen, cyano, nitro, $C_1$-$C_4$-alkyl, $C_1$-$C_4$-alkoxy and —S—$C_1$-$C_4$-alkyl, —S(O)—$C_1$-$C_4$-alkyl, —S(O)$_2$—$C_1$-$C_4$-alkyl, and
R³⁸ is selected from the group consisting of phenyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$-$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or
A represents a heterocycle of the formula (Het-13)

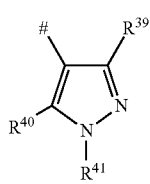
(Het-13)

in which
the symbol # indicates the point of attachment of A,
R³⁹ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 atoms, aminocarbonyl and aminocarbonyl-$C_1$-$C_4$-alkyl,
R⁴⁰ is selected from the group consisting of hydrogen, halogen, cyano, $C_1$-$C_4$-alkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, and —S(O)$_2$—$C_1$-$C_4$-alkyl, and
R⁴¹ is selected from the group consisting of hydrogen, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl, $C_1$-$C_4$-halogenoalkoxy-$C_1$-$C_4$-alkyl having 1 to 5 halogen atoms and phenyl optionally substituted by halogen, $C_1$-$C_4$-alkyl, $C_1$-$C_4$-alkoxy-$C_1$-$C_4$-alkyl or nitro, or
A represents a heterocycle of the formula (Het-14)

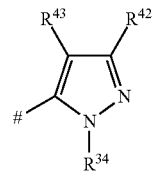
(Het-14)

in which
the symbol # indicates the point of attachment of A,
R⁴² is selected from the group consisting of hydrogen, halogen, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, and —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl,
R⁴³ is selected from the group consisting of hydrogen, halogen, cyano, $C_1$-$C_4$-alkyl, $C_1$-$C_4$-alkoxy, —S—$C_1$-$C_4$-alkyl, —S(O)—$C_1$-$C_4$-alkyl, and —S(O)$_2$—$C_1$-$C_4$-alkyl, and $C_1$-$C_4$-halogenoalkyl having 1 to 5 halogen atoms, and
R⁴⁴ is selected from the group consisting of phenyl, benzyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or
A represents a heterocycle of the formula (Het-15)

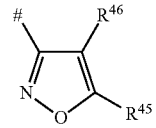
(Het-15)

in which
the symbol # indicates the point of attachment of A, and
R⁴⁵ and R⁴⁶ are the same or different and are selected from the group consisting of hydrogen, halogen, $C_1$-$C_4$-alkyl and $C_1$-$C_4$-halogenoalkyl having 1 to 5 halogen atoms, or
A represents a heterocycle of the formula (Het-16)

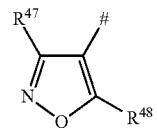
(Het-16)

in which the symbol # indicates the point of attachment of A, and $R^{47}$ and $R^{48}$ are the same or different and are selected from the group consisting of hydrogen, halogen, $C_1$-$C_4$-alkyl, $C_1$-$C_4$-halogenoalkyl having 1 to 5 halogen atoms, phenyl (optionally substituted by halogen or a $C_1$-$C_4$-alkyl), or heterocyclyl selected from the group consisting of pyridyl, pyrimidinyl and thiadiazolyl (each optionally substituted by halogen or $C_1$-$C_4$-alkyl), or A represents a heterocycle of the formula (Het-17)

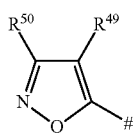

(Het-17)

in which the symbol # indicates the point of attachment of A, and $R^{49}$ and $R^{50}$ may be the same or different and are selected from the group consisting of hydrogen, halogen, $C_1$-$C_4$-alkyl and $C_1$-$C_4$-halogenoalkyl having 1 to 5 halogen atoms, or A represents a heterocycle of the formula (Het-19)

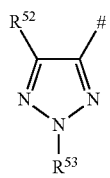

(Het-19)

in which the symbol # indicates the point of attachment of A, $R^{52}$ is selected from the group consisting of halogen, $C_1$-$C_4$-alkyl and $C_1$-$C_4$-halogenoalkyl having 1 to 5 halogen atoms, and $R^{53}$ is selected from the group consisting of $C_1$-$C_4$-alkyl, $C_1$-$C_4$-halogenoalkyl having 1 to 5 halogen atoms and phenyl (optionally substituted by halogen or $C_1$-$C_4$-alkyl), or A represents a heterocycle of the formula (Het-20)

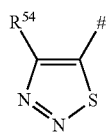

(Het-20)

in which the symbol # indicates the point of attachment of A, and $R^{54}$ is selected from the group consisting of halogen, $C_1$-$C_4$-alkyl and $C_1$-$C_4$-halogenoalkyl having 1 to 5 halogen atoms, or A represents a heterocycle of the formula (Het-21)

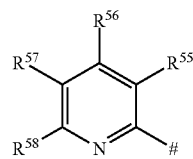

(Het-21)

in which the symbol # indicates the point of attachment of A, $R^{55}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which are the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-22)

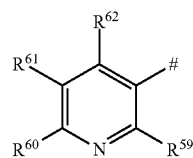

(Het-22)

in which the symbol # indicates the point of attachment of A, $R^{59}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, —S(O)—$C_1$-$C_4$-alkyl, —S(O)$_2$—$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), $R^{60}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or $C_1$-$C_4$-alkyl), and $R^{61}$ and $R^{62}$, which are the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or $C_1$-$C_4$-alkyl), or A represents a heterocycle of the formula (Het-23)

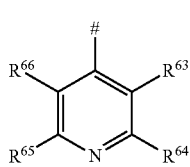
(Het-23)

in which the symbol # indicates the point of attachment of A, and $R^{63}$, $R^{64}$, $R^{65}$ and $R^{66}$, which are the same or different, are selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-24)

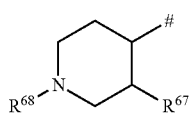
(Het-24)

in which the symbol # indicates the point of attachment of A, $R^{67}$ is selected from the group consisting of hydrogen, halogen, $C_1$-$C_4$-alkyl and $C_1$-$C_4$-halogenoalkyl having 1 to 5 halogen atoms, and $R^{68}$ is selected from the group consisting of $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms) and heterocyclyl selected from the group consisting of pyridyl and pyrimidinyl (optionally substituted by halogen, $C_1$-$C_4$-alkyl, or $C_1$-$C_4$-halogenoalkyl having 1 to 5 halogen atoms), or A represents a heterocycle of the formula (Het-25)

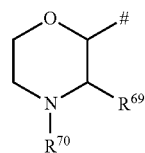
(Het-25)

in which the symbol # indicates the point of attachment of A, $R^{69}$ is selected from the group consisting of hydrogen, $C_1$-$C_4$-alkyl and $C_1$-$C_4$-halogenoalkyl having 1 to 5 halogen atoms, and $R^{70}$ is selected from the group consisting of hydrogen, $C_1$-$C_4$-alkyl, $C_1$-$C_4$-halogenoalkyl having 1 to 5 halogen atoms and benzyl, or A represents a heterocycle of the formula (Het-26)

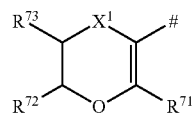
(Het-26)

in which the symbol # indicates the point of attachment of A, $X^1$ is selected from the group consisting of sulphur, —SO—, or —SO$_2$—, $R^{71}$ is selected from the group consisting of $C_1$-$C_4$-alkyl and $C_1$-$C_4$-halogenoalkyl having 1 to 5 halogen atoms, and $R^{72}$ and $R^{73}$ are the same or different and are selected from the group consisting of hydrogen and $C_1$-$C_4$-alkyl, or A represents a heterocycle of the formula (Het-29)

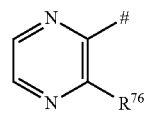
(Het-29)

in which the symbol # indicates the point of attachment of A, and $R^{76}$ is selected from the group consisting of hydrogen, halogen, $C_1$-$C_4$-alkyl and $C_1$-$C_4$-halogenoalkyl having 1 to 5 halogen atoms.

2. A compound according to claim 1, wherein $B^1$ and $B^2$ represent C—X or N, wherein at least one of $B^1$ and/or $B^2$ is N, n is 1, X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, Q represents an optionally mono- or polysubstituted heteroaromatic ring selected from the group consisting of Q-41, Q-42 and Q-53

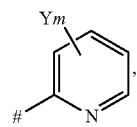
Q-41

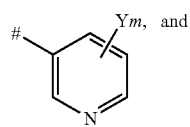
Q-42

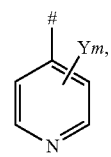
Q-53 where
m is 0, 1 or 2, limited by the number of available positions in Q to which a substituent Y can be connected, and each Y is independently selected from the group consisting of hydrogen, —$CF_3$, —$CH_2CF_3$, methyl, ethyl, fluorine, chlorine, bromine, iodine, cyano, —$OCH_3$, —$OCH_2CH_3$, —$OCH(CH_3)_2$, —$OCH_2CF_3$, —$CH_2$—$S(O)_2$—$CH_3$, and dimethylamino, $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, $R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, or $R^1$ and $R^2$ together with the carbon atom to which they are bonded form a 4- or 5-membered carbocycle, and $R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, optionally where $R^1$ and $R^2$ together with the carbon atom to which they are bonded form a cyclopentyl, or $R^3$ and $R^4$ together with the carbon atom to which they are bonded form a 3-, 4- or 5-membered carbocycle, and $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, optionally where $R^3$ and $R^4$ together with the carbon atom to which they are bonded form a cyclopropyl or a cyclobutyl, or $R^2$ and $R^4$ together with the carbon atom to which they are bonded form a 3-, 4- or 5-membered non-aromatic carbocycle optionally substituted by substituents selected from the group consisting of one to four $C_1$-$C_3$-alkyl groups and one to two halogen atoms, and $R^1$ is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and $R^3$ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, optionally where $R^2$ and $R^4$ together with the carbon atom to which they are bonded form a cyclopropyl, cyclobutyl or cyclopentyl, or $R^1$ and $R^3$ together with the carbon atom to which they are bonded form a 3-, 4- or 5-membered non-aromatic carbocycle optionally substituted by substituents selected from the group consisting of one to four $C_1$-$C_3$-alkyl groups and one to two halogen atoms, optionally cyclopropyl, cyclobutyl or cyclopentyl, and $R^2$ is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and $R^4$ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, optionally where $R^1$ and $R^3$ together with the carbon atom to which they are bonded form a cyclopropyl, cyclobutyl or cyclopentyl, $R^5$ is selected from the group consisting of hydrogen, $C_3$-$C_6$-cycloalkyl, $C_1$-$C_4$-alkylcarbonyl, and $C_1$-$C_4$-alkoxycarbonyl, and A represents a phenyl group of formula (A1)

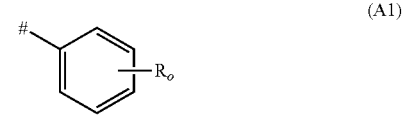

(A1)

in which
the symbol # indicates the point of attachment of A,
o is 0, 1 or 2, and
each R is independently selected from the group consisting of halogen, nitro, —OH, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1C_1$-$C_4$-alkoxycarbonyl, —NH($C_1$-$C_4$-alkyl), phenyl (optionally substituted by $C_1$-$C_4$-alkoxy) and phenoxy, or A represents a heterocycle of the formula (Het-1)

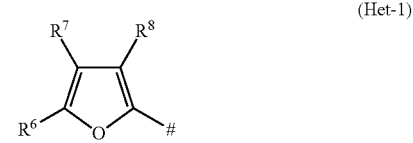

(Het-1)

in which
the symbol # indicates the point of attachment of A,
$R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and
$R^8$ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

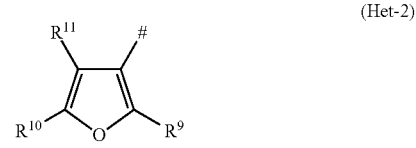

(Het-2)

in which the symbol # indicates the point of attachment of A, $R^9$ is selected from the group consisting of hydrogen, halogen, $C_1$-$C_4$-alkyl and $C_1$-$C_4$-halogenoalkyl having 1 to 5 halogen atoms, and $R^{10}$ and $R^{11}$ may be the same or different and are selected from the group consisting of hydrogen, halogen, $C_1$-$C_4$-alkyl and $C_1$-$C_4$-halogenoalkyl having 1 to 5 halogen atoms, and phenyl optionally substituted by halogen or $C_1$-$C_4$-alkyl), or A represents a heterocycle of the formula (Het-4)

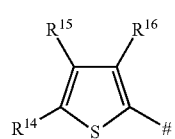

(Het-4)

in which the symbol # indicates the point of attachment of A, $R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and $R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A represents a heterocycle of the formula (Het-5)

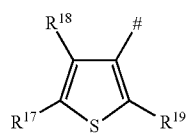

(Het-5)

in which the symbol # indicates the point of attachment of A, $R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and $R^{19}$ is selected from the group consisting of hydrogen, halogen, $C_1$-$C_4$-alkyl and $C_1$-$C_4$-halogenoalkyl having 1 to 5 atoms, or A represents a heterocycle of the formula (Het-6)

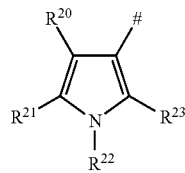

(Het-6)

in which the symbol # indicates the point of attachment of A, $R^{20}$ is selected from the group consisting of hydrogen, halogen, cyano, $C_1$-$C_4$-alkyl and $C_1$-$C_4$-halogenoalkyl having 1 to 5 halogen atoms, $R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and $R^{22}$ is selected from the group consisting of hydrogen, cyano, $C_1$-$C_4$-alkyl, $C_1$-$C_4$-halogenoalkyl having 1 to 5 halogen atoms, and $C_1$-$C_4$-alkoxy-$C_1$-$C_4$-alkyl, or A represents a heterocycle of the formula (Het-10)

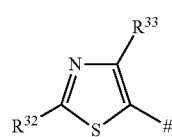

(Het-10)

in which the symbol # indicates the point of attachment of A, $R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and $R^{33}$ is selected from the group consisting of halogen, $C_1$-$C_4$-alkyl, $C_1$-$C_4$-halogenoalkyl having 1 to 5 halogen atoms, $C_1$-$C_5$-halogenoalkoxy comprising 1 to 9 halogen atoms, amino, substituted or unsubstituted $C_1$-$C_5$-alkylamino and substituted or unsubstituted di-($C_1$-$C_5$-alkyl)-amino, or A represents a heterocycle of the formula (Het-21)

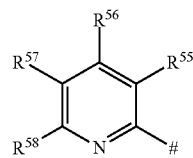

(Het-21)

in which the symbol # indicates the point of attachment of A, $R^{55}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl and —S(O)$_2$—$C_1$-$C_4$-alkyl, or A represents a heterocycle of the formula (Het-22)

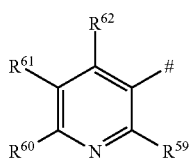
(Het-22)

in which
the symbol # indicates the point of attachment of A,
R⁵⁹ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, —S(O)—$C_1$-$C_4$-alkyl, —S(O)$_2$'$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), and
R⁶⁰, R⁶¹ and R⁶², which are the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or a $C_1$-$C_4$-alkyl), or
A represents a heterocycle of the formula (Het-29)

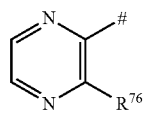
(Het-29)

in which
the symbol # indicates the point of attachment of A, and
R⁷⁶ is selected from the group consisting of hydrogen, halogen, $C_1$-$C_4$-alkyl and $C_1$-$C_4$-halogenoalkyl having 1 to 5 halogen atoms.

3. A compound according to claim 1, wherein
B¹ represents N,
B² represents CH,
n is 1,
X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms,
Q is

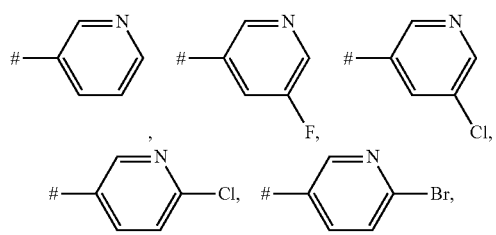

-continued

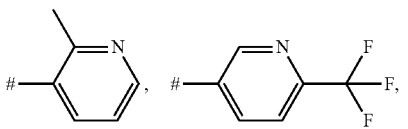
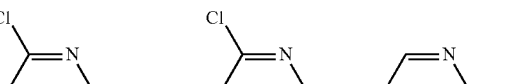
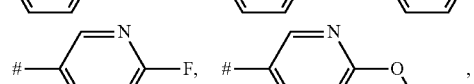
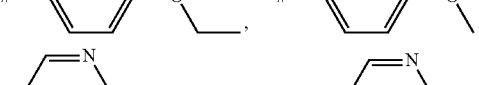
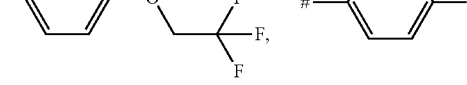
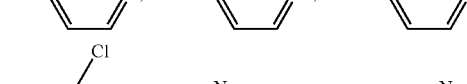
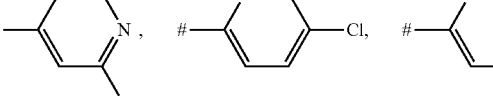
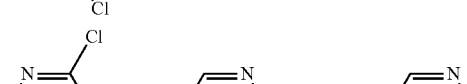
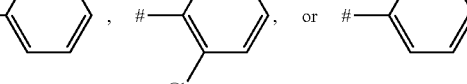
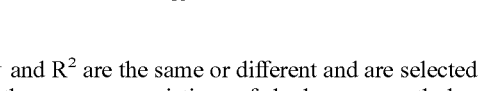

R¹ and R² are the same or different and are selected from the group consisting of hydrogen, methyl, ethyl, methoxy, ethoxy and fluorine, R³ and R⁴ are the same or different and are selected from the group consisting of hydrogen, methyl and ethyl, R⁵ is hydrogen, and A is

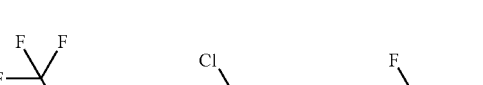
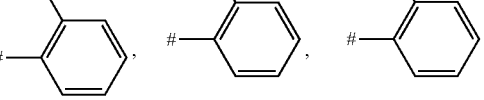
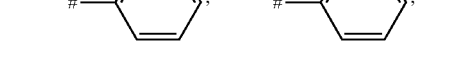

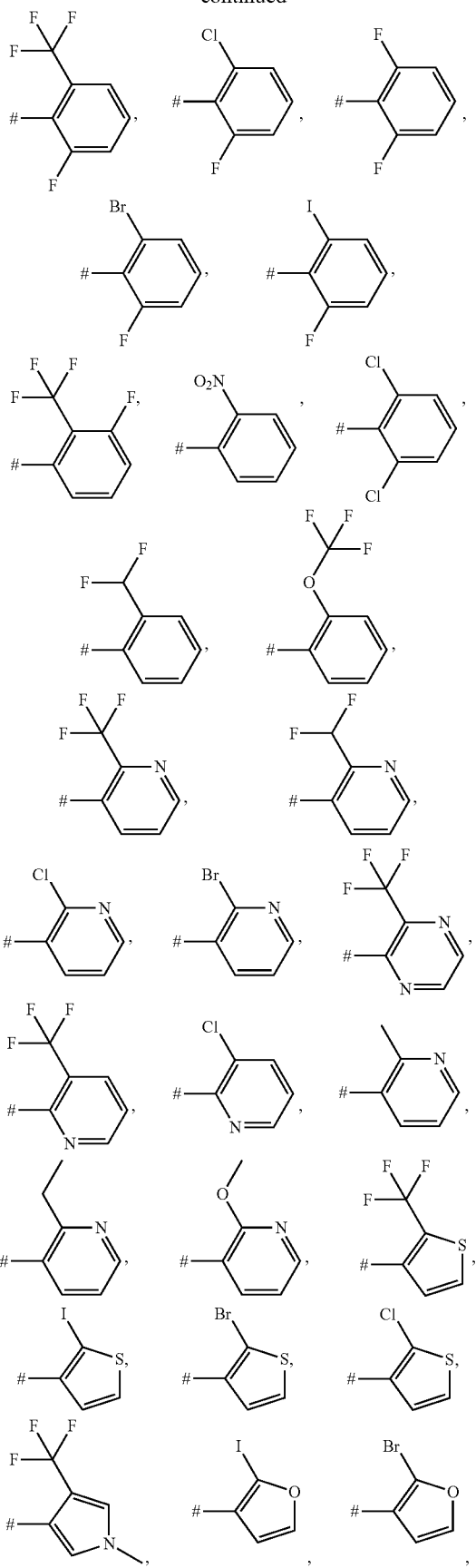
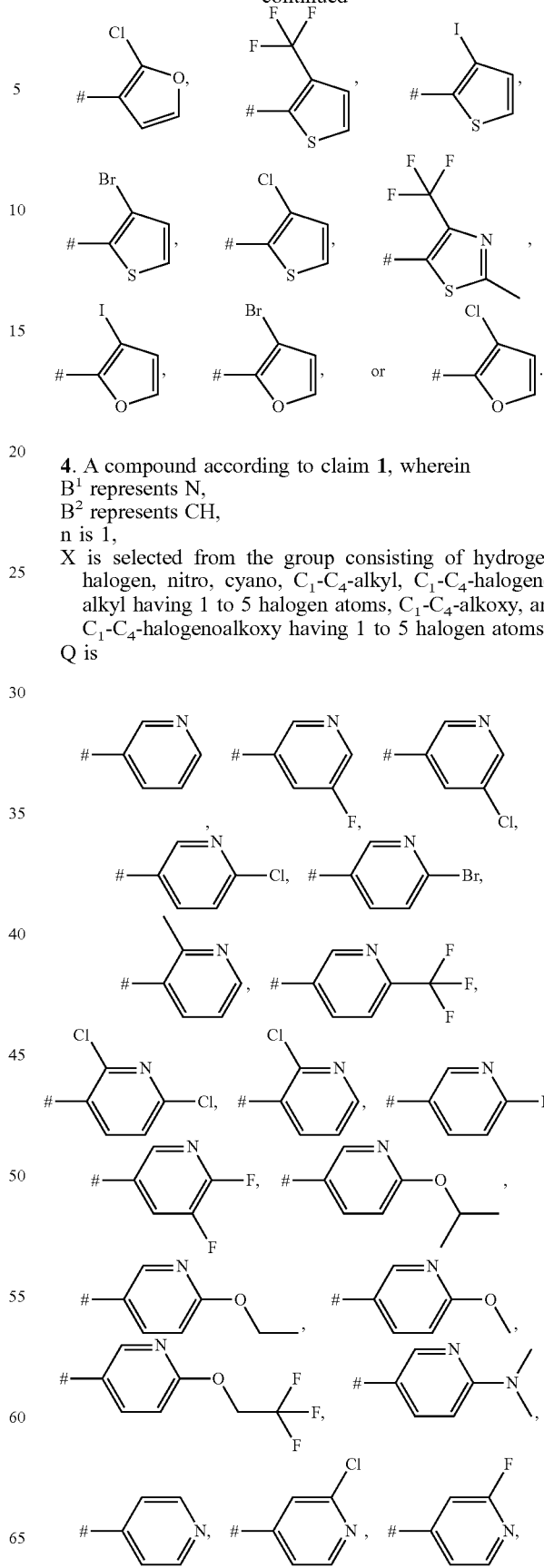
4. A compound according to claim 1, wherein
B$^1$ represents N,
B$^2$ represents CH,
n is 1,
X is selected from the group consisting of hydrogen, halogen, nitro, cyano, C$_1$-C$_4$-alkyl, C$_1$-C$_4$-halogenoalkyl having 1 to 5 halogen atoms, C$_1$-C$_4$-alkoxy, and C$_1$-C$_4$-halogenoalkoxy having 1 to 5 halogen atoms,
Q is -continued

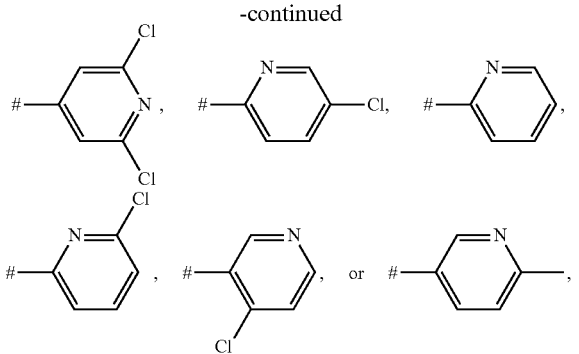

R[1] is selected from the group consisting of hydrogen, methyl, ethyl, methoxy, ethoxy and fluorine,
R[3] is selected from the group consisting of hydrogen, methyl and ethyl,
R[2] and R[4] together with the carbon atom to which they are bonded form a cyclobutane ring,
R[5] is hydrogen,
A is

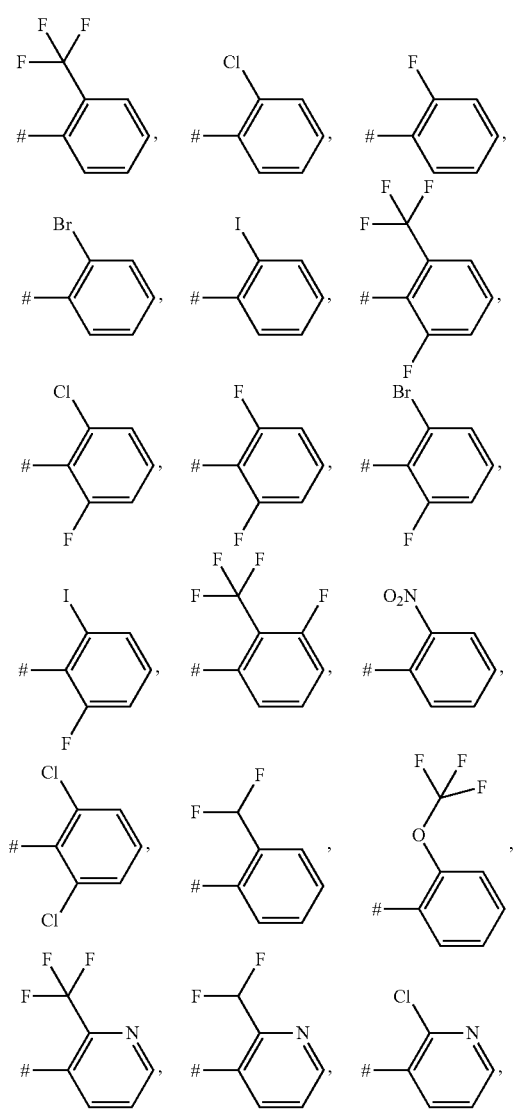

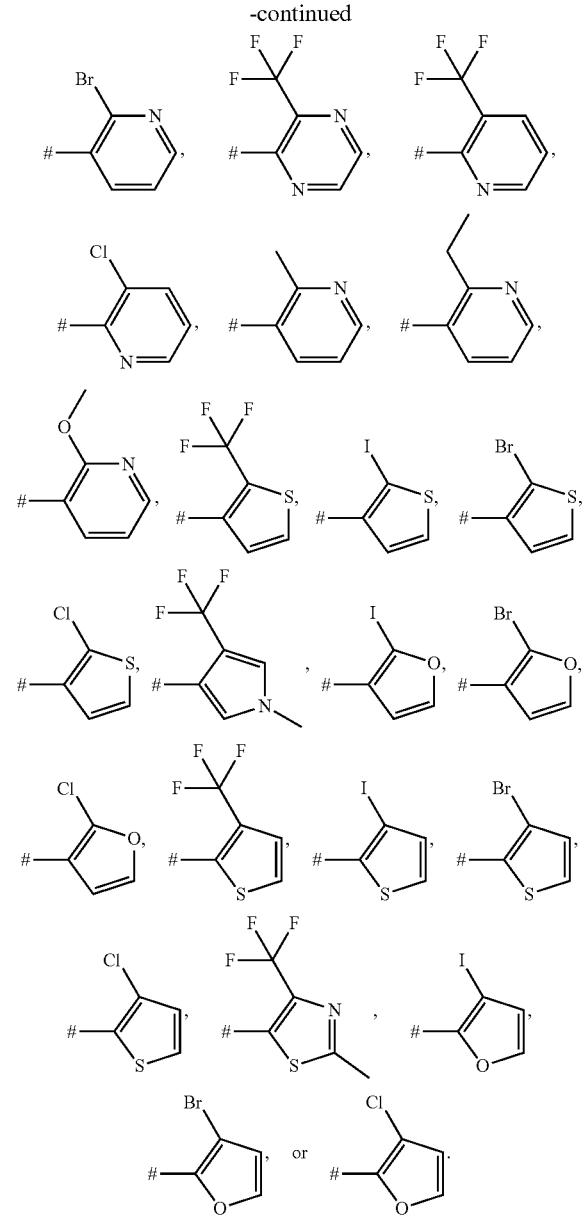

5. A compound according to claim 1, wherein Q is in the para-position.

6. A compound of the formula (I) according to claim 1 capable of being used for controlling animal pests, optionally comprising nematodes, in crop protection.

7. A compound of the formula (I) according to claim 1 capable of being used for controlling animal pests, optionally comprising nematodes, in the veterinary sector.

8. A compound according to claim 1 wherein
B[1] represents N,
B[2] represents CH,
n is 1,
X is hydrogen or halogen,
Q represents an optionally mono- or polysubstituted heteroaromatic ring selected from the group consisting of Q-41, Q-42, and Q-53

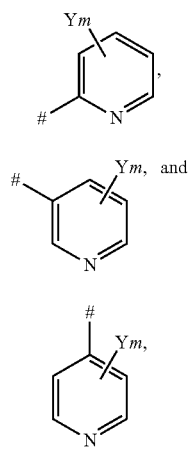

Q-41

Q-42

Q-53 wherein Q is in the para-position, m is 0, 1, or 2, each Y is independently selected from the group consisting of hydrogen, halogen, $C_1$-$C_4$-alkyl, $C_1$-$C_4$-halogenoalkyl having 1 to 5 halogen atoms, di-($C_1$-$C_4$-alkyl) amino, and $C_1$-$C_4$-alkoxy, $R^1$ and $R^2$ are the same or different and are selected from the group consisting of hydrogen, halogen, and $C_1$-$C_4$-alkyl, $R^3$ and $R^4$ are each hydrogen, $R^5$ is hydrogen, and A represents a phenyl group of formula (A1)

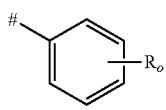

(A1)

in which the symbol # indicates the point of attachment of A, o is 0, 1 or 2, and R is $C_1$-$C_4$-halogenoalkyl, or A represents a heterocycle of the formula (Het-22)

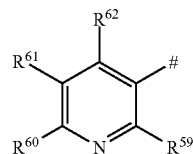

(Het-22)

in which the symbol # indicates the point of attachment of A, $R^{59}$ is $C_1$-$C_4$-halogenoalkyl having 1 to 5 halogen atoms, $R^{60}$ is hydrogen, and $R^{61}$ and $R^{62}$ are each hydrogen, or A represents a heterocycle of the formula (Het-29)

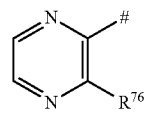

(Het-29)

in which the symbol # indicates the point of attachment of A, and $R^{76}$ is $C_1$-$C_4$-halogenoalkyl having 1 to 5 halogen atoms.

9. A composition comprising at least one compound of formula (I) according to claim 1.

10. A composition according to claim 9 which further comprises at least one additional active ingredient.

11. A composition comprising an effective amount of at least one compound of formula (I) according to claim 1 and at least one surfactant, solid or liquid diluent.

12. A method for controlling a nematode comprising contacting the nematode or its environment with a biologically effective amount of a compound of formula (I) according to claim 1.

13. A method for controlling a nematode comprising contacting the nematode or its environment with a composition according to claim 9.

14. A method for protecting a seed from a nematode comprising contacting the seed with a biologically effective amount of a compound of formula (I) according to claim 1.

15. A seed obtained by a method according to claim 14.

* * * * *